(12) United States Patent
Cohen-Haguenauer

(10) Patent No.: US 6,312,948 B1
(45) Date of Patent: Nov. 6, 2001

(54) RETROVIRAL VECTOR FOR THE TRANSFER AND EXPRESSION OF GENES FOR THERAPEUTIC PURPOSES IN EUKARYOTIC CELLS

(76) Inventor: Odile Cohen-Haguenauer, 35 rue Cortambert, 75116 Paris (FR)

( * ) Notice: Subject to any disclaimer, the term of this patent is extended or adjusted under 35 U.S.C. 154(b) by 0 days.

(21) Appl. No.: 09/433,322

(22) Filed: Nov. 3, 1999

Related U.S. Application Data

(63) Continuation of application No. 08/270,662, filed on Jun. 30, 1994, now abandoned.

(30) Foreign Application Priority Data

Jun. 30, 1993 (FR) .................................................. 93 08015

(51) Int. Cl.⁷ ............................ C12N 15/63; C12N 15/86
(52) U.S. Cl. .................................. 435/320.1; 435/235.1; 435/440; 435/455; 435/456; 536/24.1
(58) Field of Search ............................. 435/320.1, 235.1, 435/440, 455, 456; 536/24.1

(56) References Cited

U.S. PATENT DOCUMENTS

| | | |
|---|---|---|
| 4,650,764 | 3/1987 | Temin et al. . |
| 5,124,263 | 6/1992 | Temin et al. . |

FOREIGN PATENT DOCUMENTS

| | | |
|---|---|---|
| 611 822 | 2/1994 | (EP) . |
| 632 129 | 5/1994 | (EP) . |
| 2707091 | 5/1993 | (FR) . |
| WO 89/11539 | 11/1989 | (WO) . |
| WO 90/02797 | 3/1990 | (WO) . |
| WO 90/06757 | 6/1990 | (WO) . |
| WO 91/12329 | 8/1991 | (WO) . |
| WO 92/05266 | 4/1992 | (WO) . |
| WO 94/05780 | 3/1994 | (WO) . |

OTHER PUBLICATIONS

Verma, Gene Therapy: Beyond 2000, Jun. 2000, Molecular Theapy, vol. 1, No. 6 p. 493.*

Dang et al., Gene Therapy and Translational Cancer Research, Feb. 1999, Clinical Cancer Research, vol. 5 pp. 471–474.*

Orkin et al., Report and Recommendations of the Panel to Assess the NIH Investment in research on gene therapy, Dec. 1995, distributed by the National Institutes of Health, Bethesda, MD or www.nih.gov.*

Verma et al., Gene therapy–promises, problems and prospects, Sep. 1997, Nature, vol. 389, pp. 239–242.*

Corrine Ronfort et al., "Defective Retroviral Endogenous RNA is Efficiently Transmitted by Infectious Particles Produced on an Avian Retroviral Vector Packaging Cell Line", Virology 207:271–275 (Feb. 1995).

Corrine Ronfort et al., "Structure and Expression of Endogenous Retroviral Sequences in the Permanent LMH Chicken Cell Line", Poultry Science, 74, 127–135 (1995).

Idali Martinez et al., "Improved Retroviral Packaging Lines Derived from Spleen Necrosis Virus", Virology 208:234–241 (1995).

Francois Loic Cosset et al., "A New Avian Leukosis Virus–Based Packaging Cell Line that uses Two Separate Transcomplementing Helper Genomes", Journal of virology, 64(3):1070–1078(Mar. 1990).

Francois Loic Cosset et al., "High–Titer Packaging Cells Producing Recombinant Retroviruses Resistant to Human Serum", Journal of virology, 69(12):7430–7436(Dec. 1995).

M.E. Hotalin et al., "Amplified and tissue–directed expression of retroviral vectors using ping–pong techniques", J. Mol. Med. 73:113–120(1995).

Rolf M. Flugel et al., "Nucleotide sequence analysis of the env gene and its flanking regions of te human spumaretrovirus reveals two novel genes", The EMBO Journal 6(7):2077–2084(1987).

Bosselman et al., "Replication–Defective Chimeric Helper Proviruses and Factors Affecting Generation of Competent Virus: Expression of Moloney Murine Leukemia Virus Structural Genes via the Metallothionein Promotor", Mol. Cell. Biol., vol. 7, No. 5, pp. 1797–1806 (May 1987).

Kabat, D., "Molecular Biology of Friend Viral Erythroleukemia", Current Topics in Microbiology and Immunology, 148:1–42 (1989).

Watson et al. (1987) in : Molecular Biology of the Gene, Benjamin/Cummings Publ. Co., Menlo Park, CA, p. 313.

O. Cohen–Haguenauer, et al.; "Transduction of human CD34+ haemopoietic progenitors of various origin using an original retrovirus vector derived from Fr–MuLV and clinically relevant procedures"; *Hematology Cell Therapy*; 1996; pp. 205–206 (copy enclosed).

(List continued on next page.)

*Primary Examiner*—Deborah J. R. Clark
*Assistant Examiner*—Eleanor Sorbello

(57) ABSTRACT

The invention relates to a recombinantvector for the cloning and/or expression and/or transfer of an exogenous nucleotide sequence characterized in that it consists of any sequence contained in the ClaI—PvuII fragment comprising nucleotides 7702 to 1527 of the sequence given in FIG. 1 and comprising the LTR sequence included between nucleotides 7842 and 144, the PBS site starting at nucleotides 145, the packaging sequence included in the sequences of 250 nucleotides following the end of the LTR sequence, the said sequence being capable of controlling the cloning and/or expression and/or transfer of the exogenous sequence whatever its transcriptional orientation with respect to the transcriptional orientation of the virus.

Figure 1C:
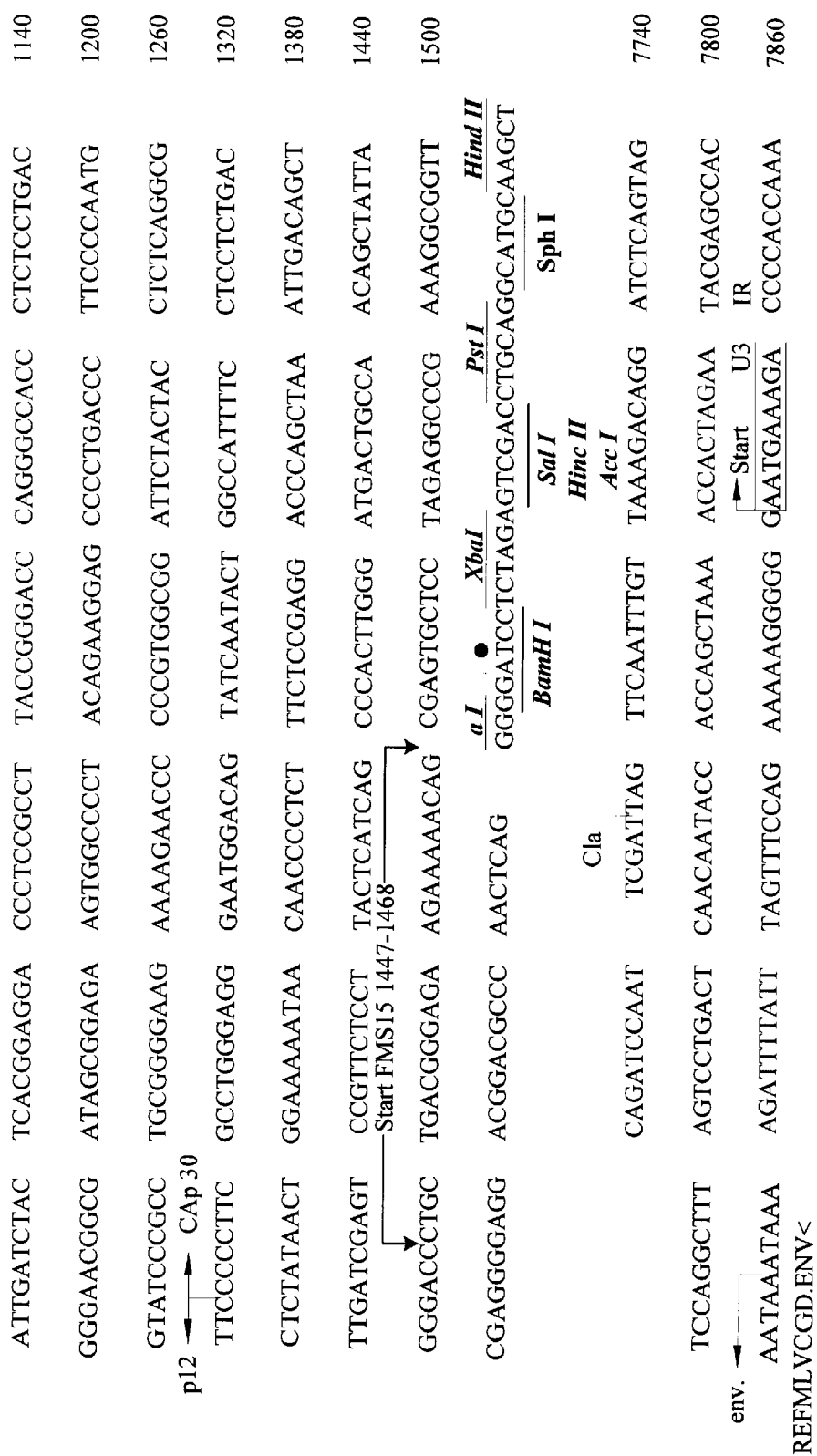

It relates to the use of this vector for the transfer and/or cloning and/or expression of genes, in particular in the contest of gene therapy.

23 Claims, 32 Drawing Sheets

OTHER PUBLICATIONS

Joyner et al., *Prog. Cancer Res. Ther.*, 30:89–96 (1984).
Feldman et al., *J. Virology*, 63(12):5469–5474 (1989).
Holland et al., *PNAS USA*, 84: 8662–8666 (1987).
Velu et al., *Human Gene Transfer*, 219: 273–274 (1991).
Bestwick et al., "Overcoming Interference to Retroviral Superinfection Results in Amplified Expression and Transmission of Cloned Genes", *Proc. Natl. Acad. Sci. USA*, 85:5404–5408 (Aug. 1988).
Danos et al., "Safe and Efficient Generation of Recombinant Retroviruses with Amphotropic and Ecotropic Host Ranges", *Proc. Natl. Acad. Sci. USA*, 85: 6460–6464 (Sep. 1988).
Mclachlin et al., "Retroviral–Mediated Gene Transfer", *Progress in Nucleic Acid Res. and Molecular Biology*, 38: 91–135, (1990).
Mulligan RC, "The Basic Science of Gene Therapy", *Science*, 260:926–931 (May 14, 1993).
Perryman et al., "Complete Nucleotide Sequence of Friend Murine Leukemia Virus, Strain FB29", *Nucleic Acids Res.*, 19:6950 (Nov. 1991).
Sitbon et al., "Hemolytic Anemia and Erythroleukemia, Two Distinct Pathogenic Effects of Friend MuLV: Mapping of the Effects to Different Regions of the Viral Genome", *Cell*, 47:851–859 (Dec. 1986).
Temin H.M., "Safety Considerations in Somatic Gene Therapy of Human Disease with Retrovirus Vectors", *Hum. Gene Ther.*, 1:111–123, (1990).
Sitbon et al., "Sequences in the U5–gag–pol Region Influence Early and Late Pathogenic Effects of Friend and Moloney Murine Leukemia Viruses", *U. Virol.*, 64:2135–2140 (May 1990).

Perryman et al., "Retroviral Expression Vector pSFF DNA, Complete Sequence", *Nucleic Acids Res.*, cited in GenBank Database, Bethesda, US, GenBank ACC. No. (GBN)Z22761 (May 19, 1993).
Yu et al. "Open Reading Frame vpr of Simian Immunodeficiency Virus encodes a Virion–Associated Protein", *J. Virol*. 64:5688–5693 (Nov. 1990).
Yu et al., "Self–Inactivating Retroviral Vectors Designed for Transfer of Whole Genes Into Mammalian Cell", *Proc. Natl. Acad. Sci.*, 83:3194–3198 (May 1986).
Fields, et al.; "Transformation by Molecular Mimicry and Insertional Mutagenesis: Friend Leukemia Virus"; *Virology*; pp. 323–324 (1996). (copy enclosed).
Ruan K.S., et al.; "Approach to a retrovirus vaccine: Immunization of mice against Friend virus disease with a replication–defective"; *Proc. Natl. Acad. Sci. US*; 89:24 (Dec. 15, 1992). Accession No. 93101695 Medline abstract of Proc. Natl. Acad. Sci. 89:12202–6. (copy enclosed).
Jolly, D., "Viral vector systems for gene therapy", *Cancer Gene Therapy*, 1(1):51–64 (1994).
Berger et al., Accession No. 86016806 Medline abstract of Proc. Natl. Acad. Sci. 82:6913 (Oct. 1985). (copy enclosed).
Evans et al., Accession No. 80052056 Medline abstract of J. Virology 31: 133 (Jul. 1979) (copy enclosed).
French Search Report for FR 9308015 dated Mar. 2, 1994 (copy enclosed).
Copy of International Search Report for PCT/FR94/00806 dated Oct. 19, 1994 (copy enclosed.
Fields, B. et al., "Cell Transformation by Viruses", *Virology*, 3rd Edition, p. 323 (1996).

* cited by examiner

FIG. 1A

```
                                              EcoRI
                                        AGTGAATTC   CGATTAGTTCAATTTGTTAAAGACAGGATCTCAGTAG 7740
                                       env
                                       AATAAATAAAAGATTTTATT TAGTTTCCAG AAAAAGGGGGGAATGAAAGA CCCCACCCAAA 7860
REFMLVCGD.ENV                                                             start U3   IR
TCCAGGCTTT AGTCCTGACT CAACAATACC ACCAGCTAAA ACCACTAGAA TACGAGCCAC 7800
TTGCTTAGCC TGATAGCCGC AGTAACGCCA TTTTGCAAGG CATGGAAAAA TACCAAACCA 7920
            LTR 81
AGAATAGAGAAGTTCAGATC AAGGGGCGGGT ACACGAAAAC AGCTAACGTT GGGCCAAACA 7980
GGATATCTGC GGTGAGCAGT TCGGCCCCG GCCCGGGGCC AAGAACAGA TGGTCACCGCG 8040
                                                                          +281
GTTCGGCCCC GGCCCGGGGC CAAGAACAGA TGGTCCCCAG ATATGGCCCA ACCCTCAGCA 8100
GTTTCTTAAG ACCCATCAGA TGTTCCAGG CTCCCCCAAG GACCTGAAAT GACCCTGTGC 8160
CTTATTTGAA TTAACCAATC AGCCTGCTTC TCGCTTCTGT TCGGCGGCTT CTGCTTCCCG 8220
AGCTCTATAA AAGAGCTCAC AACCCCTCAC                                   AATCCCTCTTG 60
 R                                             U3
GCGCCAGTCC TCCGATAGAC TGAGTCGCCC GGGTACCCGT GTATCCAATA AATCCCTCTTG 60
                                            SmaI     tcg   KpnI
CTGTTGCATC CGACTCGTGG TCTCGCGTGT CCTTGGGAGG GTCTCCCTCAG AGTGATTGAC 120
  U5                                PBS
TACCCGTCTC GGGGGTCTTT CATTTGGGGG CTCGTCCGGG ATCTGGAGAC CCCTGCCCAG 180
                                       SD
GGACCACCGA CCCACCACCG GGAGGTAAGC TGGCCAGCAA TTGTTCTGTG TCTGTCCATT 240
                                                              SpeI
GTCCTGTGTC TTTGATTGAT TTATGCGCC TGTGTCTGTA CTAGTTGGCC GACTAGATTG 300
```

FIG. 1B

```
                                                                                        PR75 GCSA
         ┌Bam HI┐                                                                          →
GTATCTGGCG GATCCGTGGT GGAACTGACG AGTTCGAGAC ACCCGGCCGC AACCCTGGGA 360
GACGTCCCAG GGACTTCGGG GGCCATTTTT GTGGCCCGGC CAGAGTCCAA CCATCCCGAT 420
CGTTTGGAC  TCTTTGGTGC ACCCCCCTTA GAGGAGGGGT ATGTGGTTCT GGTAGGAGAC 480
AGAGGGCTAA AACGGTTCC  GCCCCCGTCT GAGTTTTTGC TTCGGTTTG  GAACCGAAGC 540
CGCGCCGCGC GTCTTGTCTG CTGCAGCATC GTTCTGTGTT GTCTCTGTTT GACTGTTTTT 600
                      └PstI─┐
                            │
                      ↑gag
CTGTATTTGT CTGAAAAACAT GGGCCAGGCT GTTACCACCC CCTTAAGTTT GACTTTAGAC 660
          >REFMLVCGD.GAG   Map 15
CACTGGAAGG ATGTCGAACG GACAGCCCAC AACCTGTCGG TAGAGGTTAG AAAAAGGCGC 720
TGGGTTACAT TCTGCTCTGC AGAATGGCCA ACTTCAACG  TCGGATGGCC ACGAGACGGC 780
ACTTTAAACC CAGACATTAT TACACAGGTT AAGATCAAGG TCTTCTCACC TGGCCCACAT 840
GGACATCCGG ATCAGGTCCC CTACATCGTG ACCTGGGAAG CTATAGCAGT AGACCCCCT  900
CCCTGGGTCA GACCCCTTCGT GCACCCTAAA CCTCCCCCTCT CTCTTCCCCC TTCAGCCCCC 960
                                                                        pp12
                                                                  Map 15  →
TCTCTCCCAC CTGAACCCCC ACTCTCGACC CCGCCCCAGT CCTCCCTCTA TCCGGCTCTC 1020
                                 └StuI─┐
ACTTCTCCTT TAAACACCAA ACCTAGGCCT CAAGTCCTTC CTGATAGCGG AGGACCACTC 1080
```

FIG.4

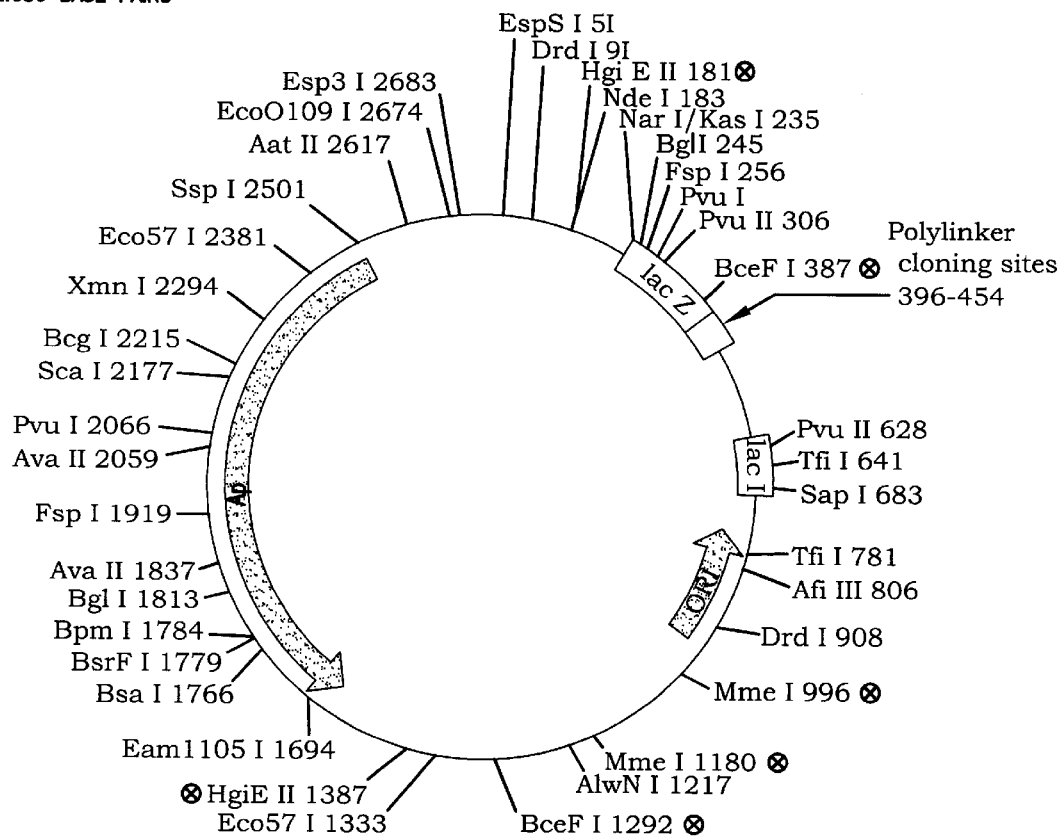

pUc19
(ATCC 37254)
2,686 BASE PAIRS

```
                Ecl 136 I  Xma I
        Sac I     Sma I      Xba I      Pst I     Hind III
   agtgaattCGAGCTCGGTACCCGGGGATCCTCTAGAGTCGACCTGCAGGCATGCAAGCTTGGcgtaatcatggtcat
        EcoR I   Kpn I  BamH I    Sal I       Sph I
        Apo I    Acc65 I          Hinc II
                                  Acc I
                                  BspM I
```
                                                                                    1
LacZ'—Ala Leu Ser Asn Ser Ser Pro Val Arg Pro Asp Glu Leu Thr Ser Arg Cys Ala His Leu Ser Pro Thr. Ile Met Thr References
1. Yaniish-Perron, C., Vieira, J. and Messing, J.(1985)Gene 33, 103-119
2. Genbank Accession # VB0026(Vecbase:pUC19c)

FIG. 5A

```
        ┌──► R                              ┌─KpnI─┐
GCGCCAGTCC TCCGATAGAC TGAGTCGCCC GGGTACCCGT GTATCCAATA AATCCTCTTG   60
        ┌─U5          ┌──────── └─SmaI─┘
CTGTTGCATC CGACTCGTGG TCTCGCTGTT CCTTGGGAGG GTCTCCTCAG AGTGATTGAC  120
               ┌────────TR   ┌─►PBS
TACCCGTCTC GGGGGTCTTT CATTTGGGGG CTCGTCCGGG ATCTGGAGAC CCCTGCCCAG  180
                       ┌─SD─┐
GGACCACCGA CCCACCACCG GGAGGTAAGC TGGCCAGCAA TTGTTCTGTG TCTGTCCATT  240
                                               ┌─SpeI─┐
GTCCTGTGTC TTTGATTGAT TTTATGCGCC TGTGTCTGTA CTAGTTGGCC GACTAGATTG  300
         └─BamHI─┘                                           ┌─Pr75 GCSA
GTATCTGGCG GATCCGTGGT GGAACTGACG AGTTCGAGAC ACCCGGCCGC AACCCTGGGA  360

GACGTCCCAG GGACTTCGGG GGCCATTTTT GTGGCCCGGC CAGAGTCCAA CCATCCCGAT  420

CGTTTTGGAC TCTTTGGTGC ACCCCCCTTA GAGGAGGGGT ATGTGGTTCT GGTAGGAGAC  480

AGAGGGCTAA AACGGTTTCC GCCCCCGTCT GAGTTTTTGC TTTCGGTTTG GAACCGAAGC  540
                                ┌─PstI─┐
CGCGCCGCGC GTCTTGTCTG CTGCAGCATC GTTCTGTGTT GTCTCTGTTT GACTGTTTTT  600
             ┌── gag
CTGTATTTGT CTGAAAACAT GGGCCAGGCT GTTACCACCC CCTTAAGTTT GACTTTAGAC  660
           >REFMLVCGD.GAG   MAp15
CACTGGAAGG ATGTCGAACG GACAGCCCAC AACCTGTCGG TAGAGGTTAG AAAAAGGCGC  720

TGGGTTACAT TCTGCTCTGC AGAATGGCCA ACCTTCAACG TCGGATGGCC ACGAGACGGC  780

ACTTTTAACC CAGACATTAT TACACAGGTT AAGATCAAGG TCTTCTCACC TGGCCCACAT  840

GGACATCCGG ATCAGGTCCC CTACATCGTG ACCTGGGAAG CTATAGCAGT AGACCCCCT   900

CCCTGGGTCA GACCCTTCGT GCACCCTAAA CCTCCCCTCT CTCTTCCCCC TTCAGCCCCC  960
                                                MAp15 ──┬──► pp12
TCTCTCCCAC CTGAACCCCC ACTCTCGACC CCGCCCCAGT CCTCCCTCTA TCCGGCTCTC 1020
                             ┌─StuI─┐
ACTTCTCCTT TAAACACCAA ACCTAGGCCT CAAGTCCTTC CTGATAGCGG AGGACCACTC 1080

ATTGATCTAC TCACGGAGGA CCCTCCGCCT TACCGGGACC CAGGGCCACC CTCTCCTGAC 1140

GGGAACGGCG ATAGCGGAGA AGTGGCCCCT ACAGAAGGAG CCCCTGACCC TTCCCCAATG 1200

GTATCCCGCC TGCGGGGAAG AAAAGAACCC CCCGTGGCGG ATTCTACTAC CTCTCAGGCG 1260
p12─┬─►CAp30
TTCCCCCTTC GCCTGGGAGG GAATGGACAG TATCAATACT GGCCATTTTC CTCCTCTGAC 1320

CTCTATAACT GGAAAAATAA CAACCCCTCT TTCTCCGAGG ACCCAGCTAA ATTGACAGCT 1380

TTGATCGAGT CCGTTCTCCT TACTCATCAG CCCACTTGGG ATGACTGCCA ACAGCTATTA 1440
        ┌── Start FMS15 1447-1468 ──┐
GGGACCCTGC TGACGGGAGA AGAAAAACAG CGAGTGCTCC TAGAGGCCCG AAAGGCGGTT 1500
                           ┌─PvuII─┐
CGAGGGGAGG ACGGACGCCC AACTCAGCTG CCCAATGACA TTAATGATGC TTTTCCCTTG 1560
                     (1527) ─┘  N+B+
GAACGTCCCG ACTGGGACTA CAACACCCAA CGAGGTAGGA ACCACCTAGT CCACTATCGC 1620

CAGTTGCTCC TAGCGGGTCT CCAAAACGCG GGCAGAAGCC CCACCAATTT GGCCAAGGTA 1680

AAAGGGATAA CCCAGGGACC TAATGAGTCT CCCTCAGCCT TTTTAGAGAG ACTCAAGGAG 1740

GCCTATCGCA GATACACTCC TTATGACCCT GAGGACCCAG GGCAAGAAAC CAATGTGGCC 1800
```

FIG. 5B

```
ATGTCATTCA TCTGGCAGTC CGCCCCGGAT ATCGGGCGAA AGTTAGAGCG GTTAGAAGAT 1860
                                                     BglII
TTGAAGAGTA AGACCTTAGG AGACTTAGTG AGGGAAGCTG AAAAGATCTT TAATAAACGA 1920
GAAACCCCGG AAGAAAGAGA GGAACGTATT AGGAGAGAAA CAGAGGAAAA GGAAGAACGC 1980
CGTAGGGCAG AGGATGTGCA GAGAGAGAAG GAGAGGGACC GCAGAAGACA TAGAGAAATG 2040
      CAp30 ◄─┬─► NCp10
AGTAAGTTGC TGGCTACTGT CGTTAGCGGG CAGAGACAGG ATAGACAGGG AGGAGAGCGA 2100
AGGAGGCCCC AACTCGACCA CGACCAGTGT GCCTACTGCA AAGAAAGGG ACATTGGGCT 2160
AGAGATTGCC CCAAGAAGCC AAGAGGACCC CGGGGACCAC GACCCCAGGC CTCCCTCCTG 2220
         gag ◄─┬─► pol                                         ┌─►PR
ACCTTAGACG ATTAGGGAGG TCAGGGTCAG GAGCCCCCCC CTGAACCCAG GATAACCCTC 2280
> REFMLVCGD.POL
  REFMLVCGD.GAG <
AGAGTCGGGG GGCAACCCGT CACCTTCCTA GTGGATACTG GGCCCAACA CTCCGTGCTG 2340
ACCCAAAATC CTGGACCCCT AAGTGACAAG TCTGCCTGGG TCCAAGGGGC TACTGGAGGG 2400
AAGCGGTATC GCTGGACCAC GGATCGCCGA GTGCACCTAG CCACCGGTAA GGTCACCCAT 2460
TCTTTCCTCC ATGTACCAGA TTGCCCCTAT CCTCTGCTAG GAAGAGATTT GCTGACTAAA 2520
CTAAAAGCCC AAATTCACTT TGAGGGATCA GGAGCTCAGG TTGTGGGACC AATGGGACAG 2580
           PR ◄─┬─► RT
CCCCTGCAAG TGCTGACCCT AAACATAGAA GATGAGTATC GGCTACATGA GACCTCAAAA 2640
GGGCCAGATG TGCCTCTAGG GTCCACATGG CTCTCTGATT TTCCCCAGGC CTGGGCAGAA 2700
                                          BclI
ACCGGGGGCA TGGGGCTGGC CGTTCGCCAA GCTCCTCTGA TCATACCTCT GAAGGCAACC 2760
TCTACCCCCG TGTCCATAAA ACAATACCCC ATGTCACAAG AAGCCAGACT GGGGATCAAG 2820
                       EcoRI
CCCCACATAC AGAGACTGCT GGATCAGGGA ATTCTGGTAC CCTGCCAGTC CCCCTGGAAC 2880
ACGCCCCTGC TACCCGTTAA GAAACCGGGG ACTAATGATT ATAGGCCTGT CCAGGATCTG 2940
AGAGAAGTCA ACAAGCGGGT GGAAGACATC CACCCCACCG TGCCCAACCC TTACAACCTC 3000
TTGAGCGGGC TCCCACCGTC CCACCAGTGG TACACTGTGC TTGACTTAAA AGATGCTTTT 3060
TTCTGCCTGA GACTCCACCC CACCAGTCAG TCTCTCTTCG CCTTTGAGTG GAGAGATCCA 3120
GAGATGGGAA TCTCAGGACA ATTAACCTGG ACCAGACTCC CGCAGGGTTT CAAAAACAGT 3180
CCCACCCTGT TTGATGAAGC CCTGCACAGG GACCTCGCAG ACTTCCGGAT CCAGCACCCA 3240
GACCTGATTC TGCTCCAGTA TGTAGATGAC TTACTGCTGG CCGCCACTTC TGAGCTTGAC 3300
TGTCAACAAG GTACGCGGGC CCTGTTACAA ACCCTAGGGG ACCTCGGATA TCGGGCCTCG 3360
GCCAAGAAAG CCCAAATTTG CCAGAAACAG GTCAAGTATC TGGGGTATCT TCTAAAAGAG 3420
GGTCAGAGAT GGCTGACTGA GGCCAGAAAA GAGACTGTGA TGGGGCAGCC TACTCCGAAG 3480
ACCCCTCGAC AACTAAGGGA GTTCCTAGGG ACGGCAGGCT TCTGTCGCCT CTGGATCCCT 3540
GGGTTTGCAG AAATGGCAGC CCCCTTGTAC CCTCTCACCA AAACGGGGAC TCTGTTTGAG 3600
TGGGGCCCAG ACCAGCAAAA GGCCTACCAA GAGATCAAGC AGGCTCTCTT AACTGCCCCT 3660
```

FIG. 5C

```
GCCCTGGGAT  TGCCAGACTT  GACTAAGCCC  TTCGAACTTT  TTGTTGACGA  GAAGCAGGGC  3720
TACGCCAAAG  GTGTCCTAAC  GCAAAAACTG  GGGCCTTGGC  GTCGGCCGGT  GGCCTACCTG  3780
TCCAAAAAGC  TAGACCCAGT  GGCAGCTGGG  TGGCCCCCTT  GCCTACGGAT  GGTAGCAGCC  3840
ATCGCCGTTC  TGACCAAAGA  CGCTGGCAAG  CTCACCATGG  GACAGCCACT  AGTCATTCTG  3900
GCCCCCCATG  CAGTAGAGGC  ACTAGTTAAG  CAACCCCCTG  ATCGCTGGCT  CTCCAACGCC  3960
CGAATGACCC  ACTACCAGGC  TCTGCTTCTG  GACACGGACC  GAGTCCAGTT  CGGACCAATA  4020
GTGGCCCTAA  ACCCAGCTAC  GCTGCTCCCT  CTACCTGAGG  AGGGGCTGCA  ACATGACTGC  4080
CTTGACATCT  TGGCTGAAGC  CCACGGAACT  AGACCAGATC  TTACGGACCA  GCCTCTCCCA  4140
GACGCTGACC  ACACCTGGTA  CACAGATGGG  AGCAGCTTCC  TGCAAGAGGG  GCAGCGCAAG  4200
GCCGGAGCAG  CAGTAACCAC  CGAGACCGAG  GTAGTCTGGG  CCAAAGCACT  GCCAGCCGGG  4260
ACATCGGCCC  AAAGAGCTGA  GTTGATAGCG  CTCACCCAAG  CCTTAAAAAT  GGCAGAAGGT  4320
AAGAAGCTGA  ATGTTTACAC  CGATAGCCGT  TATGCTTTTG  CCACTGCCCA  TATTCACGGA  4380
GAAATATATA  GAAGGCGCGG  GTTGCTCACA  TCAGAAGGAA  AAGAAATCAA  AAATAAGGAC  4440
GAGATCTTGG  CCCTACTGAA  GGCTCTCTTC  CTGCCCAAAA  GACTTAGCAT  AATTCATTGC  4500
CCGGGACATC  AGAAGGGAAA  CCGCGCGGAG  GCAAGGGGCA  ACAGGATGGC  CGACCAAGCG  4560
GCCCGAGAAG  TAGCCACTAG  AGAAACTCCA  GAGACTTCCA  CACTTCTGAT  AGAAAATTCA  4620
GCCCCCTATA  CTCATGAACA  TTTTCACTAT  ACGGTGACTG  ACATAAAAGA  TCTGACTAAA  4680
CTAGGGGCCA  CTTATGACGA  TGCAAAGAAG  TGTTGGGTTT  ATCAGGGAAA  GCCTGTAATG  4740
CCTGATCAAT  TCACCTTTGA  ACTATTAGAT  TTTCTTCATC  AATTGACCCA  CCTCAGTTTC  4800
TCAAAAACAA  AGGCTCTTCT  AGAAAGGAAC  TACTGTCCTT  ATTACATGCT  GAACCGGGAT  4860
CGAACGCTCA  AAGACATCAC  TGAGACTTGC  CAAGCCTGTG  CACAGGTCAA  TGCCAGCAAG  4920
TCTGCCGTCA  AACAAGGGAC  TAGAGTTCGA  GGGCACCGAC  CCGGCACCCA  CTGGGAAATT  4980
GATTTCACTG  AGGTAAAACC  TGGCCTGTAT  GGGTATAAAT  ATCTTTTAGT  TTTCATAGAC  5040
ACTTTCTCTG  GATGGGTAGA  AGCTTTCCCA  ACCAAGAAAG  AAACTGCCAA  AGTTGTAACC  5100
AAGAAGCTAC  TAGAAGAAAT  CTTCCCCAGA  TTCGGCATGC  CACAGGTATT  GGGAACCGAC  5160
AATGGGCCTG  CCTTCGTCTC  CAAGGTAAGT  CAGACAGTAG  CCGATTTACT  GGGGGTTGAT  5220
TGGAAACTAC  ATTGTGCTTA  CAGACCCCAG  AGTTCAGGTC  AGGTAGAAAG  AATGAATAGG  5280
ACAATCAAGG  AGACTTTAAC  TAAATTGACG  CTTGCAACTG  GCTCTAGGGA  CTGGGTGCTC  5340
CTGCTTCCCC  TAGCCCTGTA  TCGAGCCCGC  AACACGCCGG  GCCCCATGG   TCTCACCCCA  5400
```

FIG. 5D

| | | | | | | |
|---|---|---|---|---|---|---|
| TATGAAATCT | TATATGGGGC | ACCCCCGCCC | CTTGTAAACT | TCCCTGATCC | TGACATGGCA | 5460 |
| AAGGTTACTC | ATAACCCCTC | TCTCCAAGCC | CATTTACAGG | CACTCTACCT | GGTCCAGCAC | 5520 |
| GAAGTCTGGA | GACCGTTGGC | GGCAGCTTAC | CAAGAACAAC | TGGACCGGCC | GGTAGTGCCT | 5580 |
| CACCCTTTCC | GAGTCGGTGA | CACAGTGTGG | GTCCGCAGAC | ACCAAACTAA | AAATCTAGAA | 5640 |
| CCCCGCTGGA | AAGGACCTTA | TACCGTCCTA | CTGACTACCC | CCACCGCTCT | CAAAGTGGAC | 5700 |
| GGCATTGCAG | CGTGGATCCA | CGCTGCCCAC | GTAAAGGCTG | CCGACACCAG | GATTGAGCCA | 5760 |
| CCATCGGAAT | CGACATGGCG | TGTTCAACGC | TCTCAAAATC | CCCTAAAGAT | AAGATTGACC | 5820 |
| | > REFMLVCGD.ENV | | | | | |
| CGCGGGACCT | CCTAATCCCC | TTAATTCTCT | TCCTGTCTCT | CAAAGGGGCC | AGATCCGCAG | 5880 |
| REFMLVCGD.POL < | | | | | | |
| CACCCGGCTC | CAGCCCTCAC | CAGGTCTACA | ACATTACCTG | GAAGTGACC | AATGGGGATC | 5940 |
| GGGAGACAGT | ATGGGCAATA | TCAGGCAACC | ACCCTCTGTG | GACTTGGTGG | CCAGTCCTCA | 6000 |
| CCCCAGATTT | GTGTATGTTA | GCTCTCAGTG | GGCCGCCCCA | CTGGGGGCTA | GAGTATCAGG | 6060 |
| CCCCCTATTC | CTCGCCCCCG | GGGCCCCCTT | GTTGCTCAGG | GAGCAGCGGG | AACGTTGCAG | 6120 |
| GCTGTGCCAG | AGACTGCAAC | GAGCCCTTGA | CCTCCCTCAC | CCCTCGGTGC | AACACTGCCT | 6180 |
| GGAACAGACT | TAAGCTGGAC | CAGGTAACTC | ATAAATCAAG | TGAGGGATTT | TATGTCTGCC | 6240 |
| CCGGGTCACA | TCGCCCCCGG | GAAGCCAAGT | CCTGTGGGGG | TCCAGACTCC | TTCTACTGTG | 6300 |
| CCTCTTGGGG | CTGCGAGACA | ACCGGTAGAG | TATACTGGAA | GCCCTCCTCT | TCTTGGGACT | 6360 |
| ACATCACAGT | AGACAACAAT | CTCACCTCTA | ACCAGGCTGT | TCAGGTATGC | AAAGACAATA | 6420 |
| AGTGGTGCAA | TCCCTTGGCT | ATCCGGTTTA | CAAACGCCGG | GAAACAGGTC | ACCTCATGGA | 6480 |
| CAACTGGACA | CTATTGGGGT | CTACGTCTTT | ATGTCTCTGG | ACAGGACCCA | GGGCTTACTT | 6540 |
| TCGGGATCCG | ACTCAGTTAT | CAAAATCTAG | GACCTCGGAT | CCCAATAGGA | CCAAACCCCG | 6600 |
| TCCTGGCAGA | CCAACTTTCG | TTCCCGCTAC | CTAATCCCCT | ACCCAAACCT | GCCAAGTCTC | 6660 |
| CCCCCGCCTC | TAGTTCGACT | CCCACATTGA | TTTCCCCGTC | CCCCACTCCC | ACTCAGCCCC | 6720 |
| CGCCAGCAGG | AACGGGAGAC | AGATTACTAA | ATCAGTACA | GGGAGCTTAC | CAGGCACTCA | 6780 |
| ACCTTACCAA | CCCTGATAAA | ACTCAAGAGT | GCTGGTTATG | CCTAGTGTCT | GGACCCCCT | 6840 |
| ATTACGAGGG | GGTTGCCGTC | CTAGGTACTT | ATTCCAACCA | TACCTCTGCC | CCAGCTAACT | 6900 |
| GCTCCGTGGC | CTCCCAACAC | AAGCTGACCC | TGTCCGAAGT | GACTGGACGG | GGACTCTGCA | 6960 |
| TAGGAACAGT | CCCAAAAACT | CACCAGGCCC | TGTGCAACAC | TACCCTTAAG | GCAGGCAAAG | 7020 |
| GGTCTTACTA | TCTAGTTGCC | CCCACAGGAA | CTATGTGGGC | ATGTAACACT | GGACTCACTC | 7080 |
| CATGCCTATC | TGCCACCGTG | CTTAATCGCA | CCACTGACTA | TTGCGTTCTC | GTGGAATTAT | 7140 |

FIG. 5E

```
GGCCCAGGGT CACCTACCAT CCTCCCAGTT ACGTCTATAG CCAGTTTGAA AAATCCCATA 7200
GACATAAAAG AGAACCAGTG TCCTTAACCT TGGCCTTATT ATTAGGTGGG CTAACTATGG 7260
GTGGCATCGC CGCGGGAGTA GGGACAGGAA CTACCGCCCT GGTCGCCACC CAGCAGTTTC 7320
AGCAGCTCCA TGCTGCCGTA CAAGATGATC TCAAAGAAGT CGAAAAGTCA ATTACTAACC 7380
TAGAAAAGTC TCTTACTTCG TTGTCTGAGG TTGTACTGCA GAATCGACGA GGCCTAGACC 7440
TGTTGTTCCT AAAAGAGGGA GGACTGTGTG CTGCCCTAAA AGAAGAATGT TGTTTCTATG 7500
CTGACCATAC AGGCCTAGTA AGAGATAGTA TGGCCAAATT AAGAGAGAGA CTCTCTCAGA 7560
GACAAAAACT ATTTGAGTCG AGCCAAGGAT GGTTCGAAGG ATGGTTTAAC AGATCCCCCT 7620
GGTTTACCAC GTTGATATCC ACCATCATGG GGCCTCTCAT TATACTCCTA CTAATTCTGC 7680
TTTTTGGACC CTGCATTCTT AATCGATTAG TTCAATTTGT TAAAGACAGG ATCTCAGTAG 7740
TCCAGGCTTT AGTCCTGACT CAACAATACC ACCAGCTAAA ACCACTAGAA TACGAGCCAC 7800
AATAAATAAA AGATTTTATT TAGTTTCCAG AAAAAGGGGG GAATGAAAGA CCCCACCAAA 7860
TTGCTTAGCC TGATAGCCGC AGTAACGCCA TTTTGCAAGG CATGGAAAAA TACCAAACCA 7920
         ├──────── LTR 81 ────────┤
AGAATAGAGA AGTTCAGATC AAGGGCGGGT ACACGAAAAC AGCTAACGTT GGGCCAAACA 7980
GGATATCTGC GGTGAGCAGT TTCGGCCCCG GCCCGGGGCC AAGAACAGAT GGTCACCGCG 8040
                                                         LTR +281
GTTCGGCCCC GGCCCGGGGC CAAGAACAGA TGGTCCCCAG ATATGGCCCA ACCCTCAGCA 8100
GTTTCTTAAG ACCCATCAGA TGTTTCCAGG CTCCCCCAAG GACCTGAAAT GACCCTGTGC 8160
                                U3◄──┬──►R
CTTATTTGAA TTAACCAATC AGCCTGCTTC TCGCTTCTGT TCGCGCGCTT CTGCTTCCCG 8220
AGCTCTATAA AAGAGCTCAC AACCCCTCAC TCGGCGCGCC AGTCCTCCGA TAGACTGAGT 8280
CGCCCGGGTA CCCGTGTATC CAATAAATCC TCTTGCTGTT GCA            8323
``` polylinker:
Bam HI: 2088
Xba I: 2094
Sal I: 2100
Pst I: 2106
Sph I: 2112 polylinker:
Bam HI : 2088
Xba I : 2094
Sal I : 2100
Pst I : 2106
Sph I : 2112

SEQUENCE LISTING

```
<160> NUMBER OF SEQ ID NOS: 16

<210> SEQ ID NO 1
<211> LENGTH: 2999
<212> TYPE: DNA
<213> ORGANISM: Viral DNA used for FOCH29

<400> SEQUENCE: 1
agtgaattcc gattagttca atttgttaaa gacaggatct cagtagtcca ggctttagtc      60
ctgactcaac aataccacca gctaaaacca ctagaatacg agccacaata aataaaagat     120
tttatttagt ttccagaaaa aggggggaat gaaagacccc accaaattgc ttagcctgat     180
agccgcagta acgccatttt gcaaggcatg gaaaaatacc aaaccaagaa tagagaagtt     240
cagatcaagg gcgggtacac gaaaacagct aacgttgggc caaacaggat atctgcggtg     300
agcagtttcg gccccggccc ggggccaaga acagatggtc accgcggttc ggccccggcc     360
cggggccaag aacagatggt ccccagatat ggcccaaccc tcagcagttt cttaagaccc     420
atcagatgtt tccaggctcc cccaaggacc tgaaatgacc ctgtgcctta tttgaattaa     480
ccaatcagcc tgcttctcgc ttctgttcgc gcgcttctgc ttcccgagct ctataaaga      540 gctcacaacc cctcactcgg cgccagtcct ccgatagact gagtcgcccg ggtacccgtg     600
tatccaataa atcctcttgc tgttgcatcc gactcgtggt ctcgctgttc cttgggaggg     660
tctcctcaga gtgattgact acccgtctcg ggggtctttc atttggggc tcgtccggga      720 tctggagacc cctgcccagg gaccaccgac ccaccaccgg gaggtaagct ggccagcaat     780
tgttctgtgt ctgtccattg tcctgtgtct ttgattgatt ttatgcgcct gtgtctgtac     840
tagttggccg actagattgg tatctggcgg atccgtggtg gaactgacga gttcgagaca     900
cccggccgca accctgggag acgtcccagg gacttcgggg gccattttg tggcccggcc      960 agagtccaac catcccgatc gtttggact ctttggtgca ccccccttag aggagggta     1020 tgtggttctg gtaggagaca gagggctaaa acggtttccg ccccgtctg agtttttgct     1080 ttcggtttgg aaccgaagcc gcgccgcgcg tcttgtctgc tgcagcatcg ttctgtgttg    1140
tctctgtttg actgttttc tgtatttgtc tgaaaacatg ggccaggctg ttaccacccc     1200
cttaagtttg acttagacc actggaagga tgtcgaacgg acagcccaca acctgtcggt     1260
agaggttaga aaaaggcgct gggttacatt ctgctctgca gaatggccaa ccttcaacgt    1320
cggatggcca cgagacggca cttttaaccc agacattatt acacaggtta agatcaaggt    1380
```

```
cttctcacct ggcccacatg gacatccgga tcaggtcccc tacatcgtga cctgggaagc   1440
tatagcagta gaccccctc cctgggtcag acccttcgtg caccctaaac ctcccctctc   1500
tcttccccct tcagccccct ctctcccacc tgaaccccca ctctcgaccc cgccccagtc   1560
ctccctctat ccggctctca cttctccttt aaacaccaaa cctaggcctc aagtccttcc   1620
tgatagcgga ggaccactca ttgatctact cacggaggac cctccgcctt accgggaccc   1680
agggccaccc tctcctgacg ggaacggcga tagcggagaa gtggcccta cagaaggagc   1740 ccctgaccct tccccaatgg tatcccgcct gcggggaaga aaagaaccccc ccgtggcgga   1800 ttctactacc tctcaggcgt tccccttcg cctgggaggg aatggacagt atcaatactg   1860
gccattttcc tcctctgacc tctataactg gaaaaataac aaccctctt tctccgagga   1920 cccagctaaa ttgacagctt tgatcgagtc cgttctcctt actcatcagc ccacttggga   1980
tgactgccaa cagctattag ggaccctgct gacgggagaa gaaaaacagc gagtgctcct   2040
agaggcccga aaggcggttc gaggggagga cggacgccca actcagggg atcctctaga   2100 gtcgacctgc aggcatgcaa gctcagatcc aattcgatta gttcaatttg ttaaagacag   2160
gatctcagta gtccaggctt tagtcctgac tcaacaatac caccagctaa aaccactaga   2220
atacgagcca caataaataa aagatttat ttagtttcca gaaaaggggg ggaatgaaag   2280
accccaccaa attgcttagc ctgatagccg cagtaacgcc attttgcaag gcatggaaaa   2340
ataccaaacc aagaatagag aagttcagat caagggcggg tacacgaaaa cagctaacgt   2400
tgggccaaac aggatatctg cggtgagcag tttcggcccc ggcccggggc caagaacaga   2460
tggtcaccgc ggtccggccc cggcccgggg ccaagaacag atggtcccca gatatggccc   2520
aaccctcagc agtttcttaa gacccatcag atgtttccag gctcccccaa ggacctgaaa   2580
tgaccctgtg ccttatttga attaaccaat cagcctgctt ctcgcttctg ttcgcgcgct   2640
tctgcttccc gagctctata aaagagctca caaccctca ctcggcgcca gtcctccgat   2700
agactgagtc gcccgggtac ccgtgtatcc aataaatcct cttgctgttg catccgactc   2760
gtggtctcgc tgttccttgg gagggtctcc tcagagtgat tgactaccg tctcggggt   2820 ctttcatttg ggggctcgtc cgggatctgg agaccctgc ccaggacca ccgacccacc   2880 accgggaggt aagctggcca gcaattgttc tgtgtctgtc cattgtcctg tgtctttgat   2940
tgattttatg cgcctgtgtc tgtactagtt ggccgactag attggtatct ggcggatct   2999
```

<210> SEQ ID NO 2
<211> LENGTH: 8323
<212> TYPE: DNA
<213> ORGANISM: Friend murine leukemia virus (F-MuLV)

<400> SEQUENCE: 2

```
gcgccagtcc tccgatagac tgagtcgccc gggtacccgt gtatccaata atcctcttg     60 ctgttgcatc cgactcgtgg tctcgctgtt ccttgggagg gtctcctcag agtgattgac    120
tacccgtctc gggggtcttt catttggggg ctcgtccggg atctggagac ccctgccag    180 ggaccaccga cccaccaccg ggaggtaagc tggccagcaa ttgttctgtg tctgtccatt    240
gtcctgtgtc tttgattgat tttatgcgcc tgtgtctgta ctagttggcc gactagattg    300
gtatctggcg gatccgtggt ggaactgacg agttcgagac accggccgc aaccctggga    360 gacgtcccag ggcttcgggg gccattttt gtgcccggc cagagtccaa ccatcccgat    420
cgttttggac tctttggtgc acccccctta gaggagggt atgtggttct ggtaggagac    480
```

-continued

```
agagggctaa aacggtttcc gccccgtct gagttttgc tttcggtttg gaaccgaagc    540
cgcgccgcgc gtcttgtctg ctgcagcatc gttctgtgtt gtctctgttt gactgttttt    600
ctgtatttgt ctgaaaacat gggccaggct gttaccaccc ccttaagttt gactttagac    660
cactggaagg atgtcgaacg acagcccac aacctgtcgg tagaggttag aaaaaggcgc    720
tgggttacat tctgctctgc agaatggcca accttcaacg tcggatggcc acgagacggc    780
acttttaacc cagacattat tacacaggtt aagatcaagg tcttctcacc tggcccacat    840
ggacatccgg atcaggtccc ctacatcgtg acctgggaag ctatagcagt agaccccccct    900
ccctgggtca gacccttcgt gcaccctaaa cctcccctct ctcttccccc ttcagcccccc    960
tctctcccac ctgaaccccc actctcgacc ccgcccagt cctccctcta ccggctctc    1020
acttctcctt taaacaccaa acctaggcct caagtccttc ctgatagcgg aggaccactc    1080
attgatctac tcacggagga ccctccgcct taccgggacc cagggccacc ctctcctgac    1140
gggaacggcg atagcggaga agtggcccct acagaaggag cccctgaccc ttccccaatg    1200
gtatcccgcc tgcggggaag aaaagaaccc ccgtggcgg attctactac ctctcaggcg    1260
ttccccttc gcctgggagg gaatggacag tatcaatact ggccattttc ctcctctgac    1320
ctctataact ggaaaataa caaccccctct ttctccgagg acccagctaa attgacagct    1380
ttgatcgagt ccgttctcct tactcatcag cccacttggg atgactgcca acagctatta    1440
gggaccctgc tgacgggaga agaaaaacag cgagtgctcc tagaggcccg aaaggcggtt    1500
cgaggggagg acgacgcccc aactcagctg cccaatgaca ttaatgatgc ttttcccttg    1560
gaacgtcccg actgggacta caacacccaa cgaggtagga accacctagt ccactatcgc    1620
cagttgctcc tagcgggtct ccaaaacgcg ggcagaagcc ccaccaattt ggccaaggta    1680
aaagggataa cccagggacc taatgagtct ccctcagcct ttttagagag actcaaggag    1740
gcctatcgca gatacactcc ttatgaccct gaggacccag ggcaagaaac caatgtggcc    1800
atgtcattca tctggcagtc cgccccggat atcgggcgaa agttagagcg gttagaagat    1860
ttgaagagta agaccttagg agacttagtg agggaagctg aaaagatctt taataaacga    1920
gaaaccccgg aagaaagaga ggaacgtatt aggagagaaa cagaggaaaa ggaagaacgc    1980
cgtagggcag aggatgtgca gagagagaag gagagggacc gcagaagaca tagagaaatg    2040
agtaagttgc tggctactgt cgttagcggg cagagacagg atagacaggg aggagagcga    2100
aggaggcccc aactcgacca cgaccagtgt gcctactgca agaaaaaggg acattgggct    2160
agagattgcc ccaagaagcc aagaggaccc cggggaccac gaccccaggc ctccctcctg    2220
accttagacg attagggagg tcagggtcag gagcccccccc ctgaacccag gataaccctc    2280
agagtcgggg ggcaacccgt caccttccta gtggatactg gggcccaaca ctccgtgctg    2340
acccaaaatc ctgacccct aagtgacaag tctgcctggg tccaagggc tactggaggg    2400
aagcggtatc gctggaccac ggatcgccga gtgcacctag ccaccggtaa ggtcacccat    2460
tctttcctcc atgtaccaga ttgcccctat cctctgctag gaagagattt gctgactaaa    2520
ctaaaagccc aaattcactt tgagggatca ggagctcagg ttgtgggacc aatgggacag    2580
cccctgcaag tgctgaccct aaacatagaa gatgagtatc ggctacatga gacctcaaaa    2640
gggccagatg tgcctctagg gtccacatgg ctctctgatt ttccccaggc ctgggcagaa    2700
accgggggca tggggctggc cgttcgccaa gctcctctga tcatacctct gaaggcaacc    2760
tctacccccg tgtccataaa acaataccccc atgtcacaag aagccagact ggggatcaag    2820
ccccacatac agagactgct ggatcaggga attctggtac cctgccagtc ccctggaac    2880
```

```
acgccctgc tacccgttaa gaaaccgggg actaatgatt ataggcctgt ccaggatctg    2940
agagaagtca acaagcgggt ggaagacatc cacccaccg tgcccaaccc ttacaacctc    3000
ttgagcgggc tcccaccgtc ccaccagtgg tacactgtgc ttgacttaaa agatgctttt    3060
ttctgcctga gactccaccc caccagtcag tctctcttcg cctttgagtg gagagatcca    3120
gagatgggaa tctcaggaca attaacctgg accagactcc cgcagggttt caaaaacagt    3180
cccaccctgt ttgatgaagc cctgcacagg gacctcgcag acttccggat ccagcaccca    3240
gacctgattc tgctccagta tgtagatgac ttactgctgg ccgccacttc tgagcttgac    3300
tgtcaacaag gtacgcgggc cctgttacaa accctagggg acctcggata tcgggcctcg    3360
gccaagaaag cccaaatttg ccagaaacag gtcaagtatc tggggtatct tctaaaagag    3420
ggtcagagat ggctgactga ggccagaaaa gagactgtga tggggcagcc tactccgaag    3480
acccctcgac aactaaggga gttcctaggg acggcaggct tctgtcgcct ctggatccct    3540
gggtttgcag aaatggcagc cccttgtac cctctcacca aaacgggac tctgtttgag    3600 tggggcccag accagcaaaa ggcctaccaa gagatcaagc aggctctctt aactgccct    3660 gccctgggat tgccagactt gactaagccc ttcgaacttt ttgttgacga aagcagggc    3720 tacgccaaag tgtcctaac gcaaaaactg gggccttggc gtcggccggt ggcctacctg    3780
tccaaaaagc tagacccagt ggcagctggg tggccccctt gcctacggat ggtagcagcc    3840
atcgccgttc tgaccaaaga cgctggcaag ctcaccatgg gacagccact agtcattctg    3900
gccccccatg cagtagaggc actagttaag caaccccctg atcgctggct ctccaacgcc    3960
cgaatgaccc actaccaggc tctgcttctg gacacggacc gagtcccagtt cggaccaata    4020 gtggccctaa acccagctac gctgctccct ctacctgagg aggggctgca acatgactgc    4080
cttgacatct tggctgaagc ccacggaact agaccagatc ttacgaccca gcctctccca    4140
gacgctgacc acacctggta cacagatggg agcagcttcc tgcaagaggg gcagcgcaag    4200
gccggagcag cagtaaccac cgagaccgag gtagtctggg ccaaagcact gccagccggg    4260
acatcggccc aaagagctga gttgatagcg ctcacccaag ccttaaaaat ggcagaaggt    4320
aagaagctga atgtttacac cgatagccgt tatgcttttg ccactgccca tattcacgga    4380
gaaatatata gaaggcgcgg gttgctcaca tcagaaggaa aagaaatcaa aaataaggac    4440
gagatcttgg ccctactgaa ggctctcttc ctgcccaaaa gacttagcat aattcattgc    4500
ccgggacatc agaagggaaa ccgcgcggag gcaagggca acaggatggc cgaccaagcg    4560
gcccgagaag tagccactag agaaactcca gagacttcca cacttctgat agaaaattca    4620 gcccctata ctcatgaaca ttttcactat acggtgactg acataaaaga tctgactaaa    4680
ctaggggcca cttatgacga tgcaaagaag tgttgggttt atcagggaaa gcctgtaatg    4740
cctgatcaat tcacctttga actattagat tttcttcatc aattgaccca cctcagtttc    4800
tcaaaaacaa aggctcttct agaaaggaac tactgtccctt attacatgct gaaccgggat    4860
cgaacgctca aagacatcac tgagacttgc caagcctgtg cacaggtcaa tgccagcaag    4920
tctgccgtca acaagggac tagagttcga gggcaccgac ccggcaccca ctgggaaatt    4980
gatttcactg aggtaaaacc tggcctgtat gggtataaat atctttagt tttcatagac    5040 actttctctg gatgggtaga agctttccca accaagaaag aaactgccaa agttgtaacc    5100
aagaagctac tagaagaaat cttcccagat ttcggcatgc acaggtatt gggaaccgac    5160 aatgggcctg ccttcgtctc caaggtaagt cagacagtag ccgatttact gggggttgat    5220
```

-continued

```
tggaaactac attgtgctta cagaccccag agttcaggtc aggtagaaag aatgaatagg      5280
acaatcaagg agactttaac taaattgacg cttgcaactg gctctaggga ctgggtgctc      5340
ctgcttcccc tagccctgta tcgagcccgc aacacgccgg cccccatgg tctcacccca      5400 tatgaaatct tatatggggc accccgccc cttgtaaact tccctgatcc tgacatggca      5460
aaggttactc ataaccccct ctccaagcc catttacagg cactctacct ggtccagcac      5520
gaagtctgga gaccgttggc ggcagcttac caagaacaac tggaccggcc ggtagtgcct      5580 cacccttttcc gagtcggtga cacagtgtgg gtccgcagac accaaactaa aaatctagaa     5640
ccccgctgga aaggaccttta taccgtccta ctgactaccc ccaccgctct caaagtggac     5700
ggcattgcag cgtggatcca cgctgcccac gtaaaggctg ccgacaccag gattgagcca     5760
ccatcggaat cgacatggcg tgttcaacgc tctcaaaatc ccctaaagat aagattgacc     5820
cgcgggacct cctaatcccc ttaattctct tcctgtctct caaagggggcc agatccgcag    5880 cacccggctc cagccctcac caggtctaca acattacctg ggaagtgacc aatggggatc     5940
gggagacagt atgggcaata tcaggcaacc accctctgtg gacttggtgg ccagtcctca     6000
ccccagattt gtgtatgtta gctctcagtg ggccgcccca ctggggggcta gagtatcagg    6060 cccctattc ctcgcccccg gggccccctt gttgctcagg gagcagcggg aacgttgcag      6120
gctgtgccag agactgcaac gagcccttga cctccctcac ccctcggtgc aacactgcct    6180
ggaacagact taagctggac caggtaactc ataaatcaag tgagggattt tatgtctgcc    6240
ccgggtcaca tcgcccccgg gaagccaagt cctgtggggg tccagactcc ttctactgtg    6300
cctcttgggg ctgcgagaca accggtagag tatactggaa gccctcctct tcttgggact    6360
acatcacagt agacaacaat ctcacctcta accaggctgt tcaggtatgc aaagacaata    6420
agtggtgcaa tcccttggct atccggttta caaacgccgg gaaacaggtc acctcatgga    6480
caactggaca ctattggggt ctacgtcttt atgtctctgg acaggaccca gggcttactt    6540
tcgggatccg actcagttat caaaatctag gacctcggat cccaatagga ccaaaccccg    6600
tcctggcaga ccaactttcg ttcccgctac ctaatcccct acccaaacct gccaagtctc    6660
cccccgcctc tagttcgact cccacattga tttccccgtc cccactccc actcagcccc      6720 cgccagcagg aacgggagac agattactaa atctagtaca gggagcttac caggcactca    6780
accttaccaa ccctgataaa actcaagagt gctggttatg cctagtgtct ggacccccct     6840
attacgaggg ggttgccgtc ctaggtactt attccaacca tacctctgcc ccagctaact    6900
gctccgtggc ctcccaacac aagctgaccc tgtccgaagt gactggacgg ggactctgca    6960
taggaacagt cccaaaaact caccaggccc tgtgcaacac tacccttaag gcaggcaaag    7020
ggtcttacta tctagttgcc cccacaggaa ctatgtgggc atgtaacact ggactcactc    7080
catgcctatc tgccaccgtg cttaatcgca ccactgacta ttgcgttctc gtggaattat    7140
ggcccagggt cacctaccat cctcccagtt acgtctatag ccagtttgaa aaatcccata    7200
gacataaaag agaaccagtg tccttaacct tggccttatt attaggtggg ctaactatgg    7260
gtggcatcgc cgcgggagta gggacaggaa ctaccgccct ggtcgccacc cagcagtttc    7320
agcagctcca tgctgccgta caagatgatc tcaaagaagt cgaaaagtca attactaacc    7380
tagaaaagtc tcttacttcg ttgtctgagg ttgtactgca gaatcgacga ggcctagacc    7440
tgttgttcct aaaagaggga ggactgtgtg ctgccctaaa agaagaatgt tgtttctatg    7500
ctgaccatac aggcctagta agagatagta tggccaaatt aagagagaga ctctctcaga    7560
gacaaaaact atttgagtcg agccaaggat ggttcgaagg atggtttaac agatccccct    7620
```

-continued

```
ggtttaccac gttgatatcc accatcatgg ggcctctcat tatactccta ctaattctgc    7680
tttttggacc ctgcattctt aatcgattag ttcaatttgt taaagacagg atctcagtag    7740
tccaggcttt agtcctgact caacaatacc accagctaaa accactagaa tacgagccac    7800
aataaataaa agattttatt tagtttccag aaaaaggggg gaatgaaaga ccccaccaaa    7860
ttgcttagcc tgatagccgc agtaacgcca ttttgcaagg catggaaaaa taccaaacca    7920
agaatagaga agttcagatc aagggcgggt acacgaaaac agctaacgtt gggccaaaca    7980
ggatatctgc ggtgagcagt ttcggccccg gcccggggcc aagaacagat ggtcaccgcg    8040
gttcggcccc ggcccgggc caagaacaga tggtccccag atatggccca accctcagca    8100
gtttcttaag acccatcaga tgtttccagg ctcccccaag gacctgaaat gaccctgtgc    8160
cttatttgaa ttaaccaatc agcctgcttc tcgcttctgt tcgcgcgctt ctgcttcccg    8220
agctctataa aagagctcac aaccccctcac tcggcgcgcc agtcctccga tagactgagt    8280
cgcccgggta cccgtgtatc caataaatcc tcttgctgtt gca                       8323
```

<210> SEQ ID NO 3
<211> LENGTH: 22
<212> TYPE: DNA
<213> ORGANISM: Primer

<400> SEQUENCE: 3
ctgctgacgg gagaagaaaa ac           22

<210> SEQ ID NO 4
<211> LENGTH: 20
<212> TYPE: DNA
<213> ORGANISM: Primer

<400> SEQUENCE: 4
cccgctcaga agaactcgtc              20

<210> SEQ ID NO 5
<211> LENGTH: 20
<212> TYPE: DNA
<213> ORGANISM: Primer

<400> SEQUENCE: 5
gacgagttct tctgagcggg              20

<210> SEQ ID NO 6
<211> LENGTH: 22
<212> TYPE: DNA
<213> ORGANISM: Primer

<400> SEQUENCE: 6
gatctgaact tctctattct tg           22

<210> SEQ ID NO 7
<211> LENGTH: 24
<212> TYPE: DNA
<213> ORGANISM: Primer

<400> SEQUENCE: 7
cgactcctgg agcccgtcag tatc         24

<210> SEQ ID NO 8
<211> LENGTH: 23
<212> TYPE: DNA

<213> ORGANISM: Primer

<400> SEQUENCE: 8
cagcgagacc acgagtcgga tgc                                    23

<210> SEQ ID NO 9
<211> LENGTH: 25
<212> TYPE: DNA
<213> ORGANISM: Oligonucleotide

<400> SEQUENCE: 9
aattcaatga agacccccaa attgc                                  25

<210> SEQ ID NO 10
<211> LENGTH: 27
<212> TYPE: DNA
<213> ORGANISM: Oligonucleotide

<400> SEQUENCE: 10
taagcaattc ggtgggtct ttcattg                                 27

<210> SEQ ID NO 11
<211> LENGTH: 2079
<212> TYPE: DNA
<213> ORGANISM: Viral DNA used for FOCH29

<400> SEQUENCE: 11

```
tccgattagt tcaatttgtt aaagacagga tctcagtagt ccaggcttta gtcctgactc     60
aacaatacca ccagctaaaa ccactagaat acgagccaca ataaataaaa gattttattt    120
agtttccaga aaaggggggg aatgaaagac cccaccaaat tgcttagcct gatagccgca    180
gtaacgccat tttgcaaggc atggaaaaat accaaaccaa gaatagagaa gttcagatca    240
agggcgggta cacgaaaaca gctaacgttg gccaaacag gatatctgcg gtgagcagtt    300
tcggccccgg cccggggcca agaacagatg gtcaccgcgg tcggccccg gcccggggcc     360
aagaacagat ggtccccaga tatggcccaa ccctcagcag tttcttaaga cccatcagat    420
gtttccaggc tcccccaagg acctgaaatg accctgtgcc ttatttgaat taaccaatca    480
gcctgcttct cgcttctgtt cgcgcgcttc tgcttcccga gctctataaa agagctcaca    540
accctcact cggcgccagt cctccgatag actgagtcgc ccgggtaccc gtgtatccaa     600
taaatcctct tgctgttgca tccgactcgt ggtctgctg ttccttggga gggtctcctc     660
agagtgattg actacccgtc tcggggtct ttcatttggg ggctcgtccg ggatctggag     720
acccctgccc aggaccacc gacccaccac cggaggtaa gctggccagc aattgttctg     780
tgtctgtcca ttgtcctgtg tctttgattg attttatgcg cctgtgtctg tactagttgg     840
ccgactagat tggtatctgg cggatccgtg gtggaactga cgagttcgag acacccggcc     900
gcaaccctgg gagacgtccc agggacttcg ggggccattt ttgtggcccg gccagagtcc     960
aaccatcccg atcgtttggg actctttggt gcacccccct tagaggaggg gtatgtggtt   1020
ctggtaggag acagagggct aaaacggttt ccgccccgt ctgagttttt gctttcggtt    1080
tggaaccgaa gccgcgccgc gcgtcttgtc tgctgcagca tcgttctgtg ttgtctctgt    1140
ttgactgttt ttctgtattt gtctgaaaac atgggccagg ctgttaccac ccccttaagt   1200
ttgactttag accactggaa ggatgtcgaa cggacagccc acaacctgtc ggtagaggtt   1260
agaaaaaggc gctgggttac attctgctct gcagaatggc caaccttcaa cgtcggatgg   1320
ccacgagacg gcactttaa cccagacatt attacacagg ttaagatcaa ggtcttctca   1380
```

-continued

```
cctggcccac atggacatcc ggatcaggtc ccctacatcg tgacctggga agctatagca    1440
gtagaccccc ctccctgggt cagacccttc gtgcacccta aacctcccct ctctcttccc    1500
ccttcagccc cctctctccc acctgaaccc ccactctcga ccccgcccca gtcctccctc    1560
tatccggctc tcacttctcc tttaaacacc aaacctaggc ctcaagtcct tcctgatagc    1620
ggaggaccac tcattgatct actcacggag acccctccgc cttaccggga cccagggcca    1680
ccctctcctg acgggaacgg cgatagcgga gaagtggccc ctacagaagg agcccctgac    1740
ccttccccaa tggtatcccg cctgcgggga agaaaagaac ccccgtggc ggattctact     1800 acctctcagg cgttcccccT tcgcctggga gggaatggac agtatcaata ctggccattt    1860
tcctcctctg acctctataa ctggaaaaat aacaacccct ctttctccga ggacccagct    1920
aaattgacag ctttgatcga gtccgttctc cttactcatc agcccacttg ggatgactgc    1980
caacagctat tagggaccct gctgacggga aagaaaaac agcgagtgct cctagaggcc     2040
cgaaaggcgg ttcgagggga ggacggacgc ccaactcag                            2079
```

<210> SEQ ID NO 12
<211> LENGTH: 1975
<212> TYPE: DNA
<213> ORGANISM: Viral DNA used for FOCH29

<400> SEQUENCE: 12

```
ataaaagatt ttatttagtt tccagaaaaa gggggaatg aaagacccca ccaaattgct      60
tagcctgata gccgcagtaa cgccattttg caaggcatgg aaaaatacca aaccaagaat    120
agagaagttc agatcaaggg cgggtacacg aaaacagcta acgttgggcc aaacaggata    180
tctgcggtga gcagtttcgg ccccggcccg gggccaagaa cagatggtca ccgcggttcg    240
gccccggccc ggggccaaga acagatggtc cccagatatg gcccaaccct cagcagtttc    300
ttaagaccca tcagatgttt ccaggctccc caaggacct gaaatgaccc tgtgccttat    360
ttgaattaac caatcagcct gcttctcgct tctgttcgcg cgcttctgct tcccgagctc    420 tataaagag ctcacaaccc ctcactcggc gccagtcctc cgatagactg agtcgcccgg     480
gtacccgtgt atccaataaa tcctcttgct gttgcatccg actcgtggtc tcgctgttcc    540
ttgggagggt ctcctcagag tgattgacta cccgtctcgg gggtctttca tttgggggct    600
cgtccgggat ctggagaccc ctgcccaggg accaccgacc caccaccggg aggtaagctg    660
gccagcaatt gttctgtgtc tgtccattgt cctgtgtctt tgattgattt tatgcgcctg    720
tgtctgtact agttggccga ctagattggt atctggcgga tccgtggtgg aactgacgag    780
ttcgagacac ccggccgcaa ccctgggaga cgtcccaggg acttcggggg ccattttgt     840 ggcccggcca gagtccaacc atcccgatcg ttttggactc tttggtgcac cccccttaga    900 ggagggtat gtggttctgg taggagacag agggctaaaa cggtttccgc cccgtctga     960 gttttttgctt tcggtttgga accgaagccg cgccgcgcgt cttgtctgct gcagcatcgt    1020
tctgtgttgt ctctgtttga ctgttttttct gtatttgtct gaaacatgg gccaggctgt    1080 taccacccc ttaagtttga ctttagacca ctggaaggat gtcgaacgga cagcccacaa    1140
cctgtcggta gaggttagaa aaaggcgctg ggttacattc tgctctgcag aatggccaac    1200
cttcaacgtc ggatggccac gagacggcac ttttaaccca gacattatta cacaggttaa    1260
gatcaaggtc ttctcacctg gcccacatgg acatccggat caggtcccct acatcgtgac    1320
ctgggaagct atagcagtag accccctcc ctgggtcaga cccttcgtgc accctaaacc     1380
```

-continued

```
tcccctctct cttcccctt cagccccctc tctcccacct gaaccccac tctcgacccc      1440 gccccagtcc tccctctatc cggctctcac ttctccttta acaccaaac ctaggcctca      1500 agtccttcct gatagcggag gaccactcat tgatctactc acggaggacc ctccgcctta     1560
ccgggaccca gggccaccct ctcctgacgg gaacggcgat agcggagaag tggcccctac     1620
agaaggagcc cctgacccct ccccaatggt atcccgcctg cggggaagaa aagaaccccc     1680
cgtggcggat tctactacct ctcaggcgtt ccccttcgc ctgggaggga atggacagta      1740
tcaatactgg ccattttcct cctctgacct ctataactgg aaaaataaca cccctctttt    1800
ctccgaggac ccagctaaat tgacagcttt gatcgagtcc gttctcctta ctcatcagcc    1860
cacttgggat gactgccaac agctattagg gaccctgctg acgggagaag aaaaacagcg    1920
agtgctccta gaggcccgaa aggcggttcg aggggaggac ggacgcccaa ctcag         1975
```

<210> SEQ ID NO 13
<211> LENGTH: 862
<212> TYPE: DNA
<213> ORGANISM: Viral DNA used for FOCH29

<400> SEQUENCE: 13

```
tccgattagt tcaatttgtt aaagacagga tctcagtagt ccaggcttta gtcctgactc      60
aacaatacca ccagctaaaa ccactagaat acgagccaca ataaataaaa gattttattt    120
agtttccaga aaaagggggg aatgaaagac cccaccaaat tgcttagcct gatagccgca    180
gtaacgccat tttgcaaggc atggaaaaat accaaaccaa gaatagagaa gttcagatca    240
agggcgggta cacgaaaaca gctaacgttg ggccaaacag gatatctgcg gtgagcagtt    300
tcggccccgg cccggggcca agaacagatg gtcaccgcgg ttcggccccg gcccggggcc    360
aagaacagat ggtccccaga tatggcccaa ccctcagcag tttcttaaga cccatcagat    420
gtttccaggc tccccaagg acctgaaatg accctgtgcc ttatttgaat taaccaatca     480
gcctgcttct cgcttctgtt cgcgcgcttc tgcttcccga gctctataaa agagctcaca    540
acccctcact cggcgccagt cctccgatag actgagtcgc ccgggtaccc gtgtatccaa    600
taaatcctct tgctgttgca tccgactcgt ggtctcgctg ttccttggga gggtctcctc    660
agagtgattg actaccgtc tcgggggtct ttcatttggg ggctcgtccg ggatctggag    720 accctgccc agggaccacc gacccaccac cgggaggtaa gctggccagc aattgttctg    780
tgtctgtcca ttgtcctgtg tctttgattg attttatgcg cctgtgtctg tactagttgg    840
ccgactagat tggtatctgg cg                                            862
```

<210> SEQ ID NO 14
<211> LENGTH: 1617
<212> TYPE: DNA
<213> ORGANISM: Friend murine leukemia virus (F-MuLV)

<400> SEQUENCE: 14

```
atgggccagg ctgttaccac cccccttaagt ttgactttag accactggaa ggatgtcgaa     60
cggacagccc acaacctgtc ggtagaggtt agaaaaaggc gctggttac attctgctct    120 gcagaatggc caaccttcaa cgtcggatgg ccacagacg gcactttttaa cccagacatt    180 attacacagg ttaagatcaa ggtcttctca cctggcccac atggacatcc ggatcaggtc    240
ccctacatcg tgacctggga agctatagca gtagaccccc ctccctgggt cagacccttc   300 gtgcaccta aacctcccct ctctcttccc ccttcagccc cctctctccc acctgaaccc    360
ccactctcga ccccgcccca gtcctccctc tatccggctc tcacttctcc tttaaacacc    420
```

```
aaacctaggc ctcaagtcct tcctgatagc ggaggaccac tcattgatct actcacggag      480
gaccctccgc cttaccggga cccagggcca ccctctcctg acgggaacgg cgatagcgga      540
gaagtggccc ctacagaagg agccctgac ccttccccaa tggtatcccg cctgcgggga      600
agaaaagaac ccccgtggc ggattctact acctctcagg cgttcccct tcgcctggga      660 gggaatggac agtatcaata ctggccattt tcctcctctg acctctataa ctggaaaaat      720
aacaacccct ctttctccga ggacccagct aaattgacag ctttgatcga gtccgttctc      780
cttactcatc agcccacttg ggatgactgc aacagctat tagggaccct gctgacggga      840
gaagaaaaac agcgagtgct cctagaggcc cgaaaggcgg ttcgagggga ggacggacgc      900
ccaactcagc tgcccaatga cattaatgat gcttttccct ggaacgtcc cgactgggac      960 tacaacaccc aacgaggtag gaaccaccta gtccactatc gccagttgct cctagcgggt     1020
ctccaaaacg cggggcagaag cccccaccaat ttggccaagg taaagggat aacccaggga     1080 cctaatgagt ctccctcagc cttttagag agactcaagg aggcctatcg cagatacact     1140
ccttatgacc ctgaggaccc aggcaagaa accaatgtgg ccatgtcatt catctggcag     1200
tccgccccgg atatcgggcg aaagttagag cggttagaag atttgaagag taagaccta      1260 ggagacttag tgagggaagc tgaaaagatc tttaataaac gagaaccccc ggaagaaga     1320 gaggaacgta ttaggagaga aacagaggaa aaggaagaac gccgtagggc agaggatgtg     1380
cagagagaga aggagaggga ccgcagaaga catagagaaa tgagtaagtt gctggctact     1440
gtcgttagcg ggcagagaca ggatagacag ggaggagagc gaaggaggcc ccaactcgac     1500
cacgaccagt gtgcctactg caaagaaaag ggacattggg ctagagattg ccccaagaag     1560
ccaagaggac cccggggacc acgaccccag gcctccctcc tgaccttaga cgattag        1617
```

<210> SEQ ID NO 15
<211> LENGTH: 909
<212> TYPE: DNA
<213> ORGANISM: Friend murine leukemia virus (F-MuLV)

<400> SEQUENCE: 15

```
atgggccagg ctgttaccac ccccttaagt ttgactttag accactggaa ggatgtcgaa       60
cggacagccc acaacctgtc ggtagaggtt agaaaaggc gctgggttac attctgctct      120
gcagaatggc caaccttcaa cgtcggatgg ccacgagacg gcactttaa cccagacatt      180 attacacagg ttaagatcaa ggtcttctca cctggcccac atggacatcc ggatcaggtc      240
ccctacatcg tgacctggga agctatagca gtagaccccc ctccctgggt cagacccttc      300
gtgcacccta aacctcccct ctctcttccc ccttcagccc cctctctccc acctgaaccc      360
ccactctcga ccccgcccca gtcctccctc tatccggctc tcacttctcc tttaaacacc      420
aaacctaggc ctcaagtcct tcctgatagc ggaggaccac tcattgatct actcacggag      480
gaccctccgc cttaccggga cccagggcca ccctctcctg acgggaacgg cgatagcgga      540
gaagtggccc ctacagaagg agccctgac ccttccccaa tggtatcccg cctgcgggga      600
agaaaagaac ccccgtggc ggattctact acctctcagg cgttcccct tcgcctggga      660 gggaatggac agtatcaata ctggccattt tcctcctctg acctctataa ctggaaaaat      720
aacaacccct ctttctccga ggacccagct aaattgacag ctttgatcga gtccgttctc      780
cttactcatc agcccacttg ggatgactgc aacagctat tagggaccct gctgacggga      840
gaagaaaaac agcgagtgct cctagaggcc cgaaaggcgg ttcgagggga ggacggacgc      900
```

-continued

```
ccaactcag                                                             909

<210> SEQ ID NO 16
<211> LENGTH: 413
<212> TYPE: DNA
<213> ORGANISM: Friend murine leukemia virus (F-MuLV)

<400> SEQUENCE: 16
atgggccagg ctgttaccac ccccttaagt ttgactttag accactggaa ggatgtcgaa      60
cggacagccc acaacctgtc ggtagaggtt agaaaaaggc gctgggttac attctgctct     120
gcagaatggc caaccttcaa cgtcggatgg ccacgagacg gcacttttaa cccagacatt     180
attacacagg ttaagatcaa ggtcttctca cctggcccac atggacatcc ggatcaggtc     240
ccctacatcg tgacctggga agctatagca gtagacccc  ctccctgggt cagacccttc     300 gtgcaccta  aacctcccct ctctcttccc ccttcagccc cctctctccc acctgaaccc     360
ccactctcga ccccgcccca gtcctccctc tatccggctc tcacttctcc ttt            413
```

RETROVIRAL VECTOR FOR THE TRANSFER AND EXPRESSION OF GENES FOR THERAPEUTIC PURPOSES IN EUKARYOTIC CELLS

This application is a Continuation application of U.S. Ser. No. 08/270,662 filed Jun. 30, 1994, now abandoned.

The object of the invention is novel retroviral vectors, particularly for the transfer and expression of genes in eukaryotic cells. In this respect the invention proposes vectors particularly suitable for use in the transfer of genes for clinical therapeutic, prophylactic or diagnostic purposes.

The rapid development of molecular genetics has led to the identification of an increasing number of molecular abnormalities responsible for human diseases. Within the function unit constituted by the gene regions responsible for the expression of a biological signal and its regulation lie side by side. Each of these regions is liable to be the seat of pathological changes leading to a qualitative or quantitative abnormality of synthesis. The detection of these abnormalities allows screening for them but the major objective remains therapeutic.

The transfer of genes for therapeutic purposes or somatic "gene therapy" consists of inserting a "repairer" gene in the somatic cells of a constituted organism in order to compensate for the dysfunction of an endogenous gene; or even to add a novel function for a therapeutic purpose. The resulting genetic change is likely to be transmitted to the daughter cells of the manipulated cell but it will not be inherited. The normal counterpart of impaired DNA sequences is thus transformed into a medicine.

The field of gene therapy is today being very actively developed and combines clinical assays (for still very small patient populations) with very fundamental research work in to matters such as the modes of gene expression or the vectorization of the therapeutic nucleic acid sequences. The vectors presently used are derived either from inactivated viruses, such as retroviruses or adenoviruses, or macromolecular complexes. The retroviruses are more suitable for use in a target tissue comprising a contingent of stem cells capable of being manipulated ex vivo on the other hand, when the target tissue is constituted of terminally differentiated cells or intimately enmeshed in an organ whose architectural constraints have major functional consequences, such as the lung, the transfer of genes must be performed in vivo, for example by means of adenoviruses. Gene therapy finds applications in diseases as diverse as hereditary diseases due to the alteration of a single gene, such as Duchenne's myopathy, lysosomal diseases, mucoviscidosis or acquired diseases such as AIDS, cancers, thrombo-embolic disease or degenerative neurological diseases, constitutional hematological diseases.

Nonetheless, although the potential applications of gene transfer are extraordinarily large, the therapeutic developments of this approach and its appropriateness still come up against technological difficulties.

In this connection, the development of retroviral vectors more efficacious than the existing tools constitute a major objective. In fact, the retroviral vectors have demonstrated their efficacy in systems in which the target cells of the transfer are classically the subject of mitoses and ideally involve a contingent of stem cells; but the limitations are linked essentially to inadequate infectivity of the viruses used and/or a too moderate level of transcription. For this purpose useful vectors may be selected by considering in particular their infective titer.

The object of the invention is to propose more efficient vectors than those existing, most of which are presently derived from the backbone of the Moloney murine leukemia virus.

The invention is based on work performed starting from a particularly virulent strain of the Friend virus. The isolate I-5 of the ecotropic Friend murine leukemia virus was obtained from long-term bone marrow cultures infected by the Friend virus complex which induces polycythemia (FV-P) (Mathieu-Mahul et al., 1982). The FB29 strain of F-MuLV derived from the isolate I-5 (Sitbon et al., 1986) is responsible for cytolytic and leukemogenic effects on erythroid cells, leading to severe early hemolytic anemia followed by late erythroleukemia in susceptible mice inoculated at birth. The regions responsible for the erythroleukemia were localized in the U3 region of the viral LTR (Sitbon et al., 1986; Sitbon et al., 1991). The principal determinant of the hemolytic anemia seems to depend on specific envelop sequences of the FB29 strain; its severity may be affected by three distinct regions, including a structural segment of the envelope, enhancer sequences of transcription localized in the U3 region and, finally, sequences of the U5-gag-pol regions (Sitbon et al., 1990).

Furthermore, electron microscopical analyses of the viral particles have confirmed a significantly higher packaging capacity (1.5 to 2 log).

The inventors were interested in the specific properties of this strain FB29 and have used it to define retroviral vectors.

Figure 1D:
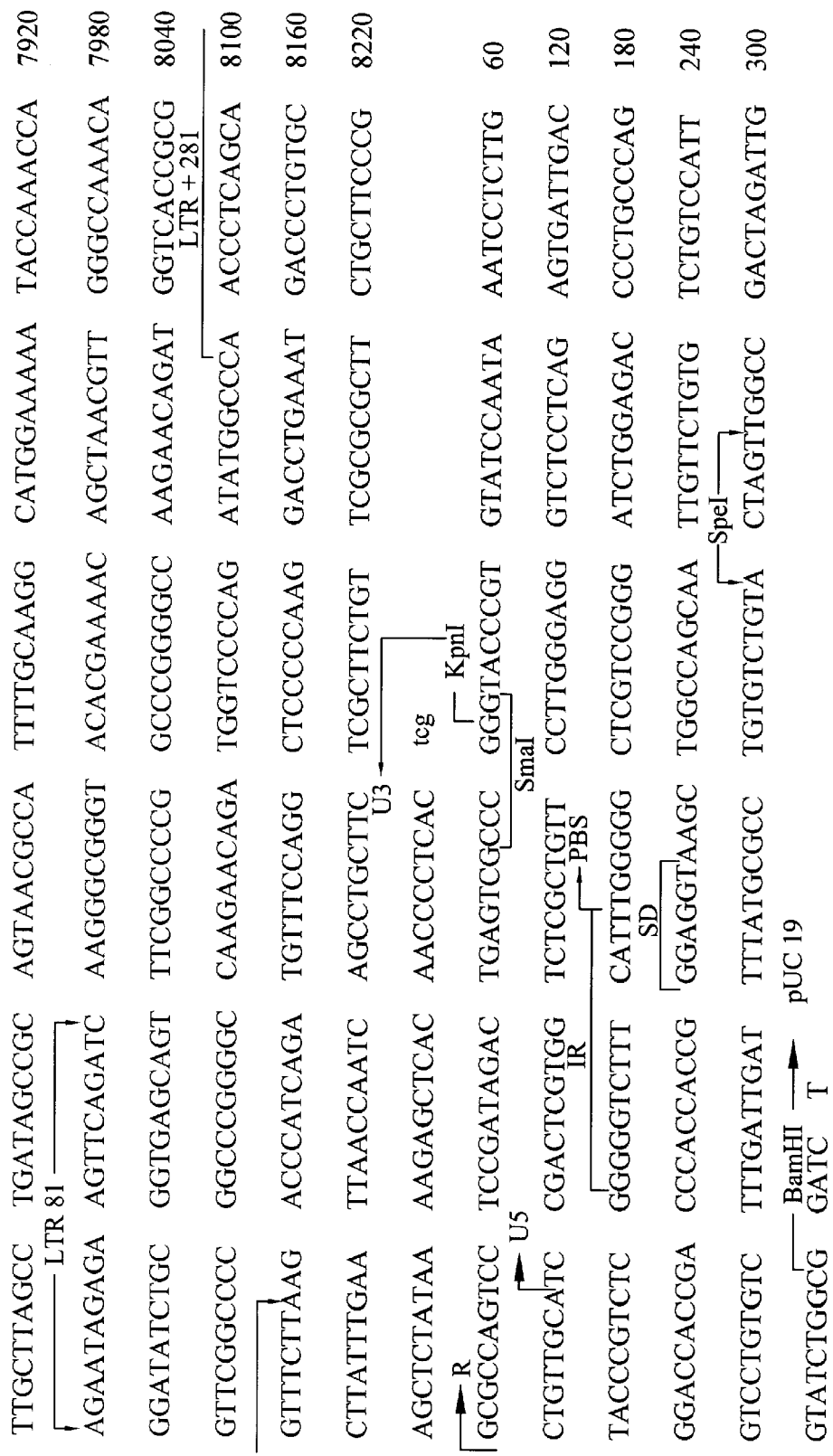

According to a first embodiment, the object of the invention is a recombinant retroviral vector for the cloning and/or expression and/or transfer of an exogenous nucleotide sequence, characterized in that it consists of any sequence contained in the ClaI-PvuII fragment situated approximately between nucleotides 7702 and 1527 (SEQ ID NO:11) of the sequence given in FIG. 1 and comprising the LTR sequence included between nucleotides 7842 and 144, the PBS site starting at nucleotide 145, the packaging sequence included in the sequence of 250 nucleotides following the end of the LTR sequence, the said sequence being capable of controlling the cloning and/or expression and/or transfer of the exogenous sequence.

According to another embodiment of the invention, the recombinant vector is characterized in that it consists of any sequence contained in the ClaI-BamHI fragment comprising the nucleotides 7702 to 310 (SEQ ID NO:13) of the sequence shown in FIG. 1, and comprising the LTR sequence included between the nucleotides 7842 and 144, the PBS site starting at nucleotide 145, the packaging sequence included in the sequence of 250 nucleotides following the end of the LTR sequence, the said sequence being capable of controlling the cloning and/or expression and/or transfer of the exogenous sequence, whatever its transcriptional orientation with respect to the transcriptional orientation of the virus.

According to this second embodiment of the invention, the vector is thus a retroviral vector for the cloning and/or expression and/or transfer of an exogenous nucleotide sequence consisting of any sequence contained in the ClaI-BamHI fragment situated approximately between nucleotides 7702 and 310 (SEQ ID NO:13) of the sequence given in FIG. 1, the said sequence having the capacity to control the cloning and/or expression and/or transfer of the exogenous sequence.

The ClaI and BamHI sites referred to above have their origin in the FB29 strain.

During the construction of the retroviral vectors or vectors destined for the production of packaging lines, these sites may be modified and in particular replaced, optionally creating distinct enzymatic cleavage sites.

A vector comprising the ClaI-BamHI fragment thus contains two LTR sequences, 5' LTR and 3' LTR having the same viral origin. This vector may be modified by deletion of all or part of the viral envelope sequence present upstream and/or downstream from the sequences 5' LTR and 3' LTR A vector of this type is for example pFOCH29—PL described in FIG. 7.

These LTR sequences may be separated in the vector by the presence of the gag sequence referred to above and/or by the exogenous nucleotide sequence which it is desired to transfer, clone or express.

According to an attractive embodiment of the invention, the recombinant vector is characterized in that it consists of all of the Cla—PuvII fragment, comprising nucleotides 7702 to 1527 (SEQ ID NO:11) of the sequence shown in FIG. 1.

Another preferred retroviral vector consists of all of the ClaI—BamHI fragment (7702 to 310 (SEQ ID NO:13)).

A retroviral vector of the invention can be used for therapeutic or diagnostic purposes in order to introduce into the patient a nucleotide sequence of clinical importance. The vector of the invention in fact exhibits the properties of efficiency and safety required for this application.

Advantageously, the control of cloning, expression or transfer of the exogenous sequence is achieved according to the invention, irrespective of the transcriptional orientation of this sequence with respect to the transcriptional orientation of the virus.

An exogenous nucleotide sequence according to the invention is a nucleotide sequence which is not naturally contained in the genetic material constituting the vector and, in particular, in the sequences necessary for the control of the expression, cloning or transfer. It may be a natural or synthetic sequence, in particular a hybrid sequence.

By the expression "transfer of an exogenous nucleotide sequence" is meant the incorporation of a sequence borne by the vector into the genome or satellite of this latter of a cell transformed by this vector. Such a transfer may be the result of recombination, in particular homologous recombination.

The vector of the invention may thus allow the permanent expression in the genome of a target cell of a sequence of exogenous nucleotides selected for its property of integration into the genome of the target cells.

According to an attractive embodiment of the invention, the exogenous sequence and the sequence contained in the ClaI-PvuII fragment or in the ClaI-BamHI fragment or in one of these fragments according to the above description are inserted in a plasmid, for example in the plasmid Puc19, plasmid Puc18 or any other suitable plasmid.

Preferably the recombinant vector additionally comprises a part of the gag sequence situated between the nucleotides 619 and 2245 (SEQ ID NO:14) of the sequence shown in FIG. 5, in the particular the sequence included between nucleotides 619 and 1527 (SEQ ID NO:15) of the sequence shown in FIG. 1.

The presence of a fragment or all of the gag sequence may contribute to the stabilization of the vector obtained. The gag sequence codes for the nucleoproteins of the Friend virus and increases the packaging efficiency, at least in its proximal part.

However, it may be useful to limit the part of the gag sequence present in the vector of the invention as a function of the size of the exogenous sequence introduced into the vector in order to obtain a higher infective viral titer and to diminish the production of viral proteins and the risk of generating replication-competent viruses. Preferably, the part of the gag sequence present in the vector should be less than about ⅔ of the normal gag sequence. Advantageously, the conserved gag sequence is the part of this sequence implicated in the packaging step of the retroviral vector obtained.

A useful vector of the invention is characterized in that it essentially lacks the viral sequences pol and/or env.

Figure 23:
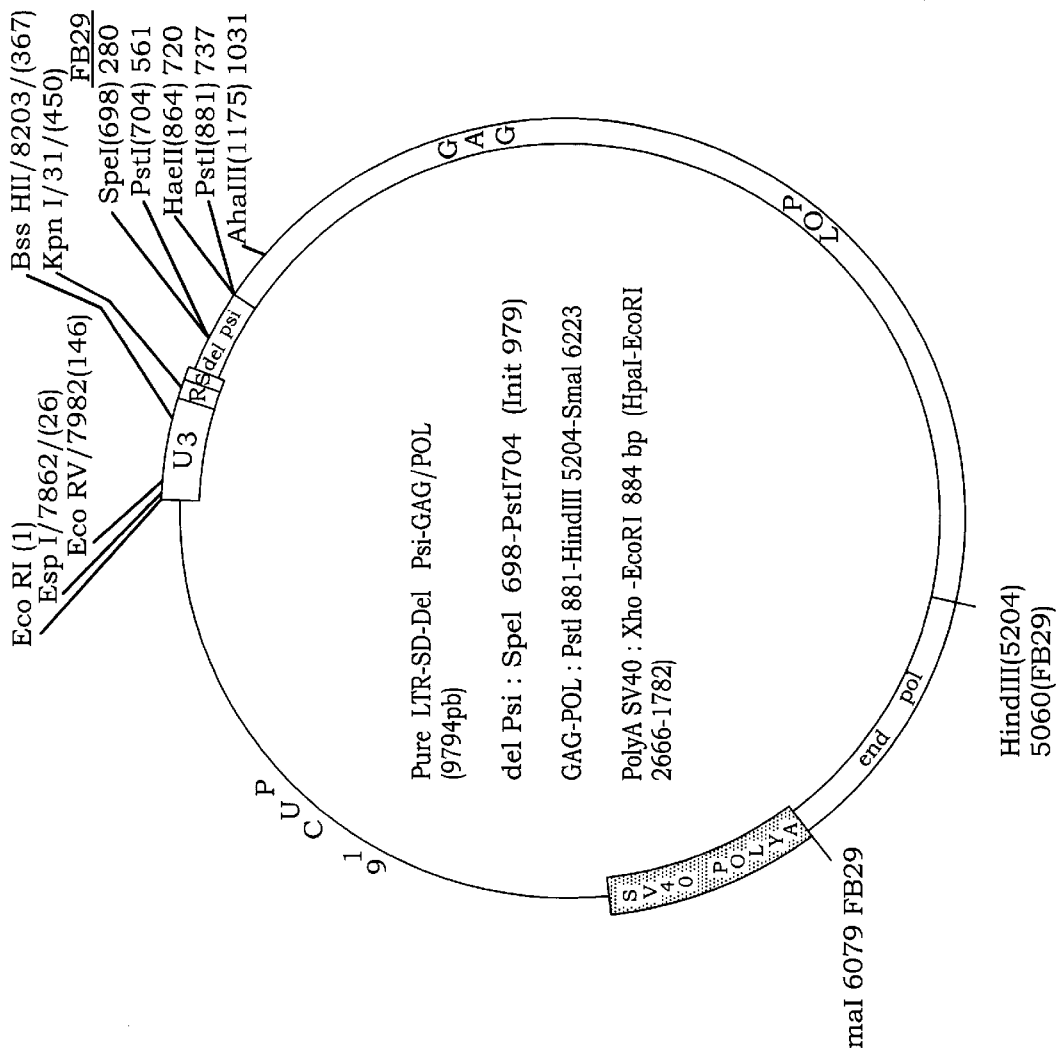

On the other hand, the pol and gag sequences of the FB29 strain as shown in FIG. 5 may be conserved downstream from the LTR for the production of packaging lines (see FIG. 23 as an example).

The expression of the pol and gag sequences can be controlled by a promoter distinct from the viral LTR which is then deleted.

The object of the invention is thus constructions such as described above comprising a sequence contained in the ClaI—PvuII fragment previously mentioned and comprising in addition the gag and pol sequences or a part of these sequences sufficient for the production of packaging lines.

These lines may be used to package the retroviral vector of the invention.

A vector comprising both the ClaIPvuII fragment (which bears a unique LTR sequence) and the gag and pol sequences or a part of these sequences may in particular be used in the context of the preparation of packaging line for ex vivo or in vivo gene transfers, the said gene being represented by the exogenous nucleotide sequence.

When a part of the env viral sequence is present in the vector it remains insufficient to allow recombinations likely to produce replication-competent viruses.

A useful vector of the invention lacking the envelope sequence consists of the fragment comprising nucleotides 7806 to 1527 (SEQ ID NO:12) of the sequence shown in FIG. 1.

The invention also relates to a recombinant vector such that the sequence contained in the ClaI-PvuII fragment (7702-1527) (SEQ ID NO:11) and/or this fragment and/or the sequence contained in the fragment ClaI-BamHI (7702-310) (SEQ ID NO:13) and/or this fragment is replaced either by a sequence hybridizing under conditions of high stringency with the sequence corresponding to the above-mentioned fragments or by a sequence having an at least 95% nucleotide homology with the sequence corresponding to the above-mentioned fragments or at least 85% homology in the case of the U3 sequence.

Hybridization is performed in the same hybridization media as those described in the experimental part by adding, however, two rinsings for 10 min at 65° C. in a 1x SSC, 0.1 SDS medium as well as 2 rinsings for 10 min. at 65° C. in a 0.1x SSC, 0.1 SDS medium.

The nomenclature of the nucleotides is given above by reference to the numbering of the nucleotides of the viral sequence shown in FIG. 1.

Optionally, one of the two LTR sequences previously defined starting from the sequence of the F-MuLV virus (strain FB29 of the Friend virus) may be replaced by a LTR sequence derived from another virus, for example from the Moloney murine leukemia virus (Mo-MuLV).

Similarly, the recombinant vector of the invention may also contain other retroviral sequences than those which have been described above, either derived from the same F-MuLV virus whose sequence is given in FIG. 5, or derived from another virus.

The object of the invention is also a recombinant vector characterized in that it contains in addition at least one polylinker possessing uniques restriction sites with respect to the sites contained in the vector.

Such an adaptor, preferably with multiple sites (polylinker), permits in particular the insertion of one or more exogenous sequences whose transfer, cloning or expression is desired.

A perticularly useful vector is the vector characterized in that it is the plasmid pFOCH29 deposited under the designation pFOCH29-SCS1 in a strain of *E. coli* SCS1 with the C.N.C.M. on Jun. 30, 1993 under No. I-1326.

The strain *E. coli* SCS1 is marketed by the STRAT-AGENE Corp company.

A vector of the invention may also contain a marker gene or part of a marker gene such as for example the gene for neomycin resistance. The presence of a marker gene facilitates in particular the detection of the presence of the vector in recombinant cells.

The object of the invention is also a recombinant vector complying with the foregoing specifications in which the U3 region of the LTR is deleted at least in part such that the transcriptional sequences in particular the promoter and/or enhancer contained in U3 is (are) at least in part inactivated or modified.

In this case, the vector is capable of autoactivation or is a SIN vector ("self inactivating vector"). A SIN vector thus constructed allows the expression of the exogenous sequence which it contains when the latter is placed under the control of a so-called "internal promoter", viral or non-viral in nature, optionally the promoter of this sequence, or a promoter such as the promoter of the EGF (epidermal growth factor) receptor or the ubiquitous PGK promoter of phosphoglycerate kinase.

The advantage consists in improving safety (non propagation and diminution of the risk of activation of neighbouring sequences). Another advantage is to profit from the integration mediated by the retroviruses but to specify or target transcription by the internal promoter.

Similarly, the U5 sequence, even if necessary the sequence R, may be deleted at least in part.

This deletion may be performed at the unique LTR sequence present in the vector or optionally at each LTR sequence of this vector.

However, this leads most often to a diminution of the viral particle titer, even to the absence of integration into the genome of the target cell (if U5 deleted).

According to another embodiment of the invention, the exogenous nucleotide sequence is under the control of an exogenous (or internal) promoter.

By "exogenous promoter" is meant a promoter which is not naturally present in the vector. Such a promoter may be the natural promoter of the exogenous sequence. It may be a constitutive promoter or an inducible promoter.

A previously defined recombinant vector is preferably introduced into a packaging line for example by transfection or electroporation. This transfection allows the constitution of viral particles intrinsic to the production of recombinations by transduction in target cells for the purpose of cloning, transfer or expression of the exogenous nucleotide sequence contained in the vector.

Thus, a particularly useful vector may be transfected into the psi-CRIP line.

It is also possible to have recourse to the packaging line psi-CRE or to any other line provided that it does not lead to recombinations likely to give rise to the production of wildtype viral particles from the proviral DNA contained in the vector.

According to another embodiment of the invention, the recombinant vector may be introduced into liposomes or into a macromolecular complex (Monsigny M et al. M/S 1993).

The F-MuMV vector may be used to produce such packaging lines according to the procedure illustrated in McLachlin J R et al., 1990. Such a line may be constructed from sequences of the gag, env and pol genes, the packaging sequence being deleted and at least one of the gag, pol or env sequences bearing a point mutation which does not adversely affect the resulting protein.

The vectors of the invention may contain one or more exogenous sequences. These sequences may be inserted outside the ClaI-BamHI or BamHI-BamHI fragments as was seen above or, on the contrary, may be inserted within these fragments and in particular in their LTR sequence.

These vectors may also contain cell targeting elements to orient the integration of the vector in specific cells.

Advantageously, on infection of the target cells, the retroviral vector constructions according to the invention lead to a viral titer equal to or higher than $10^4$ pfu/ml evaluated when the exogenous nucleotide sequence coding for the neomycin gene is inserted into this vector.

This vector may have very diverse uses and in particular these vectors may be used for the cloning, expression and/or transfer of nucleotide sequences having clinical (therapeutic or diagnostic) importance.

Thus it is possible to use the vectors of the invention for the transfer into cells, for example somatic cells, or genes for therapeutic purposes whatever the disorder(s) or disease(s) concerned.

The therapeutically important sequences referred to here are for example sequences corresponding to the normal equivalent of a non-functional gene in the case of a given disease or also of an antisense sequence or a dominant negative mutant of a given gene or a sequence coding for a functional inhibitor of a gene or the use of a marker gene.

The vector of the invention is thus appropriate for the gene therapy of cancer by application of gene correction techniques or improvement of the strategies for the destruction of tumor cells. According to the first approach it is possible to use the vector to correct constitutional mutations in the case of hereditary predisposition to cancer, abnormalities of the signal transduction like the pathways mediated by the ras oncogene and its homologues, enhancer abnormalities of oncogenes, inhibitory abnormalities of tumor suppressor genes, abnormalities promoting genetic instability, abnormalities affecting DNA repair.

According to the second approach the vector may be used to activate prodrugs as in the case of the thymidine kinase gene of the herpes virus which converts Ganciclovir or Acyclovir into cytotoxic drugs, or the cytosine deaminase gene which converts a precursor of 5-fluorouracil into an active drug, or to induce or stimulate the immune system by manipulation of tumor cells with for example cytokine genes, by manipulation of antigen-presenting cells or their precursors (hematopoietic stem cells) or by manipulation of the immunity effector cells, T cells, B cells, LAK, TILs.

When the correction of genetic diseases and anemias is involved, the invention can for example be applied to the correction of inborn errors of metabolism, hemoglobin diseases such as thalassemias or sickle cell anemia, diseases of hemostasis and coagulation, hereditary diseases of demyelination or myopathies.

The vectors of the invention are also suitable for vaccinating patients against pathological agents, either permanently or transiently.

The transfer may be achieved by transduction into cells, tissues, organs or organisms.

According to another embodiment of the invention, the exogenous nucleotide sequence codes for anantigen or an antigenic determinant.

A vector containing such an antigenic determinant should be used as permanent or transient vaccine or optionally in the context of a therapeutic protocol for example to provoke an immune response.

As an example, sequences of HIV retroviral antigens may be incorporated into the vector of the invention.

In this connection, the retroviral vector of the invention may be used for intracellular immunization by using transdominant mutants of CD4, Tat, Rev, Gp120, decoys with excessive synthesis of regulatory proteins such as TAR, specific ribozymes of viral sequences or antisense genes.

This same procedure may be used to treat other retroviral infections.

The exogenous nucleotide sequence previously mentioned may be a sequence of genomic DNA or a cDNA sequence or also an RNA sequence.

Similarly, this sequence may be natural or synthetic.

The object of the invention is also a eukaryotic or prokaryotic recombinant cell characterized in that it is modified by a recombinant vector of the invention. Advantageously, it is a cell of a species not bearing an endogenous retrovirus.

Such a cell is advantageously a mammalian cell, in particular a human cell.

Similarly, it is either a totally differentiated cell or a cell of the precursor type. For example, the vector of the invention is particularly suitable for the modification of hematopoietic cells and also hematopoietic cell precursors or of a cell of a lymphomyeloid totipotent strain.

Moreover, glial or neuronal nerve cells may also be modified by the vector of the invention.

Other cells may be modified by the vectors of the invention for example T or B lymphocytes, or other mediators of cell immunity, tumor cells, medullary stroma, endothelial or mesenchymatous cells.

The recombinant vector according to the invention may also be used to modify fibroblasts, cutaneous cells, hepatic cells or muscle cells.

Other cellular targets may be transformed by the vector of the invention. Mention should be made of epithelial cells, for example of the mammary or vesicular epithelium, tumor cells, accessory cells of the nervous system such as precursors of oligodendrocytes or Schwann cells.

It is also possible to modify cell lines such as lines of JURKATT T lymphocytes, NK cell lines such as YT2C2, lines of monocytes-macrophages (for example U937) or erythromegakaryocyte lines (for example K562).

Other characteristics and advantages of the invention will become apparent in the examples and Figures which follow.

FIG. 1: Sequence of viral DNA used for the construction of the vector FOCH29.

Figure 2A:
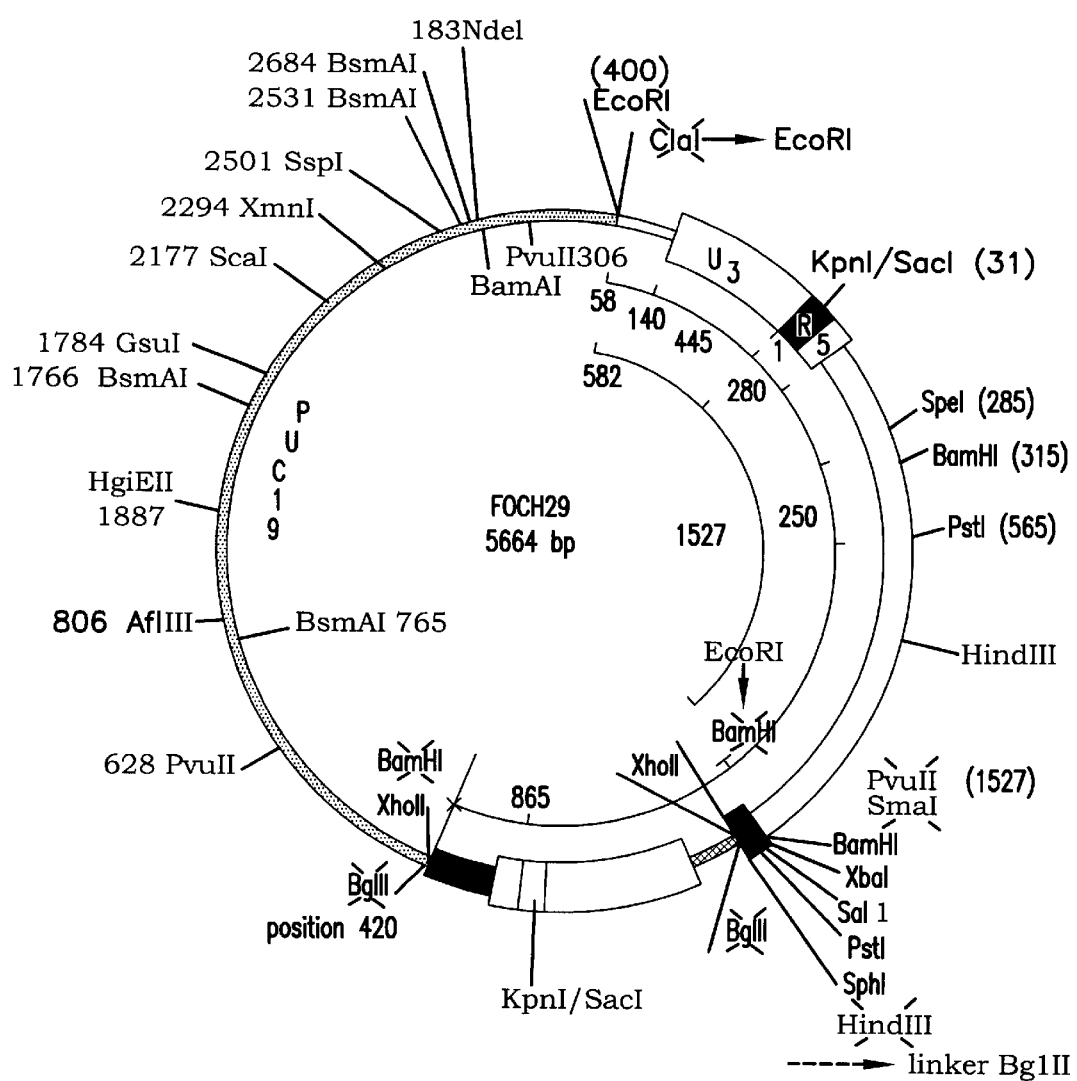
Figure 2B:
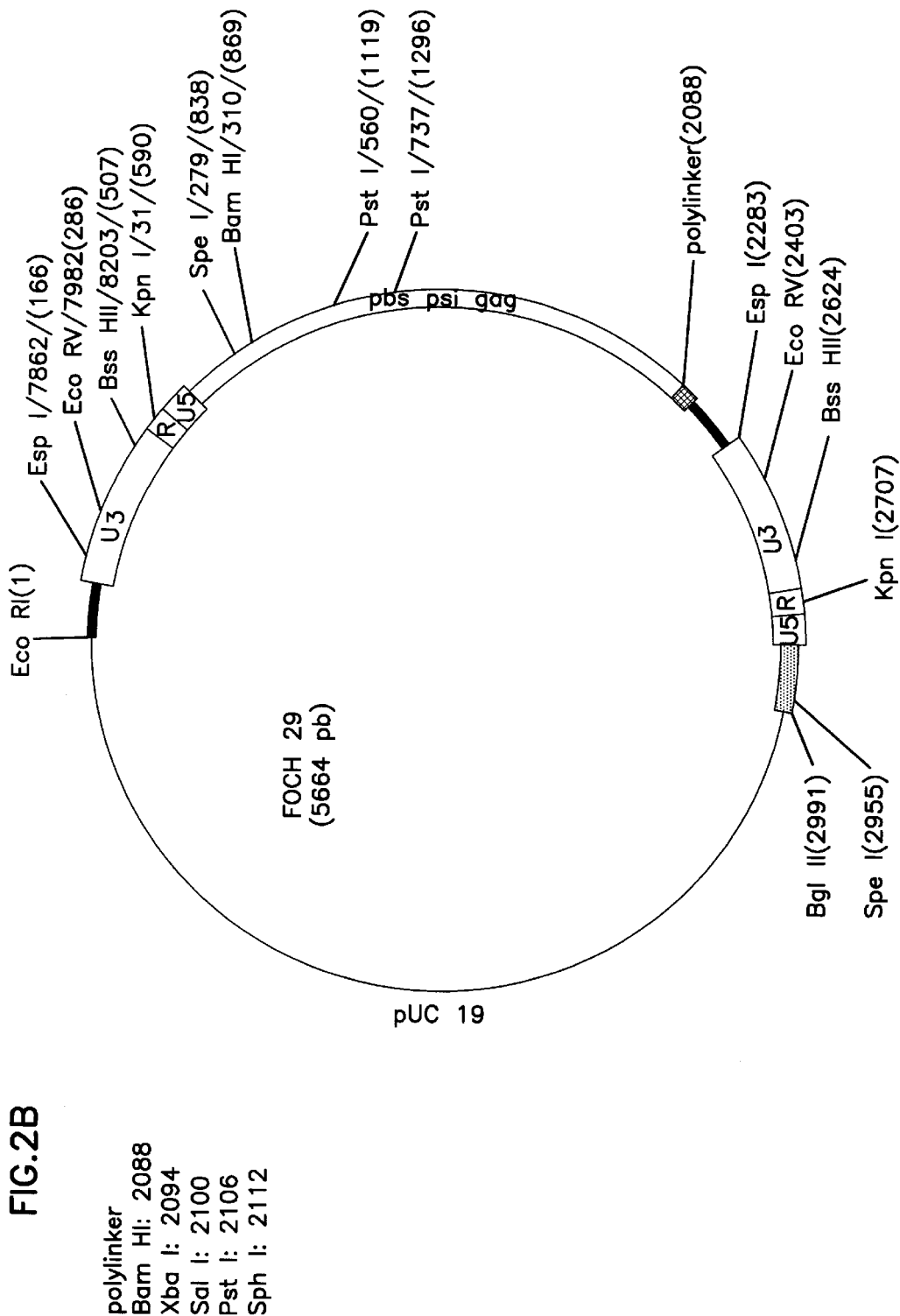

FIG. 2: A: Restriction map of the vector FOCH29. References Seq "FB29"

Cla→U3 140 (7702–7842)

U3→R410 (7842–8255)

R→CBS 145 (0–145)

PvuII→BamHI 208

PvuII→PvuII 1098

PvuIIMT→PvuII 1669

BsmAI→55/150/765/1766/2531/2684

B: Restriction map of FOCH 29 in the which the sites are indicated using the numbering of the FB 29 sequence shown in FIG. 1 and with the numbering intrinsic to the construction thus achieved (numbers in parentheses).

Figure 3:
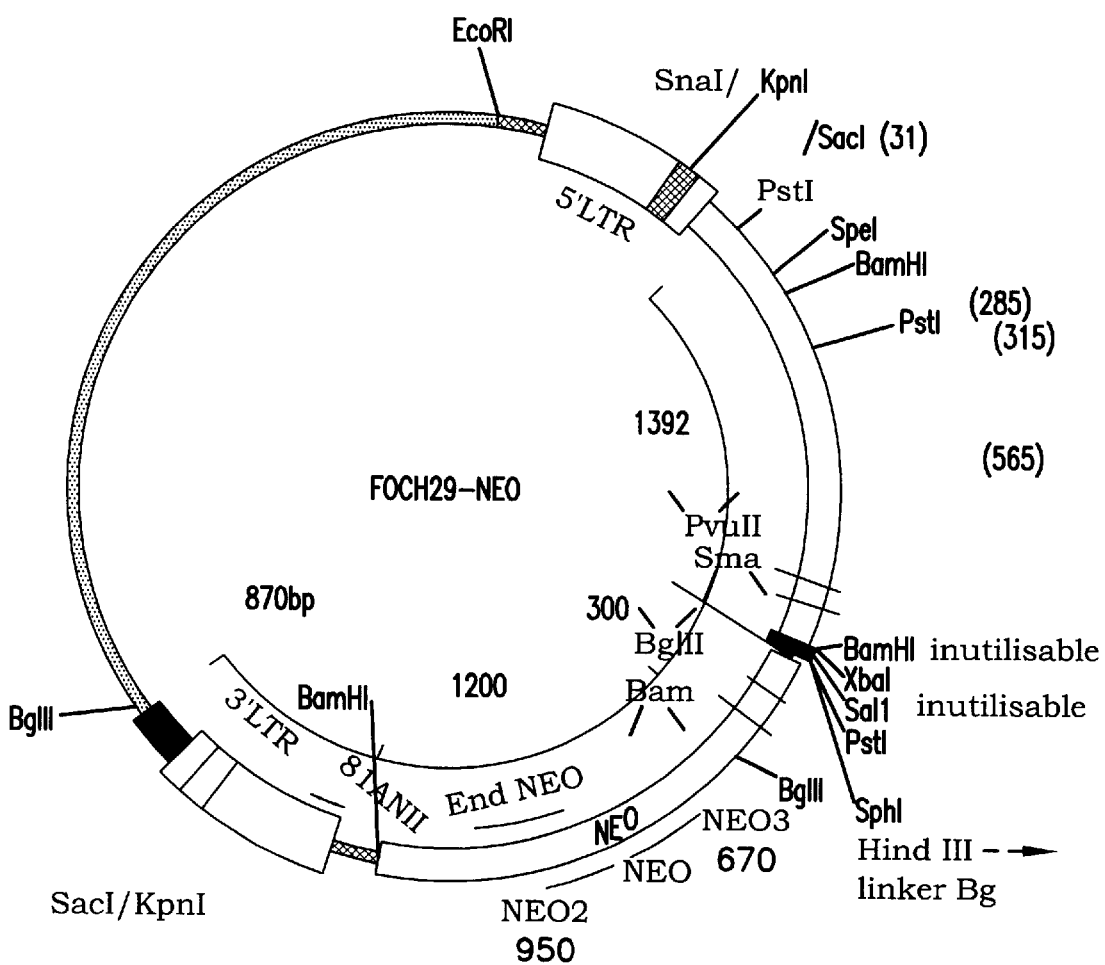
Figure 6:
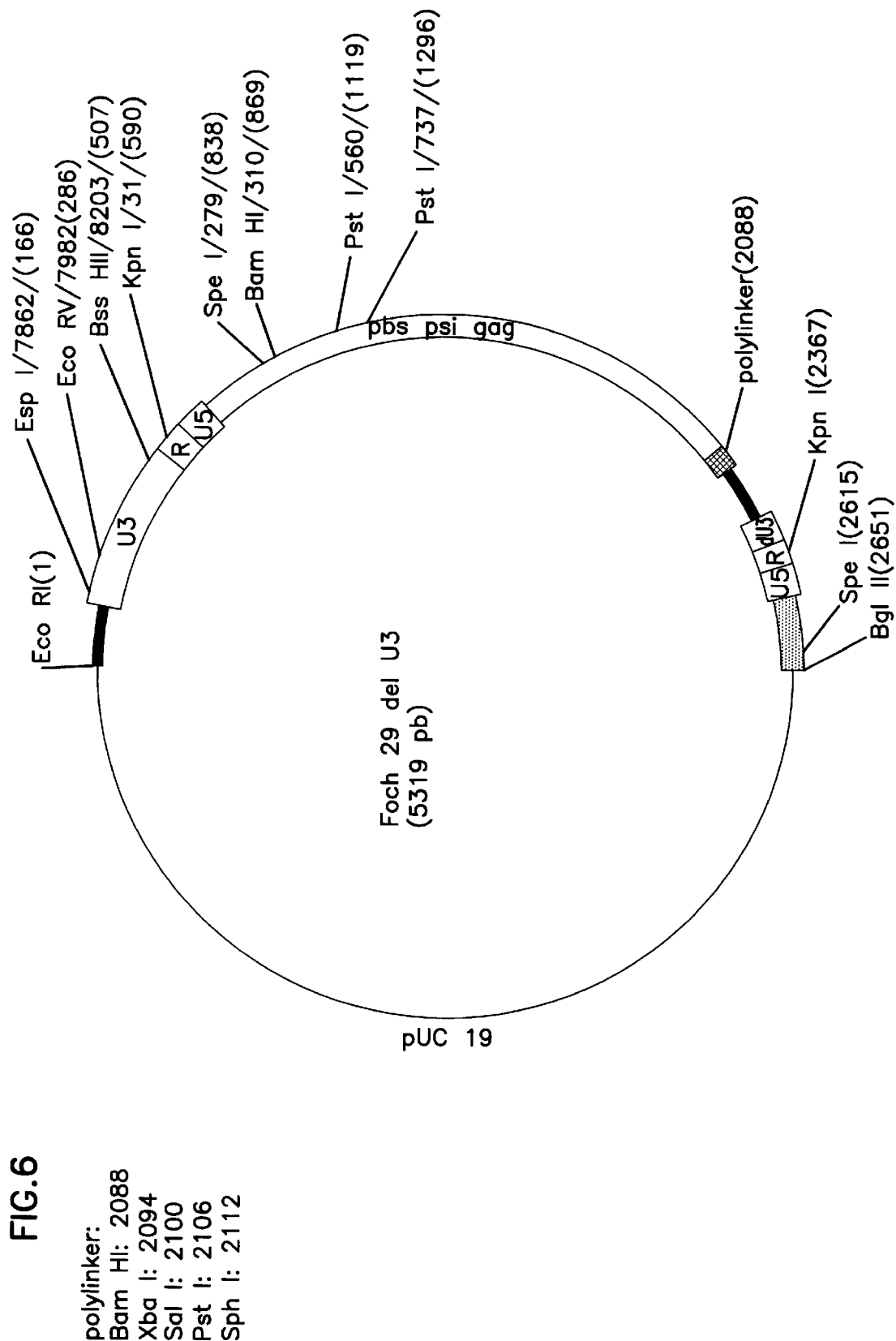

FIG. 3: Restriction map of the vector FOCH29-Neo. The neo gene was cloned into the polylinker. The enzymes which can be used in the polylinker are Xba, Sal, SphI Cuts:

BglII
  2070
  5300

Bam
  1392
  1500
  4456

Sal/BglII
  300
  2070
  5000

FIG. 4: Restriction map of the plasmid pUC19

FIG. 5: Sequence of F-MuLV

FIGS. 6 to 24: Restriction maps of the constructions produced from the retroviral vector FOCH29

EXAMPLES

A) PREPARATION OF THE RETROVIRAL VECTOR

MATERIALS AND METHODS

1. Source of the viral genomic material

The genomic DNA of the provirus was cloned in pBR322 (Sitbon et al., 1986). After replacement of the ClaI site at 7702 of the viral sequence by a EcoRI site, the EcoRI-PvuII fragment of 2110 base pairs (bp) containing all of the viral Long Terminal Repeat (LTR) was subcloned at the EcoRI and SmaI sites of the polylinker of pUC19.

2. Construction of the retroviral vector FOCH29

The HindIII site of the polylinker of pUC19 containing the EcoRI-PvuII fragment was replaced by a BglII site, after opening by HindIII, filling in with the long fragment of E. coli DNA polymerase (Klenow fragment) and ligation with a BglII adaptor not recreating the HindIII site; the BglII site was introduced to receive a BamHI-BamHI fragment of 865 bp containing a second copy of the native LTR of the Friend virus destined to constitute the downstream LTR (or 3' LTR). This BamHI-BamHI fragment was isolated by replacing the EcoRI site of pUC19 by a BamHI site upstream by means of a linker not recreating the EcoRI site after filling in of the ends by the Klenow fragment of the DNA polymerase; the BamHI site downstream is endogenous to the viral sequence.

This fragment was thus introduced by ligation with the backbone (pUC19) whose opening by BglII made it possible to combine the cohesive ends with the ends generated by BamHI. The resulting plasmid is called pFOCH29.

3. Introduction of a marker gene

The BglII-BamHI cDNA fragment (1500 bp) of the gene for neomycin resistance derived from the retrotransposon Tn5 (NeoR) was introduced between the two viral LTRs after ligation of the three fragments: pUC19-5' LTR BglII, NeoR BglII-BamHI and 3' LTR BamHI-BamHI. The resulting plasmid is called pFOCH29-Neo.

4. Transfection of packaging lines psi-CRIP and infection of fibroblasts

The plasmid pFOCH29-Neo was introduced into the amphotropic packaging line psi-CRIP described by Danos et al. (1988) by transfection using calcium phosphate precipitation according to the standard procedure without DNA carrier; 10 micrograms of plasmid were deposited on a culture dish 35 mm in diameter on which $5 \times 10^4$ cells were seeded the day before.

The psi-Crip cells were grown in Dulbecco's modified Eagle's medium (DMEM, Gibco—BRL) supplemented with 10% newborn calf serum (Hyclone). Two days after transfection the cells were trypsinized, diluted ¹⁄₂₀ and subjected to selection in the presence of geneticin at a final concentration of 1 milligram (mg) per milliliter (ml) of culture medium. The colonies which appeared after 12 days were selected and reimplanted on 24-well culture dishes at a concentration of one clone per well.

The cell culture supernatant of a well which had reached confluence was taken, filtered through a 0.45 μm filter to remove cells in suspension and used to infect mouse fibroblasts (NIH3T3) seeded identically on 24-well culture plates in the presence of polybrene at a concentration of 8 μg/ml. The NIH3T3 were grown in DMEM supplemented with 10% fetal calf serum (FCS). Viral integration was analysed by PCR on a lysate of NIH3T3 which had reached confluence.

5. Polymerase chain reaction (PCR)

The lysate supernatant of the confluent NIH3T3 in a well of the 24-well culture plate was recovered in 100 μl, 10 μl of which were used in the PCR reaction, which is carried out in the following buffer: 10X standard PCR buffer including 25 mM of $MgCl_2$ (Perkin-Elmer/Roche M S); 100 nanograms (ng) of each primer; 2 μl of dNTPs 10 mM (equimolar mixture of each dNTP at an initial concentration of 10 mM, i.e. 2.5 mM of each); 2 units of cloned Taq polymerase (Perkin-Elmer/Roche MS) for 40 cycles, a single unit for 25 cycles; in a final volume of 50 μl.

Two pairs of primers were used.

The oligonucleotide sequences used are:

1°) for the first pair:
   5' CTGCTGACGGGAGAAGAAAAAC-3'(SEQ ID NO:3) 5' CCCGCTCAGAAGAACTCGTC-3'(SEQ ID NO:4)

2°) for the second pair:
   5' GACGAGTTCTTCTGAGCGGG-3'(SEQ ID NO:5) 5' GATCTGAACTTCTCTATTCTTG-3'(SEQ ID NO:6)

The size of the amplified sequences is in the case of the first pair, end-gag/two thirds proximal NeoR gene: 900 bp; and for the second pair, one third distal NeoR gene/proximal half of 3' LTR: 610 bp.

Denaturation 5 min at 94° C.; 40 cycles on GeneAmpPCR 9600 with denaturation 30" at 94° C.; annealing 15" at 55° C. and elongation 30" at 72° C.; followed by a terminal elongation step of 10 min.

The samples (15 μl out of 50 μl) were deposited on a 1.2% agarose gel (Seakem, FMC) and were subjected to horizontal electrophoresis for 45 min at 80 volts; the detection of the signal based on the analysis of the intensity of ethidium bromide (BET) fluorescence.

6. Determination of the infective titers

Each of the clones tested for its capacity to infect NIH3T3 was amplified and optionally frozen prior to the analysis of the efficiency of infection by PCR.

After PCR two principal clones were selected and amplified in order to infect NIH3T3 according to a standard procedure 1 ml of 16 hours culture supernatant was taken at confluence from each producing clone on a dish 35 mm in diameter, filtered through a 0.45 μm filter in order to remove productive cells in suspension. The supernatant was placed in contact with NIH3T3 cells at 50% confluence on culture dishes of the same diameter (35 mm) in the presence of polybrene at a concentration of 8 μg/ml of medium. The cells were incubated for about 2 h 30 at 37° C.; the medium was shaken every half hour. Three volumes of fresh medium were added after 2 h 30.

INFECTIVE VIRAL TITERS

Successive dilutions of the primary supernatant were used to infect NIH3T3 cells; undiluted supernatant and supernatant at dilutions 1/10, 1/1000 and 1/100000. Two days after infection the cells were trypsinized, subcultured at about 1/20 on three culture dishes 100 mm in diameter and placed under selection by the addition of geneticin (1 mg/ml) to the supernatant.

This experimental procedure was made more stringent in the sense that: on the one hand, the drug was added very quickly after the infection; and, on the other, the direct placing in selection without trysinization of the cells prevents the artificial multiplication of the number of resulting colonies, the daughter cells derived from an infected cell remained group together and formed only one colony in situ. Conversely, when the cells are trypsinized, the daughter cells spread on the recipient culture dish and form artificially independent colonies which, if they are counted, artificially multiply the titer.

SOUTHERN BLOT

Two days after infection by the undiluted supernatant the NIH3T3 were trypsinized, subcultured at about 1/20 on three culture dishes 100 mm in diameter, one of which is subjected to selection by geneticin.

At confluence, the genomic DNA of the infected cells for each of the two clones after or without selection is extracted then quantified.

The DNA was digested by two restriction enzymes, PstI and KpnI, in order to carry out a Southern blot. After control of the quality of the digestion and the deposition of an equivalent quantity of DNA in each well, the transfer was carried out on a nylon Hybond N membrane (Amersham). Hybridization was performed with a probe which included all of the viral LTR sequences flanked by 100 bases upstream and 100 bases downstream. The probe was labelled by primer extension (Feinberg and Vogelstein, 1983, 1984) with alpha-$^{32}$P labelled dCTP of specific activity of $5 \times 10^8$ cpm/μg.

The hybridization was carried out in a medium consisting of: 50% deionized formamide; 5x SSEP; 1x Denhardt's; 5% dextran sulfate and 0.2 mg/ml of sonicated salmon DNA for 20 hours at 42° C. Brief rinsings were carried out in a solution of low stringency: 2x SSEP/0.1% SDS, 5 min at room temperature and 10 min at 65° C.; followed by exposure for 3 days to KODAK-XAR-5 films at −80° C. with LI-Plus intensifying screens (Dupont-NEN).

7—Search for the production of helper virus

This search was carried out by a mobilization test on 3T3BAG lines (Danos et al., 1988; Danos, 1991).

The 3T3BAG cells were initially infected by the undiluted supernatant of infected packaging line. Several successive cycles of infection of unexposed 3T3BAG with the supernatant of previously infected 3T3BAG were carried out to sensitize the test.

RESULTS

1. Construction of the retroviral vector FOCH29

The viral strain FB29 of the Friend murine leukemia virus was isolated (Mathieu-Mahul et al., 1982) and the genomic DNA of the integrated provirus was cloned in pBR322 (Sitbon et al., 1986). This genomic DNA has been completely sequenced (Perryman et al., 1991). The genomic fragment ClaI—PvuII of 2120 bp was cloned in pBR322. This fragment contains the last nucleotides of the sequence coding for the p15E of the viral envelope, all of the Long Terminal Repeat (or LTR) and 3/5 of the gag sequence. It constitutes the matrix of the architecture of the vector.

After replacement of the ClaI site by a EcoRI site the EcoRI-PvuII fragment was subcloned in the EcoRI-SmaI of the polylinker of pUC19. This clone was, on the one hand, kept intact to form the basic architecture of the vector including: the upstream LTR of 5' LTR, the binding site for the initiator of viral transcription (primer binding site or PBS), the packaging sequence, the gag sequences and the segment of the polylinker of pUC19 treated by EcoRI/SmaI digestion; destined for the insertion of the genes of interest.

On the other hand, a BamHI-BamHI fragment was derived by replacing upstream the EcoRI site by a BamHI site; and by taking advantage downstream of the endogenous BamHI site of the virus, situated immediately downstream from the donor splice site. This fragment was introduced into the basic framework of which the HindIII site of the polylinker has been replaced beforehand by a BglII site generating ends cohesive with those generated by the BamHI enzyme.

The marker gene derived from the retrotransposon Tn5 which confers resistance to neomycin (NeoR) was introduced between the two LTRs. After transformation on a strain of supercompetent bacteria of dominant negative recombinase phenotype in order to prevent possible reorganization of the sequences present, the transformants of the expected configuration were selected on the basis of the extended restriction map exploring all of the construction. One of them, designated pFOCH29, was then amplified and purified in order to have available an adequate source of material destined for the transfection of helper lines producing viral particles.

2. Isolation of producer clones of defective virus

Transfection of psi-CRIP packaging lines: the plasmid pFOCH29-Neo was introduced in to the amphotropic packaging line psi-CRIP described by Danos et al. (1988) by transfection using calcium phosphate precipitation according to the standard procedure without carrier DNA.

After subjection to selection by geneticin, 40 of the colonies formed were taken and the culture supernatant was used to infect mouse fibroblasts (NIH3T3). The primary selection process of a series of the most highly productive clones of packaged defective viral particles was based on the use of the gene amplification procedure by means of the polymerase chain reaction. The viral integration is analysed by PCR on a lysate of NIH3T3 which had reached confluence.

Two distinct PCR primer couples were used: 1° a first couple amplifying the terminal segment of the gag sequences included in the construction and the proximal two thirds of the gene for neomycin resistance; 2° a second primer couple amplifying the distal third of the gene for neomycin resistance and the half of the downstream LTR (3').

Four clones were selected on the basis of a more intense PCR signal than the other 36; repetition of the procedure confirmed the initial data indicating that for two clones the signal was emitted markedly more intensely. These two clones were amplified and the culture supernatant of the producer cells was then used to infect NIH3T3 on a larger scale for the purpose of evaluating the efficiency of the construction in quantitative terms.

3. Evaluation of the producer clones

Quantitative PCR

A semi-quantitative analysis by PCR was performed by using the primer couple amplifying the region corresponding to the distal third of the NeoR gene up to the median part of the downstream LTR (3' LTR). For each clone 1 µg and 3 µg of genomic DNA extracted from NIH3T3 cells infected by an undiluted supernatant after or without selection by neomycin were used. Each assay was performed in duplicate.

Several dilutions of the plasmid pFOCH29-Neo were tested in parallel calculated such that they correspond to 0.1, 0.5 and 1 copy of transgene for the equivalent of 1 µg of genomic DNA, i.e. 0.115 pg, 0.575 pg and 1.15 pg respectively for a plasmid of 7164 bp.

The PCR was carried out for 24 cycles, which still corresponds to an exponential phase of the reaction. The reading was performed by computerized densitometric analysis (Cybertech) of ethidium bromide fluorescence (cf. Table).

In the case of the first clone a significant difference was observed between the intensity of the signal obtained from selected and non-selected infected cells; more clear-cut on the samples of 1 µg (70% of the signal with respect to the selected) than on those of 3 µg for which the detection system was saturated by the intensity of the signal.

In the case of the second done, there is no difference in intensity of the signal between selected and non-selected cells, neither for the 1 µg samples nor the 3 µg samples. This suggests that a percentage of the NIH3T3 cells close to 100%. had been infected by the undiluted supernatant of this producing done. The high degree of infectivity of this done was moreover suspected by the observation of an absence of cell mortality when the NIH3T3 infected with the culture supernatant were subjected to selection by neomycin.

Southern Blot

The DNA of the infected NIH3T3 cells was subjected to hydrolysis by two restriction enzymes: KpnI and PstI. The expected size of the bands after viral integration varies depending on the probes used. In the case of the enzyme KpnI which cuts within the LTRs and in the middle of the polylinker of pUC19, a LTR probe reveals a constant fragment size of 3610 bp and two fragments of variable size depending an the proximity of the endogenous genomic KpnI sites to the integration site; a probe derived by PCR with the primers distal third NeoR/proximal LTR segment, a fragment of the same size (3610 bp) is expected and only one of the two other fragments variable from one integration to another.

In the case of the enzyme PstI which cuts twice in the median part of gag and once in the polylinker of pUC19, after integration the fragments identified by the former two probes should be of variable size; a probe generated by PCR from the second primer couple identifies a constant fragment of 790 bases.

Several dilutions of the plasmid pFOCH29-Neo digested by KpnI and PstI were analysed on Southern blot; these dilutions correspond to 0.1, 0.5 and 1.0 copies of plasmid, respectively, for 10 µg of genomic DNA.

Furthermore the DNA of the infected cells not selected by neomycin was systematically placed side by side in order to quantify the infectivity of the construction; the cells which had undergone selection constituted an infection control of 100.

Titration: Infective viral titers by viral dilutions

Successive dilutions of the primary supernatant were used to infect NIH3T3, undiluted supernatant, supernatant diluted 1/10, 1/1,000 and 1/100,000. The cells are infected by a viral supernatant in the proportion of 0.5 ml per well 35 mm in diameter: the selection drug is added precisely 20 hours after infection directly on to the culture dish without trypsinization of the cells. The infective titer selected corresponds to the number of colonies observed for the last dilution at which colonies appear, multiplied by the inverse of this dilution.

In the case of the first clone the titer of initial producer cells is $2 \times 10^6$ pfu/ml. In the case of the second done the titer is $10^6$ pfu/ml.

The two producer clones were frozen normally in order to conserve initial passages on the one hand; and an the other, maintained in continuous culture for several months. The successive titrations (dilutions of the viral supernatant) made it possible to identify a progressive diminution of the titers. In the case of the first clone, the titer passed from more than $2 \times 10^6$ to only $10^1$ in the interval of two months' continuous culture; this drastic fall in the titer was accompanied by a change in the growth of the cells in culture with a concentric appearance and ease of detachment. In the case of the second clone, the titer passed from more than $10^6$ to $10^5$ in an interval of two months' of continuous culture to diminish to $10^3$–$10^4$ after three and a half months; this moderate fall in the titer was not accompanied by any change in the morphology or growth of the cells in culture.

4-Helper activity assay on 3T3 BAG

This research was conducted by the mobilization test on 3T3 BAG lines (Danos et al., 1988; Danos, 1991)

The 3T3 BAG cells were infected initially by the undiluted supernatant of infected packaging lines. Several successive cycles of infection of unexposed 3T3 BAG with the supernatant of previously infected 3T3 BAG were carried out to sensitize the assay, which proved to be negative. Furthermore, colonies of cells resistant to neomycin could not be detected after placing the unexposed NIH3T3 in contact with the supernatant of infected NIH3T3 selected by neomycin.

5) Integration Sites

Human and non-human primate cells were used to identify the number of integration sites of the virus after infection. The mouse cells provide indications of very moderate quality in as much as there exists in these cells a significant background associated with multiple integrations of retroviral or retroviral-like sequences.

For this purpose, monkey VERO cells were infected with several dilutions of viral supernatant. In the case of the dilution $10^{-2}$, independent clones were obtained; each one having been initiated from a single profile of viral integration. The use of a restriction enzyme which cuts within the viral construction, on the one hand, and in the genomic DNA of the cell host at variable distances from the integration sites, on the other, made it possible to obtain as many restriction fragments of variable size as there were integration events. In this case the enzymes XbaI or SalI were used.

6) Stability of the Viral Titers—master Bank System

A homogeneous stock of cells producing virus was constituted and extensively controlled for the absence of viruses competent to replicate by the following methods:

Mobilization test on 3T3 BAG cells

Amplification an NIH3T3

Intraperitoneal inoculation of newborn mice, in order to study a possible in vivo pathogenesis.

Starting from this cell bank ("Master Cell Bank" MCB) a working cell bank was constituted. The viral titers obtained remained stable for several months and were; of the order of $20 \times 10^6$ to $3 \times 10^7$ cfu/ml (the initial dilutions having been grown systematically only at $10^{-6}$). Results were also obtained with an assay including a dilution at $10^{-7}$. The titers are remarkably stable for several months at this level of intensity.

DISCUSSION

1° Construction of the virus

The viral construction was based on the principle of conservation of critical sequences such as the PBS, the packaging sequence, the donor or splice site and also on the conservation of a long gap segment, the maintenance of which contributes to the stabilization of the transcripts as other authors have shown (reviewed by McLachlin et al., 1989).

Several other constructions derived from the same retroviral skeleton have been produced previously; including an initial one in which the 3' LTR was flanked upstream and downstream by longer retroviral sequences and in which two polylinkers of pUC19 and pUC18 were present. Great instability and modest infectivity resulted from this configuration.

A version similar to that of FOCH29 was constructed; similar in all points except for the insertion of a large sequence including the acceptor splicing site of the "clone 57" strain of the Friend virus (Sitbon et al.). The resulting plasmid was designated pFOCH29SA-Neo. The infectivity of this construction proved to be less marked than with pFOCH29-Neo. Nonetheless this difference was only perceived on the data of thee primary screening by PCR.

2° Selection of the producer clones

The primary selection of the producer clones by the procedure described in the Results section exploits the polymerase chain reaction; the conditions used limit the resolving power of the method to a threshold which corresponds approximately to a minimal retroviral titer of $10^4$ pfu/ml. The potential disadvantage of this procedure is linked to the not absolutely quantitative character of the PCR, in particular for forty amplification cycles; consequently, there is a not inappreciable probability of missing highly productive clones. In order to compensate in part for this disadvantage a primary selection procedure based on two independent primer couples for PCR was adopted.

3° Efficiency of the infection and stability of the virus

The use of two primer couples for PCR each generating amplimers of expected size also makes it possible to verify the absence of gross rearrangements of the viral genome after integration within the segments analysed.

This element is best checked by the Southern blot which verifies the absence of major rearrangements in the absence of inadequate bands both in number and size; as well as the absence of multiple integration events within the cells derived from the same done which would suggest the presence of helper virus.

Finally, the absence of major rearrangements likely to adversely affect the construction is best appreciated by the functional assay; demonstrating the acquisition of a phenotype resistant to neomycin after chromosomal integration of the marker gene.

The efficacy of the infection has been assessed here by means of three essential parameters: 1°) the conventional viral titration which made it possible to demonstrate titers higher than or equal to $10^6$ pfu/ml. 2°) the Southern blot comparing the intensity of the signal obtained after hybridization on a hydrolysate of 10 μg of genomic DNA derived from infected cells without selection and, after selection by the drug to which the product of the transduced gene confers resistance. If theoretically calculated plasmid dilutions were added they constitute a less satisfactory standard than that just mentioned. In fact, the plasmid dilutions are such that a minor inaccuracy in handling may lead to the erroneous conclusion of a significant difference.

All of these elements added to an experiment (3°) of semi-quantitative PCR converge to indicate that the undiluted supernatant of the second clone infects the mouse fibroblasts with an efficacy close to 100%.

However instability of the titers was observed with a rapid drastic loss in the case of the first clone and a much more gradual diminution on for the best; This phenomenon is a commonplace observation in the handling of producer cells which seem to lose their initial packaging capacities with successive passages. The initial production of large quantities of cells and their careful freezing makes it possible to compensate for this disadvantage Nonetheless the titer must be systematically and repeatedly checked.

Furthermore, an amphotropic producer line was selected. However, the initial transfection of the ecotropic producer cells would have made possible the infection of amphotropic lines, possibly repeated reciprocally and repeatedly according to the "ping-pong" procedure (McLachlin J R) (by means of the supernatant filtered to prevent a possible mixing of the two cell types); this latter might contribute not only to increasing the infectivity of the resulting producer cells but also to stabilizing the retroviral titers. However, it was observed that systematically helper viruses are produced and this method can not be used in animals or in the clinic.

The quite special efficacy of this construction deserves to the emphasized, all the more since the backbone of the FB29 strain of the Friend virus differs from that which was used to establish the packaging lines. The safety of handling is still further improved since the risks of potential recombinations producing replication-competent virus are further reduced.

The introduction of a marker gene or any sense or antisense cDNA sequence or genomic DNA fragment of limited complexity (limited number of introns) of a size less than or equal to 7 kb from which will be derived a cDNA whose introns will be expelled in the targets may be achieved starting from the previously described procedure.

In the case in which the preservation of intron sequences seems essential to the production of stable transcripts, the genomic fragment of a size less than or equal to 7 kb will need to be introduced in a reverse transcriptional orientation with respect to viral transcription, at best by using a version of the construction in which the 3' LTR is deleted from the U3 and in which the genomic fragment is placed under the transcriptional dependence of a promoter and/or enhancer in the same orientation in order not to have competition between the sense transcripts dependent on the viral LTRs aid antisense transcripts dependent on the added promoter.

The introduction of a deleting of all or part of the promoter or enhancer sequences of the U3 region of the 3' LTR offers guarantees of considerable safety after integration of the retrovirus. In this case, the expression of the transgene will need to be placed under the dependence of an exogenous promoter and/or enhancer within the construction.

4) Integration sites

The study of the number of integration sites of the virus after infection of primate cells has provided very relevant information concerning the physiology of the defective viruses with high infective titers and concerning the safety of use of these viruses in therapeutic applications in man.

B) ADDITIONAL RETROVIRAL CONSTRUCTIONS

B1) GENERAL CONCEPTION AND VERSATILE USE 1) self-Inactivating Retroviral Vector (SIN); designation: FOCH29-del U3 shown in FIG. 6.

In the light of the physiology of the replication of the genomic genetic material of the retroviruses, the modifications intended to delete the enhancer viral sequences of transcription were introduced at the 3' LTR; viral replication led at the level of the target cell of the infection to an integrated provirus whose two LTRs were generated from sequences of the initially 3' LTR This deletion was hence made on the plasmid containing the BamHI-BglII fragment including the 3' LTR sequences. The resulting BamHI-BglII fragment shortened by 339 bases was excised and ligation with the plasmid containing the 5' LTR and the adjacent sequences was carried out according to the same procedure as for the basic vector. In fact, the enhancer sequences of the 5' LTR were left untouched in order that the viral transcription could occur and form "readthrough" transcriptions; infectious virus particles were thus formed at the level of the packaging line.

The construction design chosen leaves in place the TATA box but removes the CAAT box (Yu et al., 1986) by cutting using the enzyme BssHII (unique site at 8203 of the sequence of the native virus) which excises the CAAT box; the protruding 5' cohesive ends generated by the enzyme BssHII are made "blunt" by filling in using the Klenow fragment of the DNA polymerase I in the presence of deoxynucleotides.

The restriction enzyme used upstream was:
either EspI (=iso-CelII) at position 7864, situated immediately after the start of the inverted repeat (IR). The protruding 5' cohesive ends generated by the enzyme EspI were made "blunt" by filling in using the Klenow fragment of the DNA polymerase I in the presence of deoxynucleotides.

or EcoRV at position 7984 in the middle of the direct repeats which the cut interrupts; the ends generated by the enzyme EcoRV are blunt.

Since the ends upstream and downstream have both been made blunt, direct ligation was possible to close up the construction, henceforth bearing a large deletion in the U3 region.

The first version del U3 (deletion EspI at 5'/Iso CelII at 3') was studied in functional terms: viral infection and integration and residual expression. The deletion created here has removed practically all of the U3 sequences of the virus. This is ideal in terms of safety of the retroviral construction.

We have been able to show that viral transcription was not adversely affected in the packaging lines by introducing the beta-galactosidase marker gene with a nuclear localization signal in this construction. In fact, the producer cells took on a blue colour after transfection which confirms not only the presence of the gene borne by the retroviral construction but also the expression of this transgene.

The viral integration was investigated by molecular methods, in particular by PCR using the following primers: oligo-SENSE situated in the beta-galactosidase gene with the following sequence: 5'-CGA CTC CTG GAG CCC GTC AGT ATC-3'(SEQ ID NO: 7) oligo-ANTISENSE situated in the viral LTR, overlapping between R and the start of U5 (LTR-508): 5'-CAG CGA GAC CAC GAG TCG GAT GC-3'(SEQ ID NO: 8) in a region which has been prepared by EspI/BssHII deletion.

Alternative constructions consist for example of inactivating the viral enhancers as in the case of the deletion with EcoRV, even of making shorter deletions leading to the retention by the virus of a background transcriptional activity in the target cells of the infection. On the other hand, a deletion removing the TATA box in addition to the sequences described in the version called the first version of IU3 represents an additional security device; however, considerable reduction of titers may occur when such constructions are formed (Yee at al., 1987).

SIN CONSTRUCTIONS WITH INTERNAL PROMOTERS

An internal promoter which can be used to create these constructions is for example the promoter of the receptor for the EGF (Epidermal Growth Factor) derived from the plasmid pERCAT2DE(c) (Maekawa et al. 1989): only the promoter sequences situated upstream between the nucleotides −2200 and −15 (EcoRI-SstI fragment of 2.2 kb) were selected. The enhancer sequences downstream contained in the plasmid pERCAT2DE(C) were not included. Another promoter is the ubiquitous PGK promoter (phosphoglycerate kinase).

2) Definitions of the Existing Constructions

Figure 7:
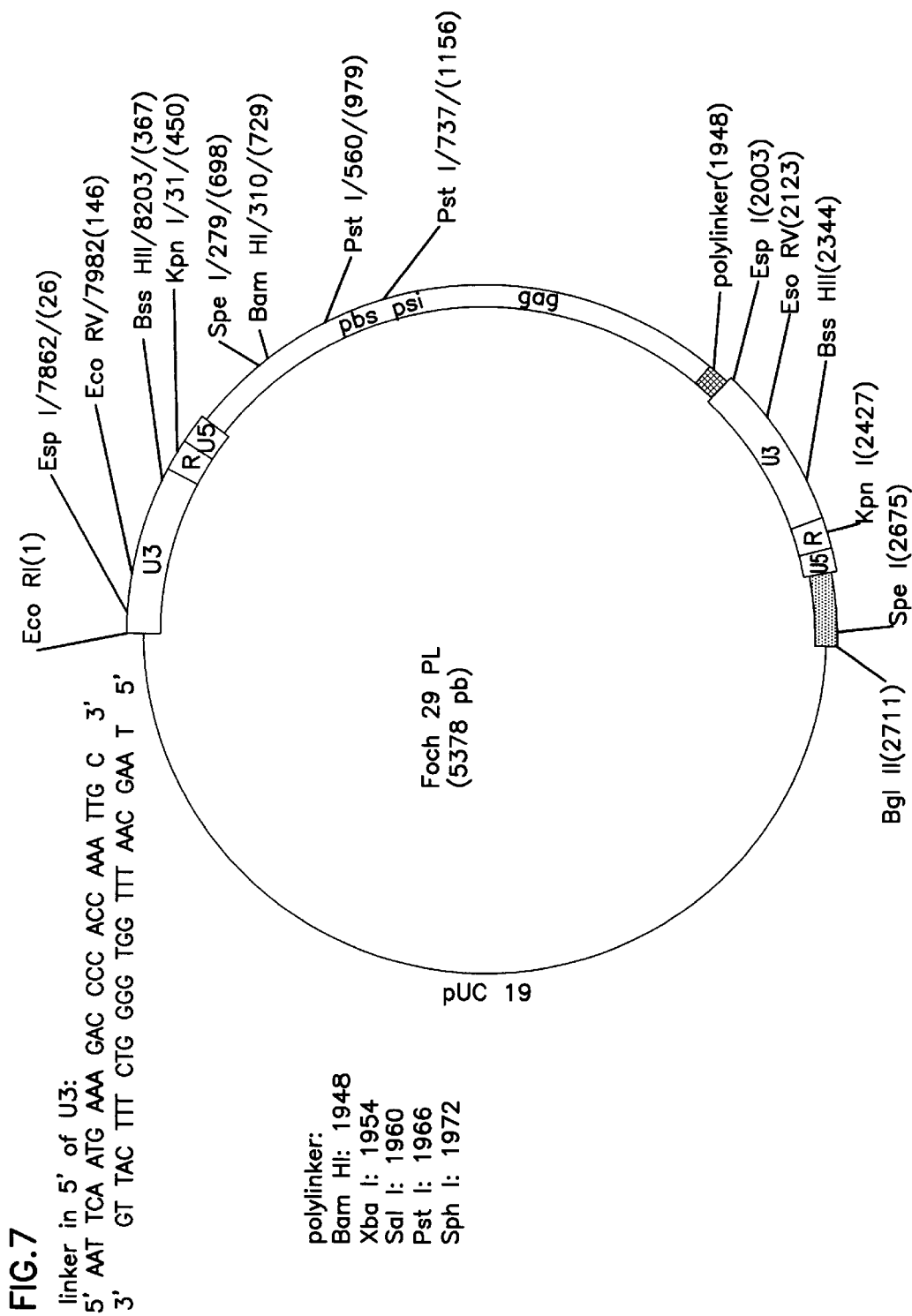

2°-1 A construction was made with a still more reduced LTR upstream from the 3' LTR in particular; designation FOCH29-PL (for FOCH29 pure LTRs) shown in FIG. 7.

This construction made it possible to assess the advantage in terms of genetic stability of the excision of the 140 bases, including 104 of the end of the envelope upstream from the viral LTRs.

The construction was made from the plasmid pUC19 including the EcoRI-PvuII fragment described in part B1-1: enzymatic cutting by the restriction enzyme EspI (or IsoCellI) at position 7864 (namely +23 of the viral LTR). At the 5' end the bases generated by a EcoRI cut were artificially added to a double stranded synthetic oligonucleotide complementary to the 23 bases of the LTR (140 bases, 103 of which are bases of the envelope). At the 3' end the oligonucleotide is complementary to the cohesive SpeI ends. The oligonucleotide sequences are the following: oligo-SENSE 5'- AAT TCA ATG AAA GAC CCC AAA TTG C-3'(SEQ ID NO: 9); oligo-ANTISENSE 5'-TAA GCA ATT CGG TGG GGT CTT TCA TTG -3'(SEQ ID NO: 10).

Figure 8:
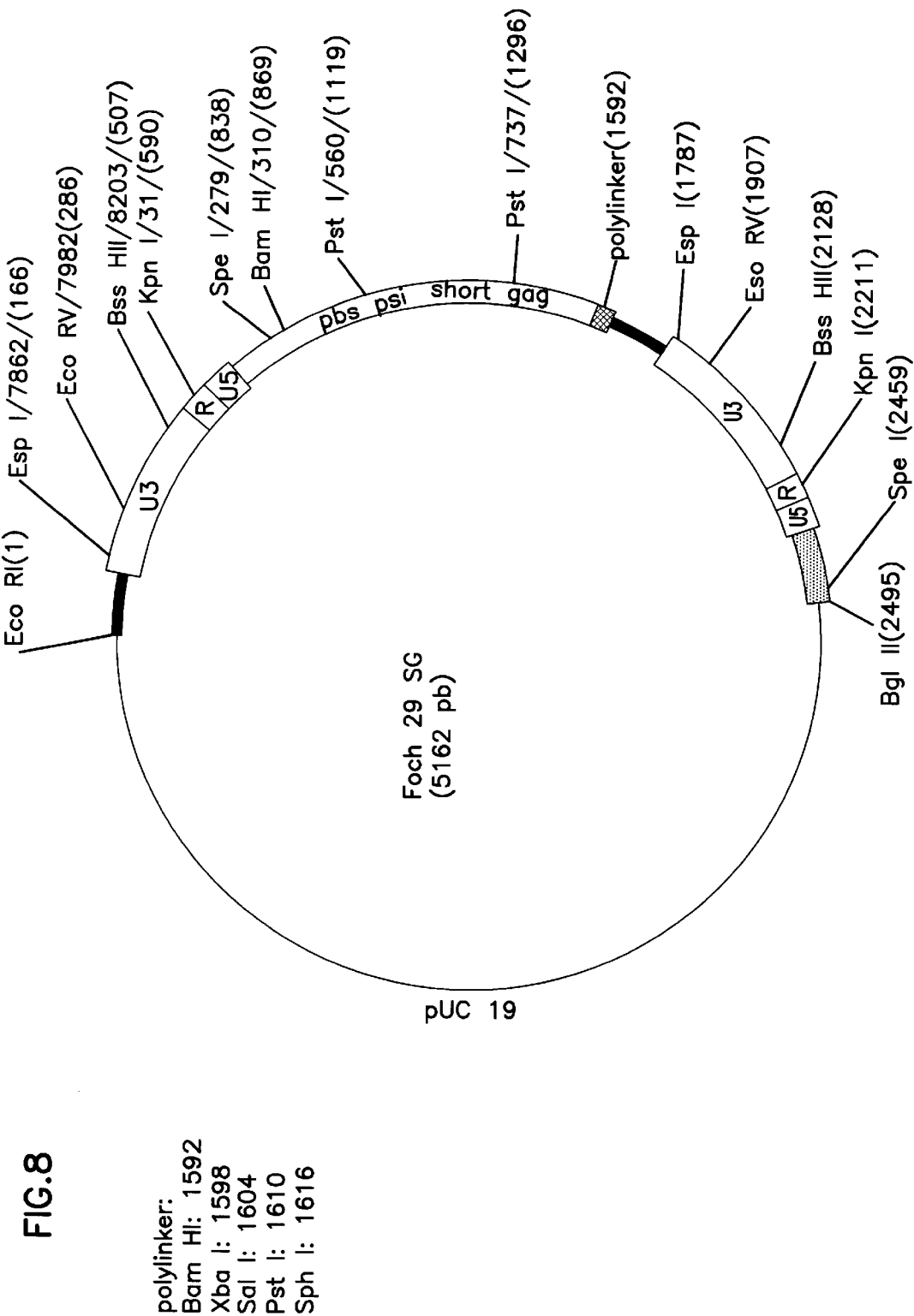

2°-2 GAG shortened while preserving intact the packaging sequences; designation FOCH29-SG (for FOCH29 short GAG) shown in FIG. 8.

The basic construction FOCH29 leaves half of the GAC sequences in place; the transcription and probably the translation of Map15 and pp12 being preserved.

The preservation of a significant portion of GAG has been described as being beneficial for the stability of the retroviral construction. This may however represent a disadvantage in terms of the space available for the exogenous sequences to be vectorized, on the one hand; and on the other, in terms of safety of the construction, the probability of promoting recombinational events with retroviral sequences to generate replication-competent viral particles being significantly increased.

FOCH29 contains scarcely more than half of the GAG sequences of the FB29 strain and offers the advantage of very remarkable efficacy.

A culture of the producer clones of FOCH29, maintained for 18 months, did not lead to the production of an amount of recombinations with retroviral sequences generating replication-competent viral particles and thus detrimental to the safety of its use.

In this perspective of improving viral safety, an alternative construction was prepared in which the GAG pf FBb 29is cut at the unique AhaIII (or isDraI) site at position 1031 (SEQ ID NO:16); only a quarter of the GAG sequences are then conserved. The cut generated by AhaIII having blunt ends as for PvuII used for the cloning of FOCH29, the construction was made exactly superposable, the cloning upstream not being modified; downstream, the blunted ended SmaI site of the polylinker of pUC19 was used.

2°-3 Constructions including IRES (for Intra Ribosome Entry Site or Ribosome Landing Pads) leading to polycistronic messenger RNAs.

A retroviral construction including IRES is in principle designed for the transfer of several genes of interest for which it is desired that the level of transcription is balanced since it is initiated from a single promoter (Morgan et al., 1992); the most illustrative example is that of the transfer of the sequences coding for the different chains of a functional molecule in a heterodimeric or trimeric, context.

A polycistronic vector was constructed for the transfer of the two chains of interleukin 12 or IL12, p35 on the one hand and p40 on the other.

The p35 fragment introduced was the following fragment: at 5': PstI at position +187 of the sequences; of the two ATG (Met) codons in phase (positions 100–102 and 202–204), that used was at position 202–204; and at 3': EcoRI at position +1065 (stop codon TGA at position 904–906).

The p40 fragment introduced lacked the flanking 5' or 3' sequences: XbaI site at position +1 of the sequence (ATG at position +9); and at 3': EcoRI at position +1007 (stop codon TAG at position 993–995). The complementary DNA to p,40 has an optimized AUG codon (Sequence Kozak CCATGG; corresponding to the NcoI restrictions site).

Two types of IRES were used (Borman et al., 1992; 1993);

IRES derived from poliovirus which required accurate positioning; ribosome binding site at 560, AUG binds to position 743.

This is the fragment KpnI (position +70)/BarI (position +630) which was used: either upstream of p35 (FOCH29-NHRIL12); or upstream of the gene for or resistance to neomycin (FOCH29-IL12-30IR4ON).

IRES derived from EMCV (for EncephaloMyoCarditis Virus), in which the IRES sequences derived from EMCV require extremely accurate positioning, in phase, of the gene to be expressed (IRES sequence derived from EMCV are sold under the name of pCITE for CAP INDEPENDENT TRANSLATION ENHANCER (Novogen, USA), very similar to those which were used here). In the light of the optimized character of the AUG of p40 it is this chain which was associated with the IRES-EMCV whatever the construction; the EMCV fragment used comprises a EcoRI site upstream (position +280) and a NcoI site downstream situated just after the AUG leave a "C" residue which corresponds to the second base of the fourth codon).

Figure 9:
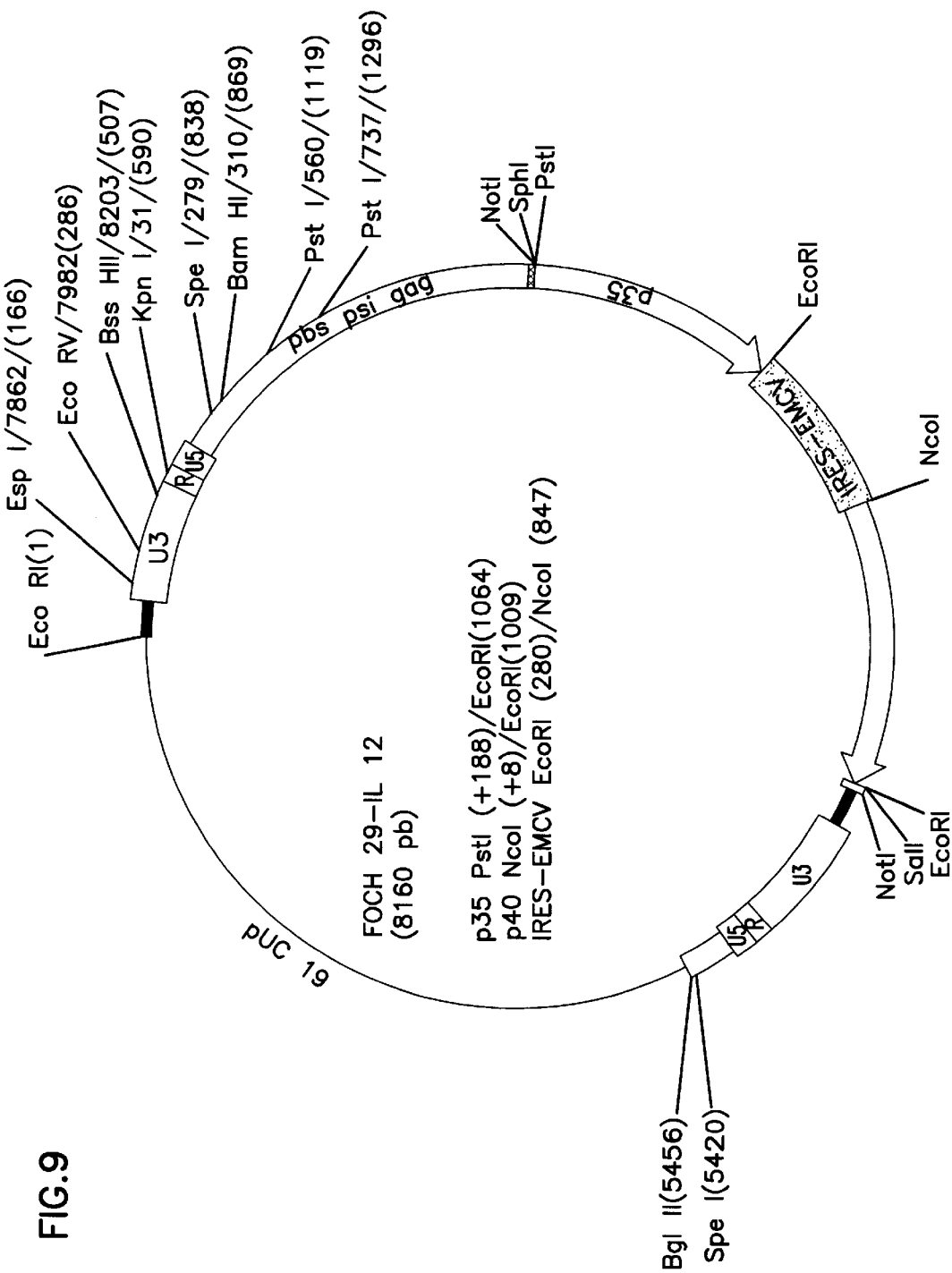

Three constructions were made:

FIG. 9 1) FOCH-IL12: p35/IRES of poliovirus/p40: LTR promoter

Figure 10:
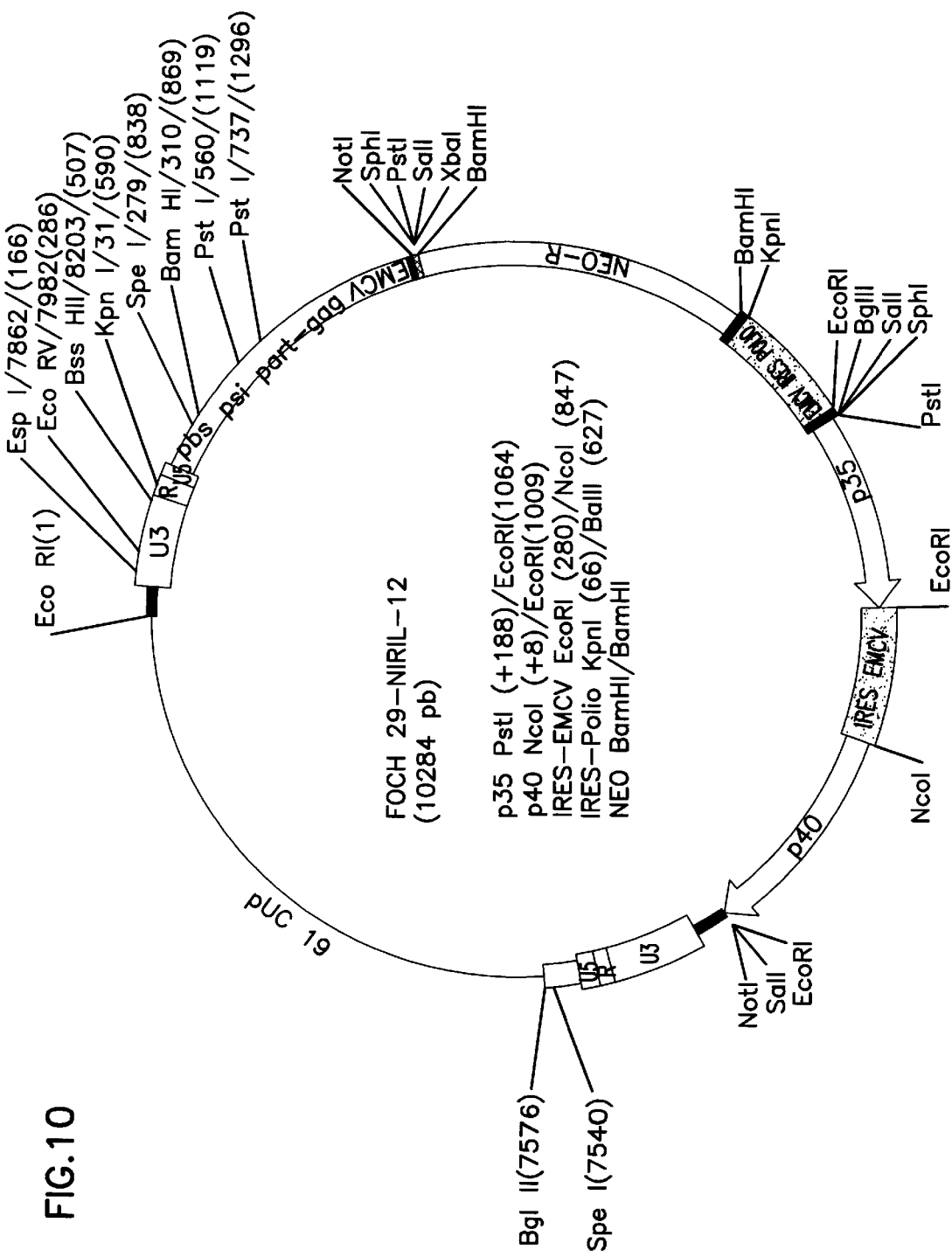

FIG. 10 2) FOCH29-NIRIL12: neomycin resistance gene/IRES of poliovirus/p35/IRES of EMCV/p40

Figure 11:
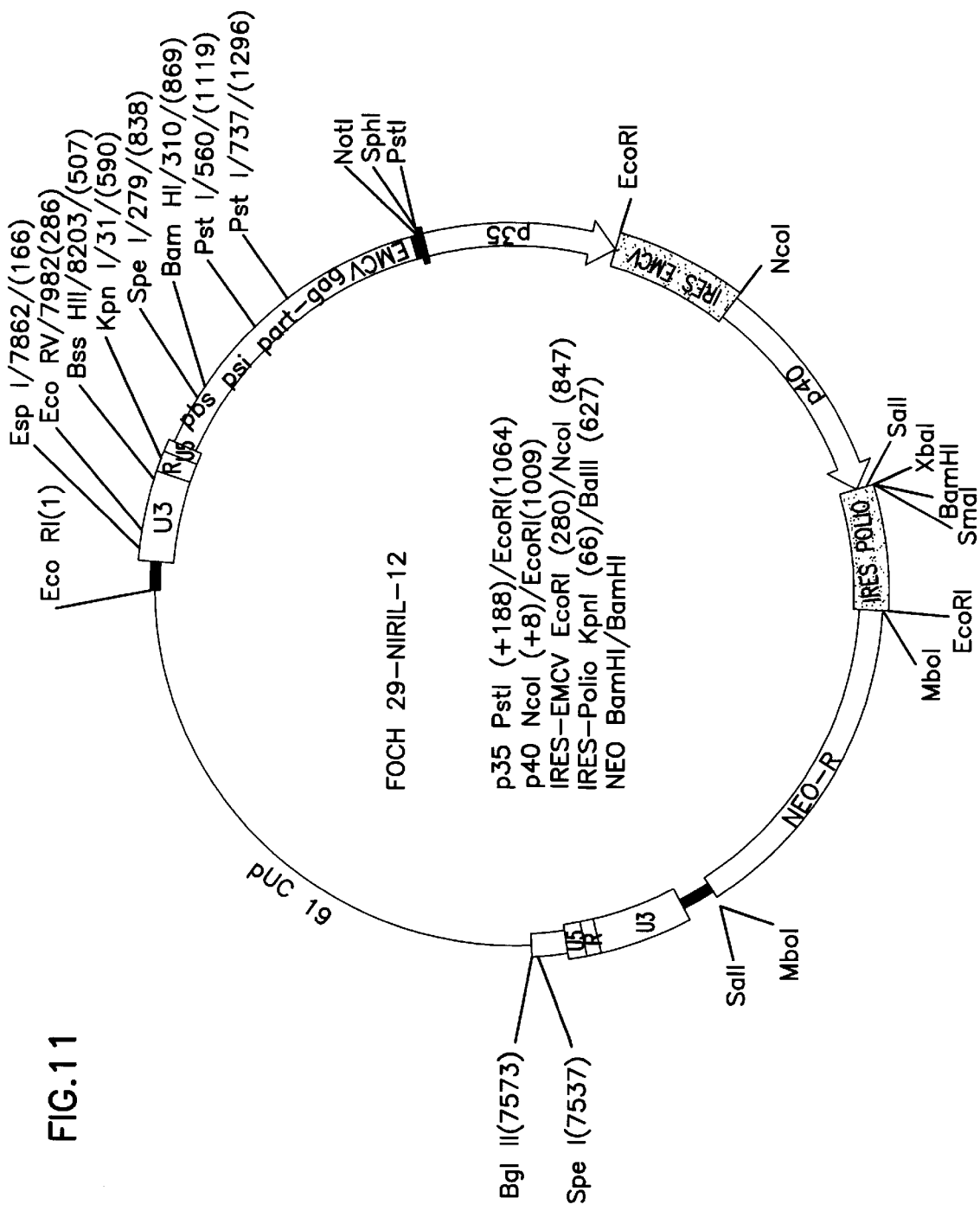

FIG. 11 3) FOCH29-30IR40N: p30/IRES of EMCV/p40/IRES of poliovirus/neomycin resistance gene These constructions all have resort to an intermediate construction an in pUC18 in which:

1°) a NotI site was introduced at each of the ends of the polylinker, in HindIII upstream and in EcoRI downstream;

2°) a SalI site was introduced downstream from the polylinker between the EcoRI site and the NotI site 3°) a base motif ("pUC18-base") was cloned comprising: p35IRES of poliovirus/p40. Starting from this base motif, the construction FOCH-IL12 was obtained by excision by means of NotI digestion; ligation is carried out between the fragment obtained and the vector FOCH29 opened by NotI for which a linker was introduced at the XbaI site.

The constructions FOCH29-NIRIL12 and FOCH29-IL12-30IR40N were obtained after addition respectively: of the block neomycin gene resistance/IRES of poliovirus at the SphI site upstream from the "pUC18-base"; and the block IRES of poliovirus/neomycin resistance gene at the SalI site downstream from the "pUC18-base".

2°-4 Construction GAG-POL to contribute to the development of an original packaging line.

The nucleocapsid proteins and the reverse transcriptase are derived from sequences of the FB29 strain in the complementation line.

The packaging lines presently available and derived from mouse cells possess the following disadvantages:

Co-packaging, concomitant with defective constructions, of endogenous retroviral sequences (MCF, VL30, even retro-transposons). These co-packaged sequences are thus also likely to be integrated after infection of the target cells of the transfer.

Expression of complementation proteins in particular the envelope, piloted in these lines by a retroviral LTR. Although the lines of the third generation use complementation retroviral constructions comprising several mutation or deletion sites, the preservation of LTR sequences is in itself a potential disadvantage; in fact, they are capable of giving rise to genetic recombination with the defective constructions to be complemented.

All of these, elements have led to attempts to improve the safety of conditions of genetic transfer with retroviral vectors. The packaging line was developed on the principle of the third generation lines; i.e, with fragmentation of the sequences coding for the complementation proteins in two parts (two successive transfection step).

2°-4-1 In the first stage, the steps implying the use of sequences derived from the FB29 strain of the Friend virus, are described: in particular, development of the basic cell "DOGF29".

DOGP29 was obtained by transfection of the construction LTR-SD-deletion psi-GAG/POL detailed below (and co-transfection with selection gene, resistance to phleomycin) on dog fetal cell optimized according to the following criteria: 1-absence of endogenous retroviruses; 2-adherent cell; 3-rapid growth; 4-stable and homogeneous morphology;5-easily transfectable; 6-very high number of passages tolerated (intensive artificial passages for assay); 7-optionally capable of sustaining LTC-IC (Hemato).

A Master Cell Bank System is created from the done of dog cells selected according to the intensity of synthesis of viral complementation proteins and the stability of expression of the reverse transcriptase (POL).

The complementing gag/pol construction for the nucleocapsid proteins and the reverse transcriptase is derived from the FB29 strain of the Friend virus.

The basic construction was assembled from the construction described in the paragraph in which the LTR was left in place or replaced by the sequences of the RAR-beta promoter.

A large deletion of the packaging sequences situated upstream from the sequences coding for the gag capsid nucleoproteins (starting at +619) is carried out as follows: SpeI (or IsocelII) cut, unique site at +280; and PstI at +560–561 which removes 280 bases. A synthetic linker SpeI-PstI is synthesized: 5'-CTAGTGCA-3 and annealed to the plasmid, cut again by HindIII Ligation is then carried out with the third fragment PstI-HindIII including the major part of the GAG and POL sequences.

Then, in a second step (after transformation and selection of the positive recombinants), the PstI-PstI (561–737) including the ATG of GAG was cloned at the PstI site in its original position in order to reestablish the totality of the GAG sequences; the orientation of the cloning of this small symmetric PstI-PstI fragment is established by enzymatic digestion with HaeII (position 720; a second site is situated at 4291 but does not disturb the orientation/AhaIII (unique site in the entire FB29 sequence at position 1031) or EspI (unique site in the entire FB29 sequence at position 7864 of the LTR). As a result of the method used for the cloning at the HindIII site of pUC19 of the DNA sequences corresponding to the entire FB29 genome the end of the POL sequences was recovered as follows: initial cut by HindIII (5060) and SnaI (=iso Bst11071) (unique site at 6335); after purification, this fragment was cut again by SmaI (6079) to produce a fragment of 1019 bases comprising a minimum of envelope sequences (244 basest. This fragment was subcloned in the HindIII-HincII of the polylinker OF pUC18. The polyadenylation signal of SV40 was juxtaposed downstream (excised from the plasmid pCRIPgag-2, Danos and Mulligan, 1988) from the construction. The POL and polyA sequences were excised as a unit from pUC18 and ligation was carried out with the plasmid pUC19/partially deleted LTR/del-psi/GAG/2/3-POL, described in the above paragraph.

2°-4-2 The conventional amphotropic envelope sequences, similar to those used in the psi-CRIP line were used for sequence complementation with transcription under viral 5' LTR with a polyadenylation site downstream from SV40 as in the psi-CRIP line (Danos and Mulligan, 1988).

B.2. INCLUDING GENES OF INTEREST

Whether they are constructions:

using the basic vector with its native LTRs or the SIN version from which the viral enhancers are deleted using various internal promoters for the constructions derived from the SIN vector positioning the gene of interest in a sense or antisense transcriptional orientation with respect to viral transcription.

Figure 12:
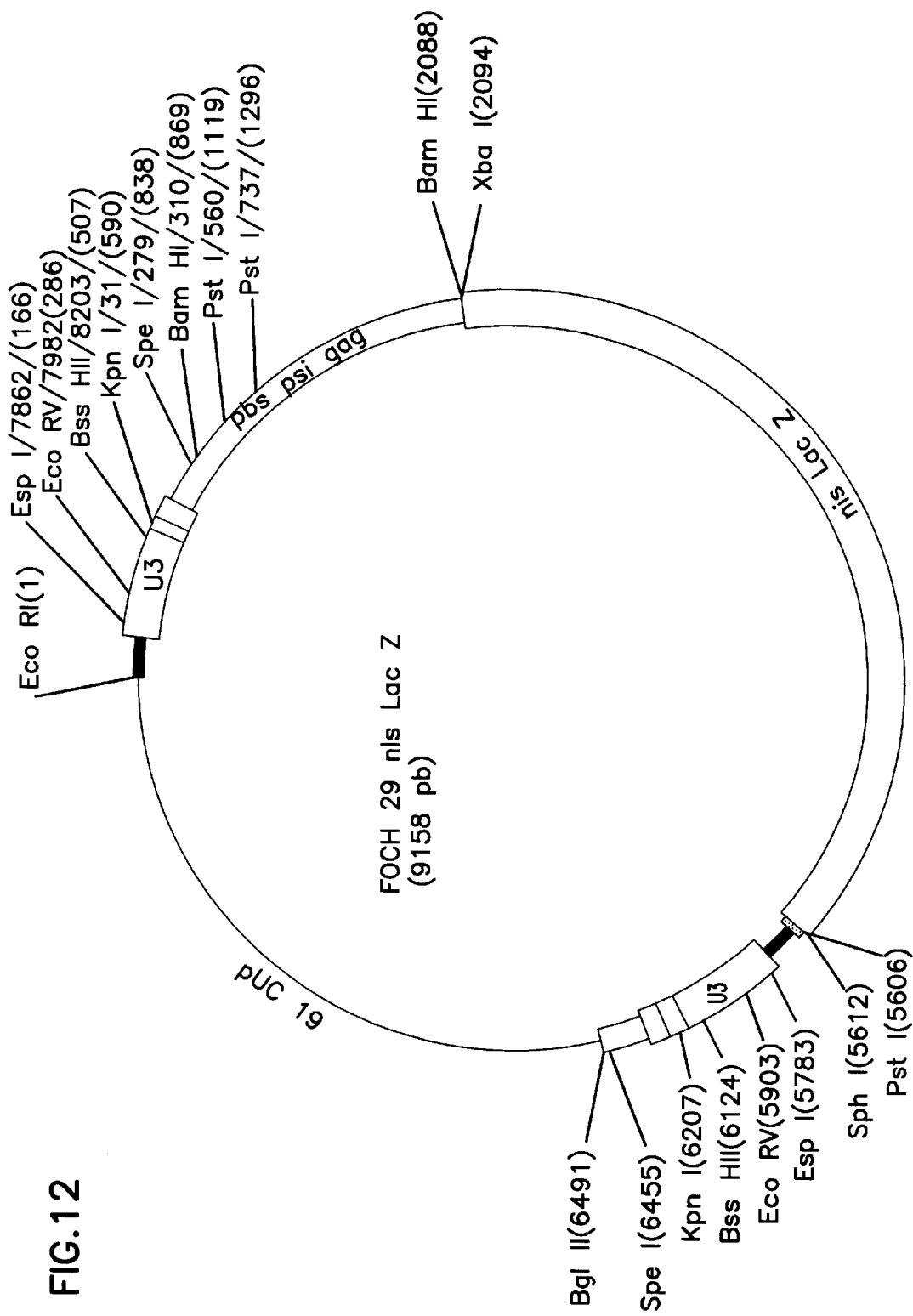
Figure 13:
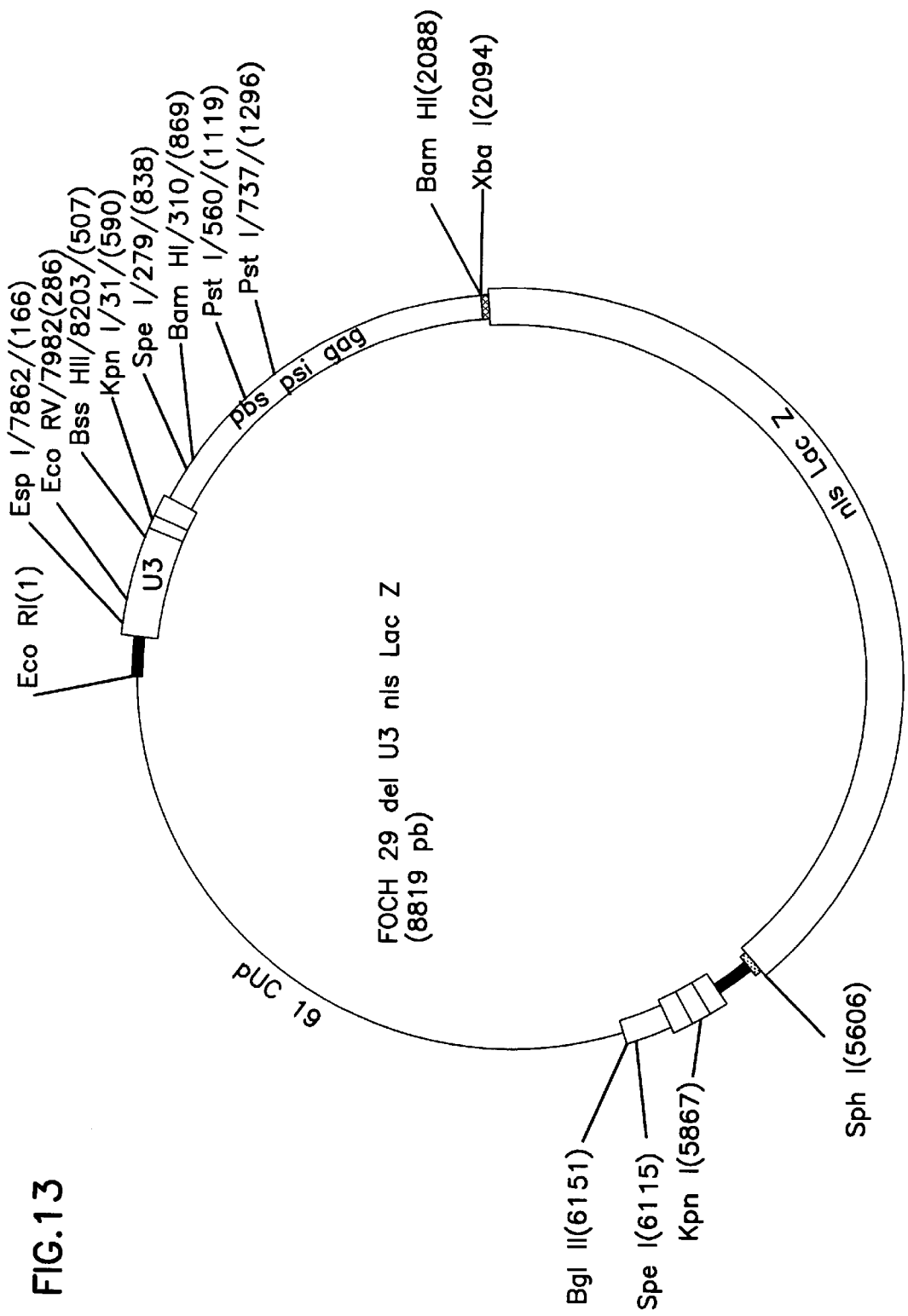
Figure 14:
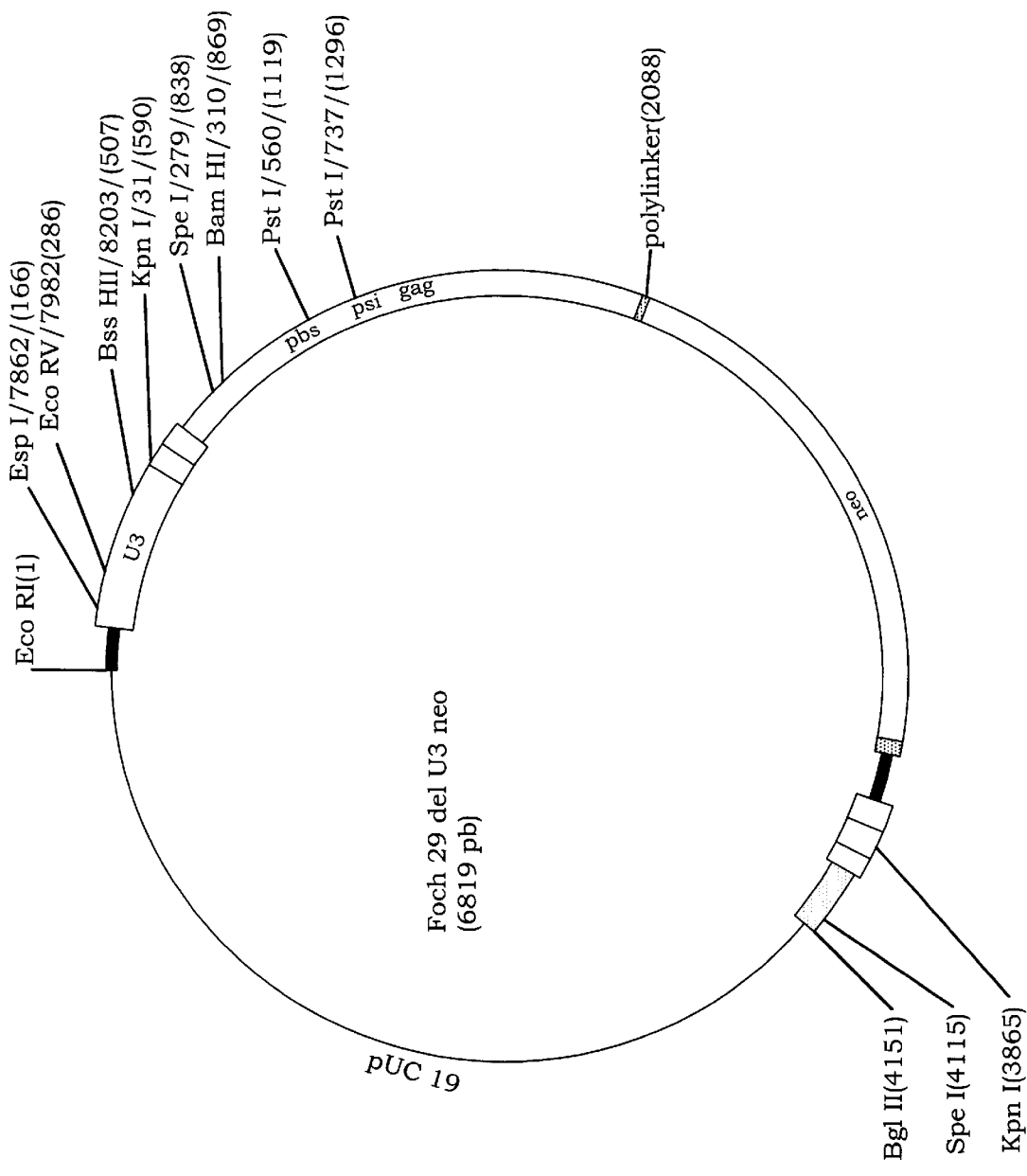

1°-cDNA coding for the beta-galactosidase with a nuclear localization signal (FIGS. 12, 13)

Figure 15:
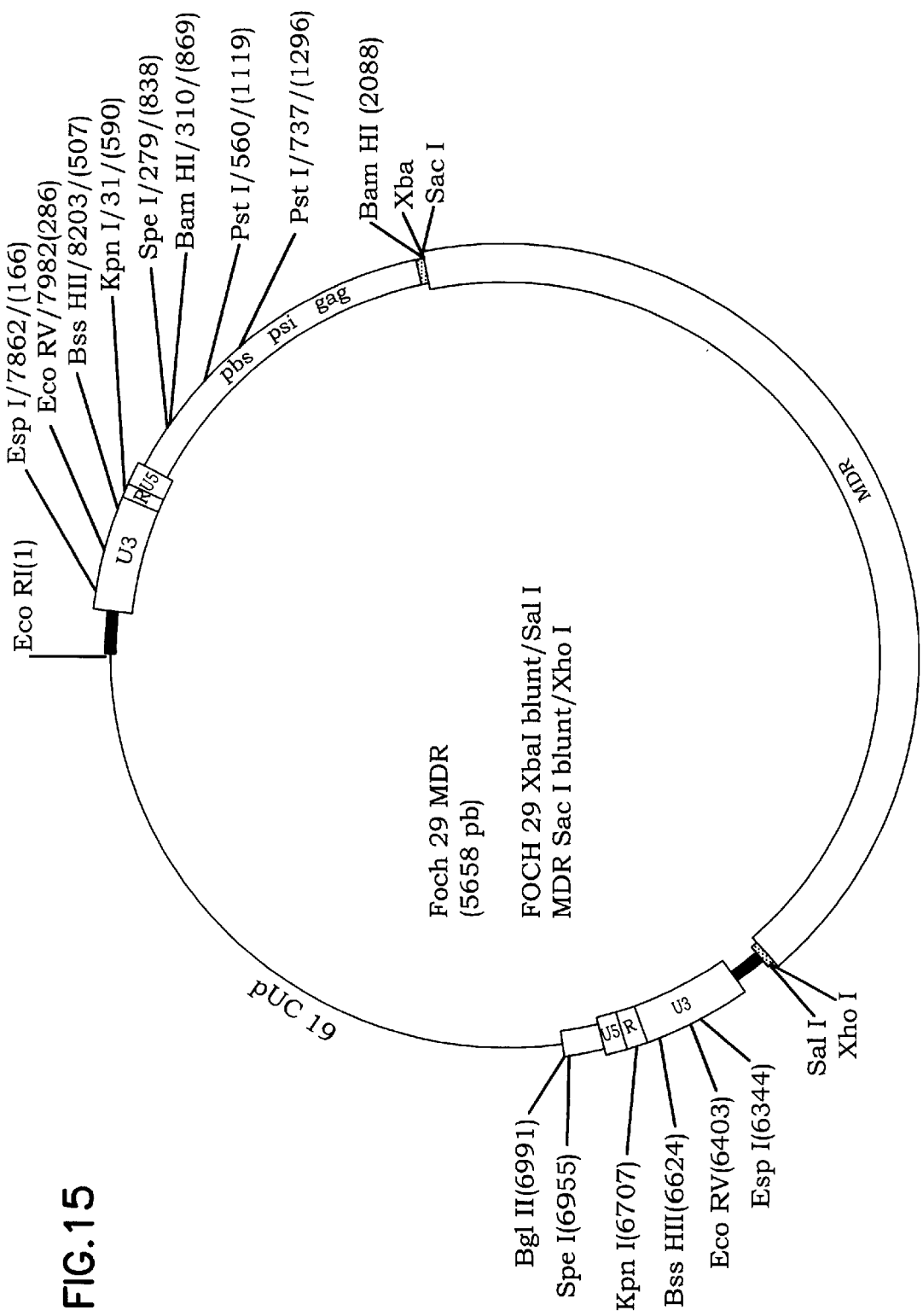
Figure 16:
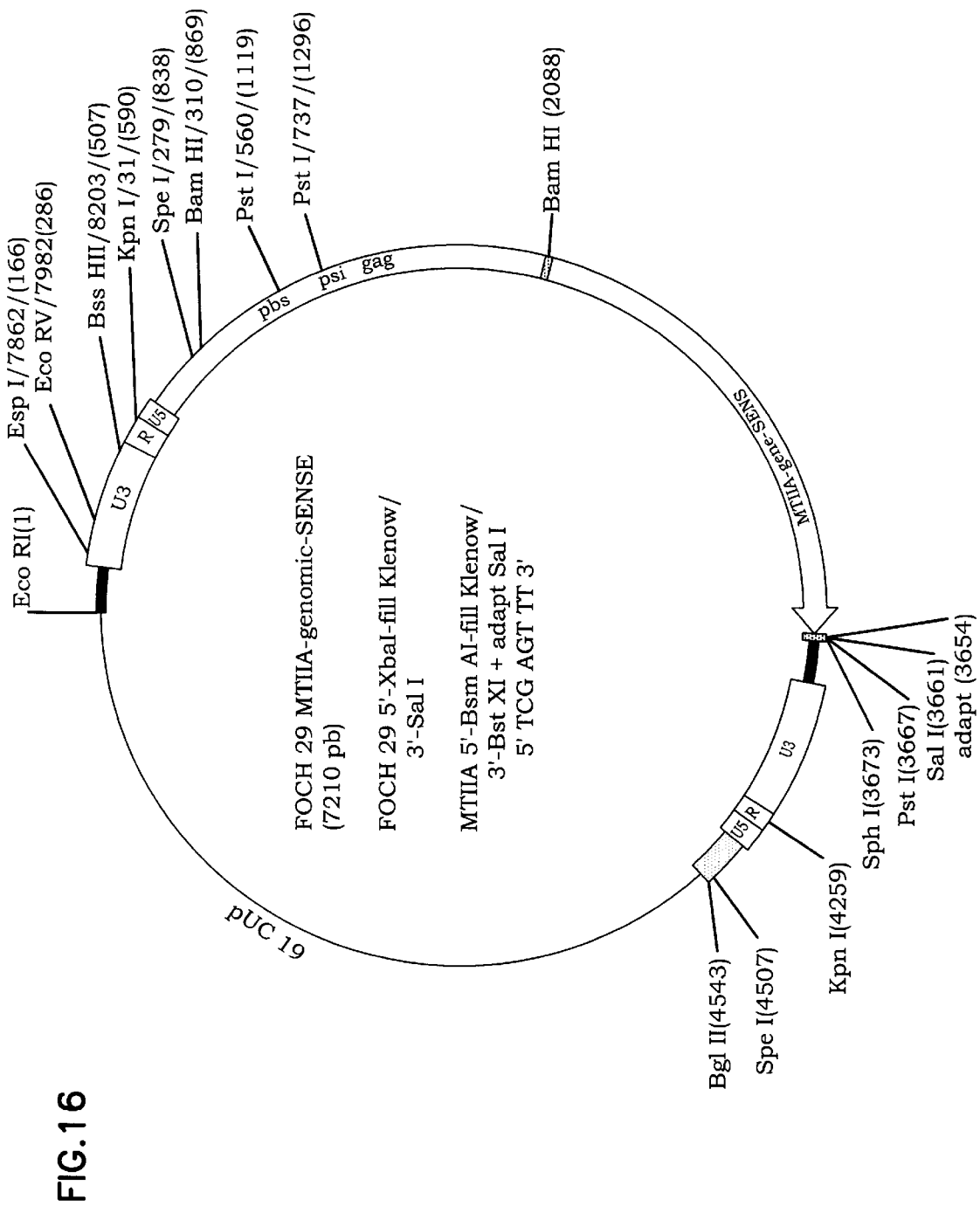
Figure 17:
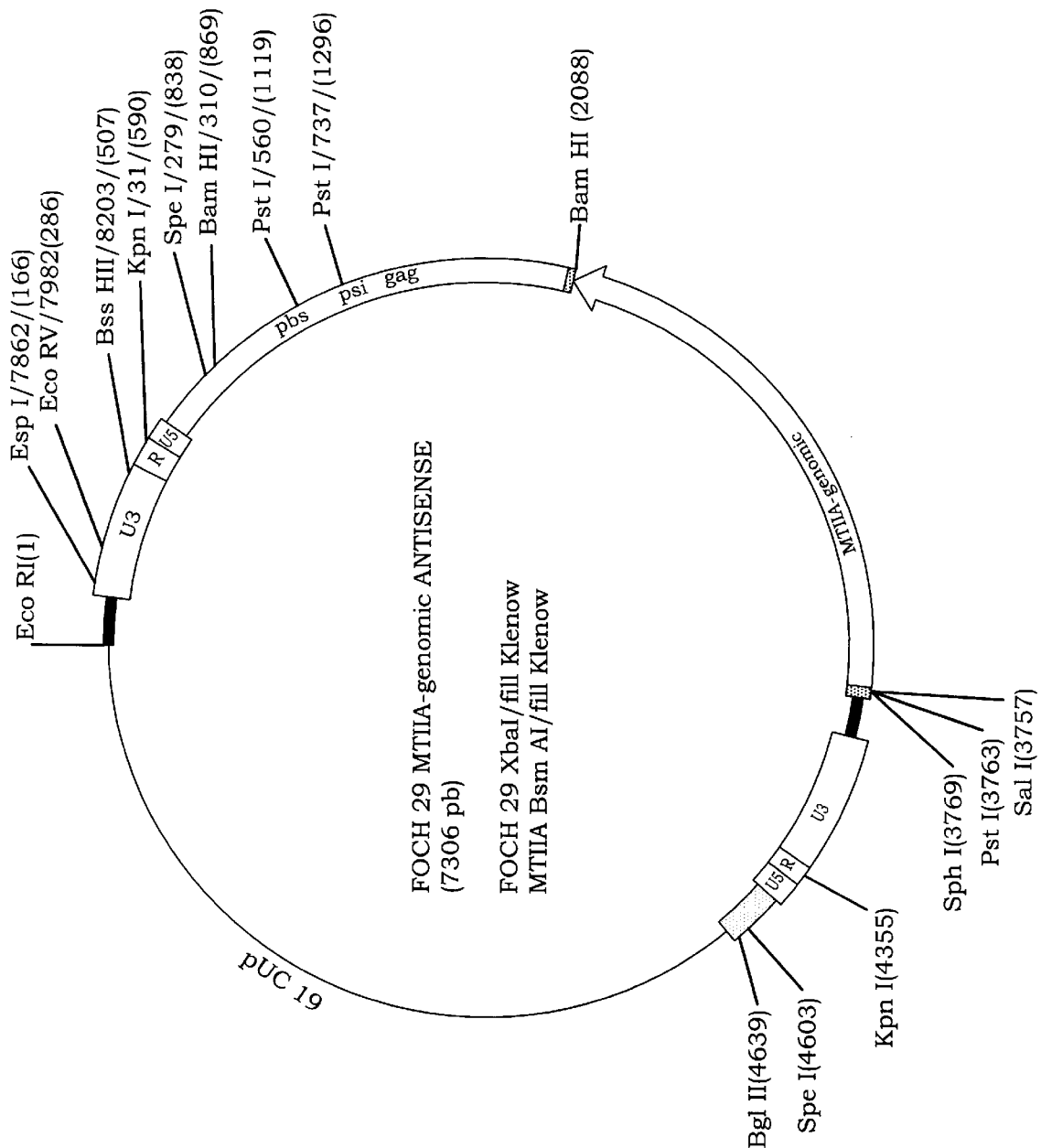
Figure 18:
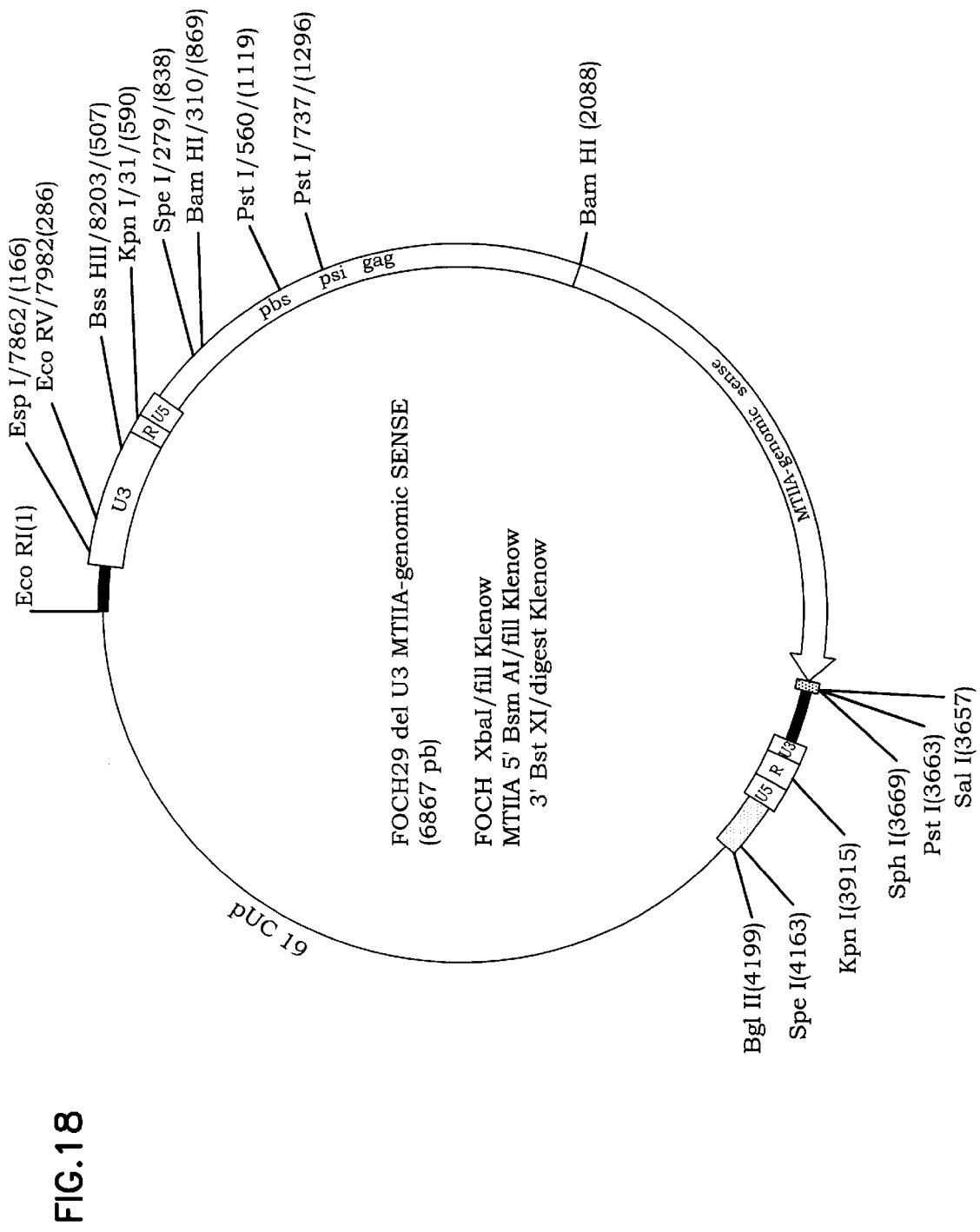
Figure 19:
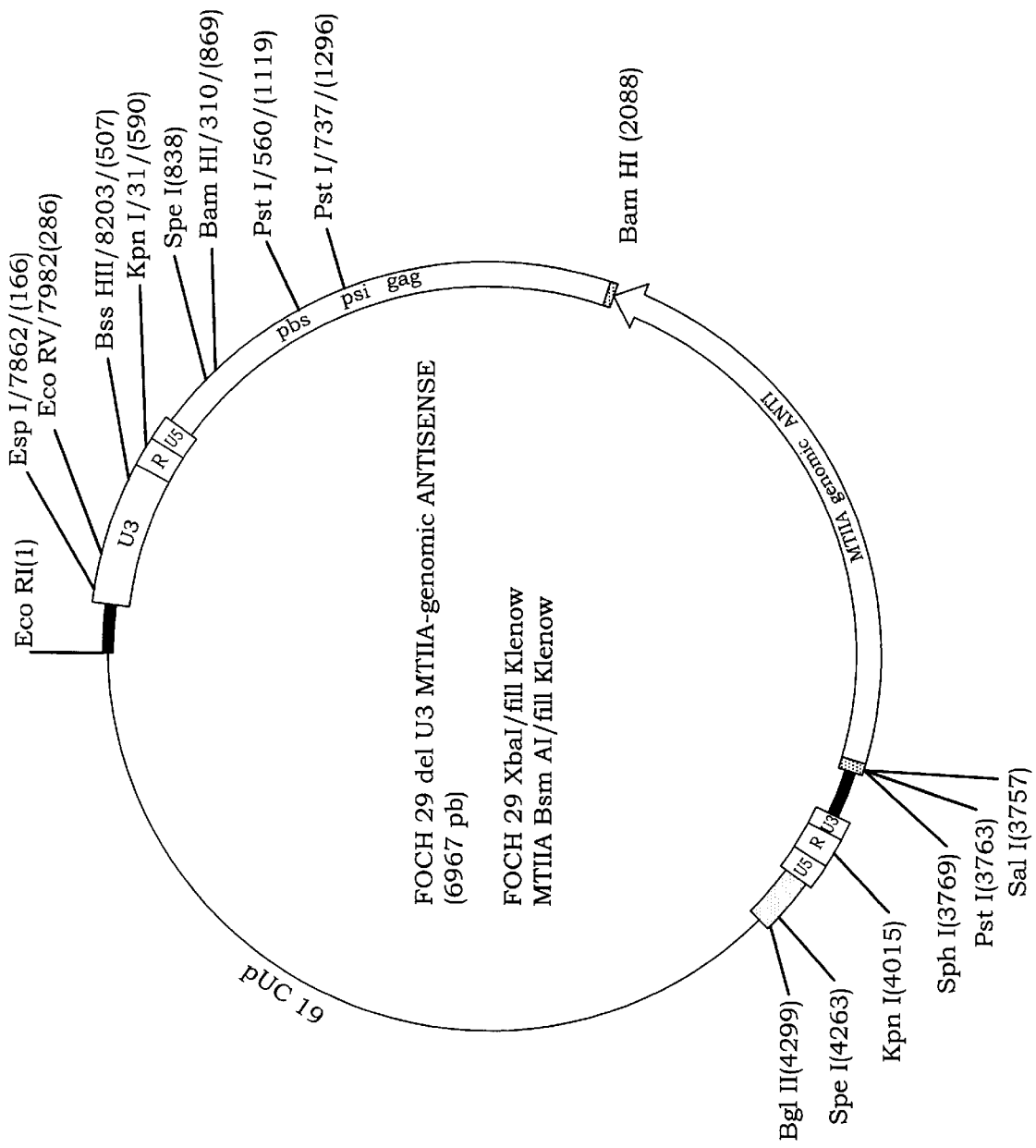
Figure 20:
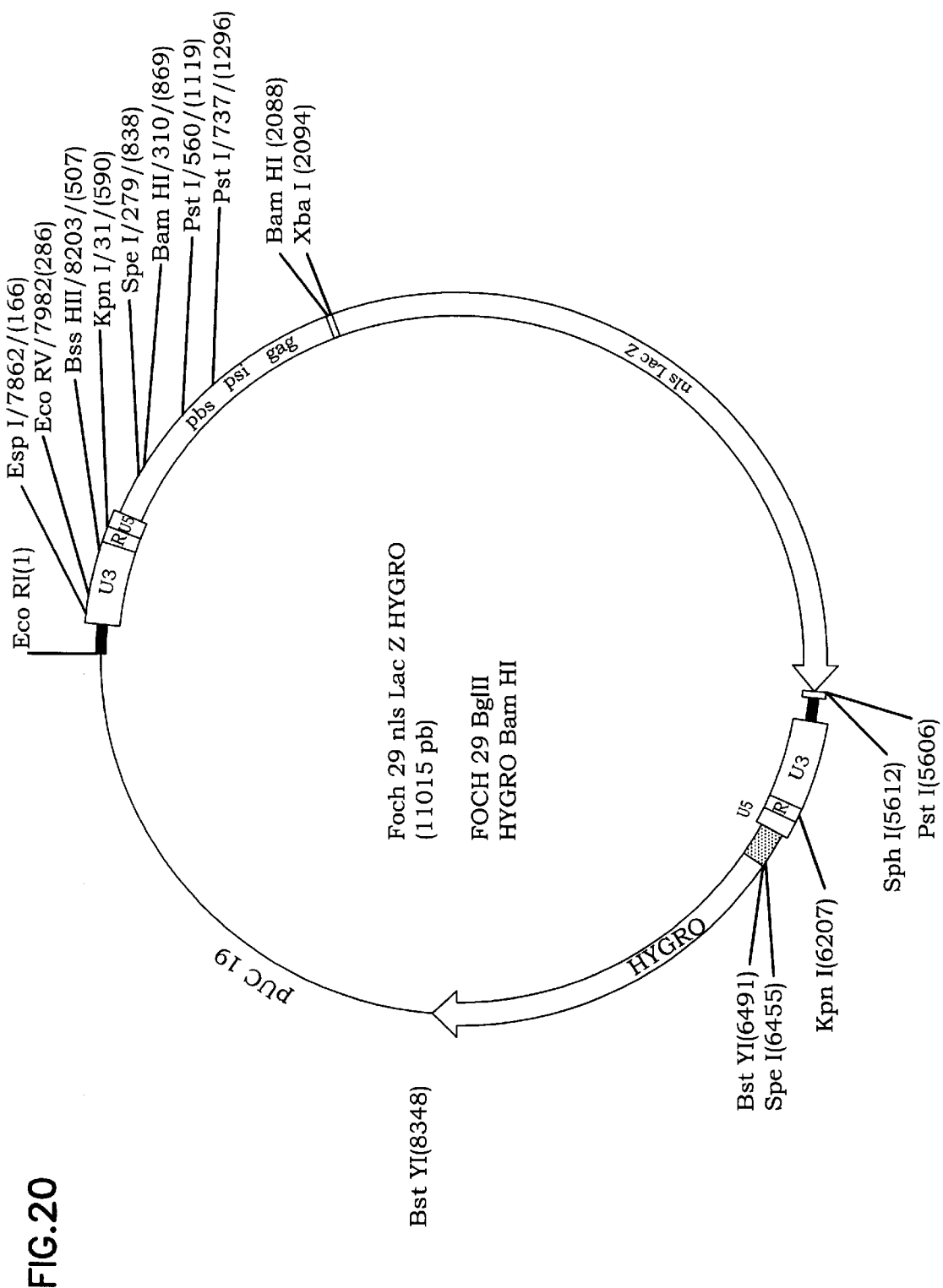
Figure 21:
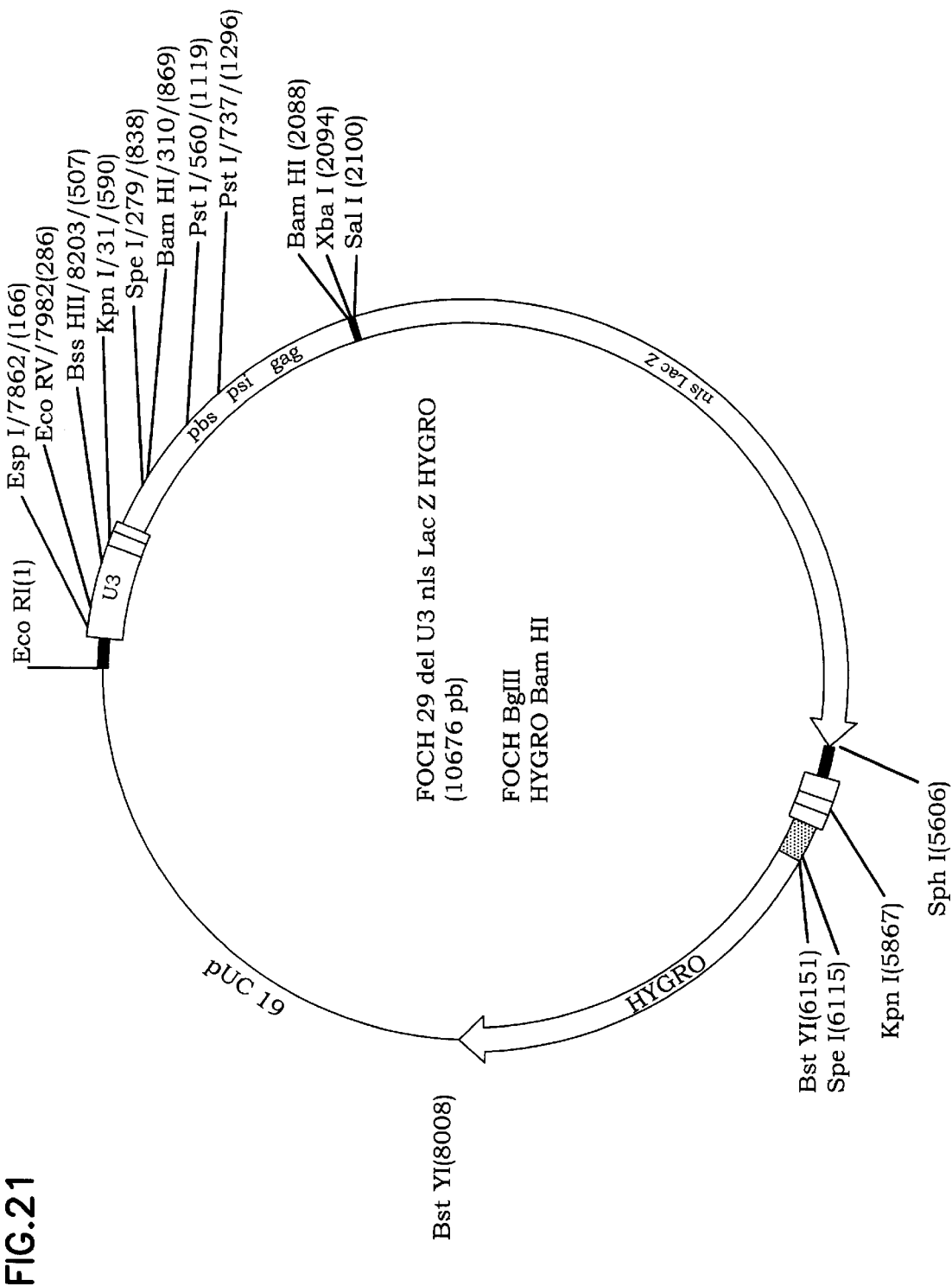
Figure 22:
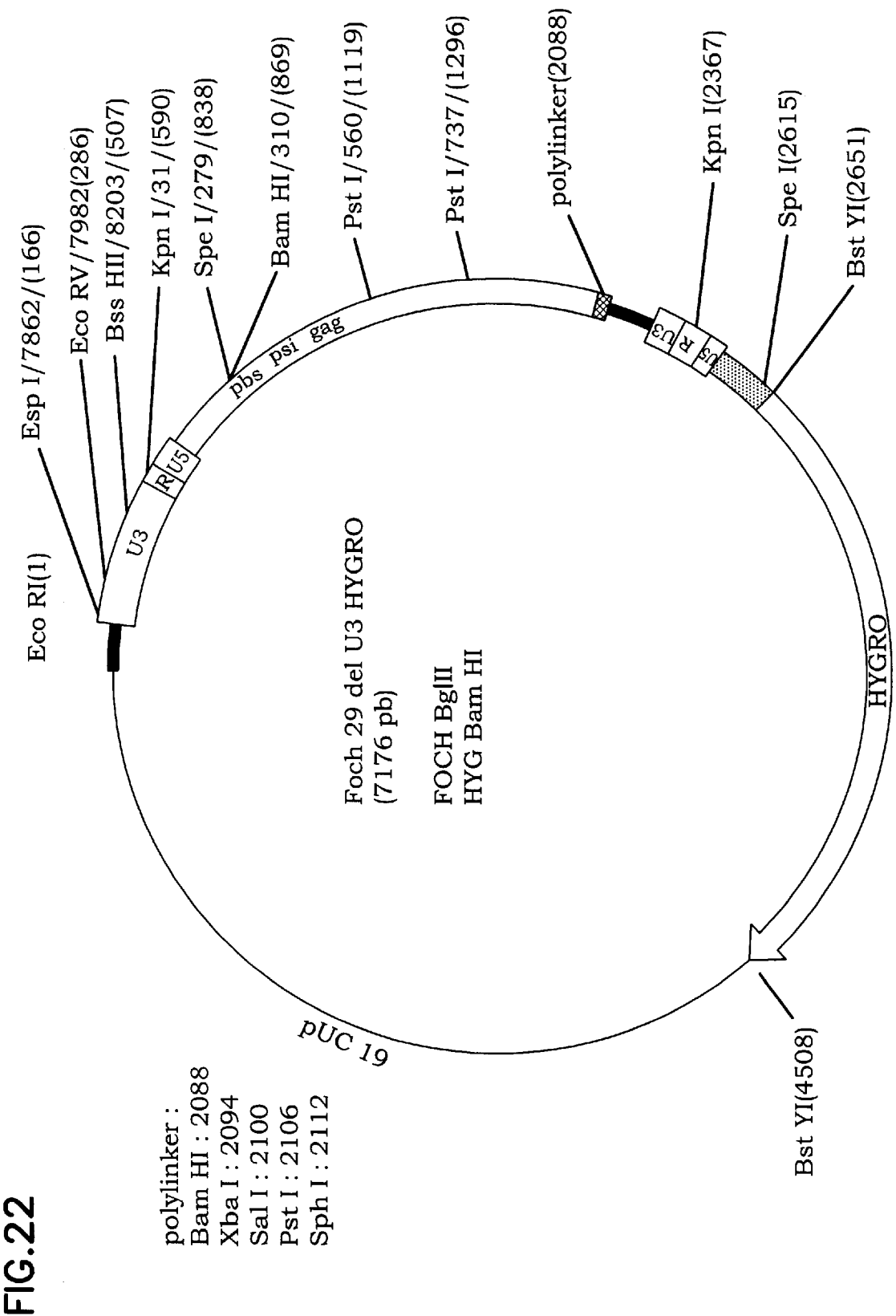

2°-cDNA coding of gp170 derived from the gene for pleiotropic resistance to cytotoxic drugs (ex insert derived from pMDR1) (FIG. 15)

3°-Genomic sequences and cDNA coding for metallothionein IIA (FIGS. 16, 17, 18, 19)

4°-cDNA of the FACC gene with or without its promoter elements, deficient in patients suffering from Fanconi disease of the complementation group C The FOCH29 retroviral backbone was used:

either in its native version with transcription defined by the activity of the viral Long Terminal Repeats (LTRs). This construction makes it possible to assess the efficacy of the LTRs of the Friend virus to express the FACC gene in hematopoietic cells.

b)- or in the del-U3 version on of the viral enhancer which makes it possible to test the advantage of a transcriptional command by an internal promoter derived from a ubiquitously functioning gene with a moderate but stable basic function: it is either the promoter of the FACC, gene itself or the MT IIA (metallothionein IIA promoter, or the PGK (phosphoglycerate kinase) promoter. The construction using the promoter of the FACC gene is preferred provided the level of expression obtained is compatible with a phenotypic correction.

Choice a the cDNA:

Three different complementary DNAs corresponding to three types of messenger RNAs were cloned for the complementation group C of Fanconi's disease; the open reading frame is identical irrespective of the complementary DNA considered . (Strathdee et al, 1992).

One of the messengers is largely predominant in the cells in culture. Its 5' end comprises only a part of the exon −1; on the other hand, the non-coding 3' end is very extensive. The flanking 3' sequences seem to have a decisive importance for the stability of the transcripts.

Whatever the complementary DNA chosen, the latter is excised by BamHI/XhoI cutting and introduced into the retroviral constructions in an antisense orientation as follows: upstream, XhuI is cohesive with the ends generated by SalI cutting; downstream the SphI site is made blunt, thus adapted to the BamHI site itself also made blunt.

1 Most of the complementary DNA is 4.5 kb (size corresponding approximately to the upper limit for a retroviral vector).

2- The DNA complementary to one of the other two messengers was also used in the sense orientation within the enhancer-free retroviral construction (del-U3) to test the potential advantage of using flanking 5' sequences and the −1 exon for the expression of the FACC gene; the cloning is then achieved by XbaI cut made blunt upstream to adapt to BamHI-blunt, the SalI-XhoI adaptation being made downstream.

3- Finally more simply, the complementary DNA corresponding to the regions coding for the FACC gene lacking flanking region; at 5' and 3' was introduced:
either in the native retroviral vector in the sense orientation with transcription governed by the retroviral LTRS
or in the enhancer-free retroviral vector in the sense orientation with transcription governed by a ubiquitous metallothionein or PGK (phosphoglycerate kinase) promoter.

5°- cDNA of the PLP gene deficient in patients suffering from the Pelizaeus-Metzbacher disease (Dautigny et al., 1986; Hutson L D et al., 1989; Morello et al., 1986).

Figure 24:
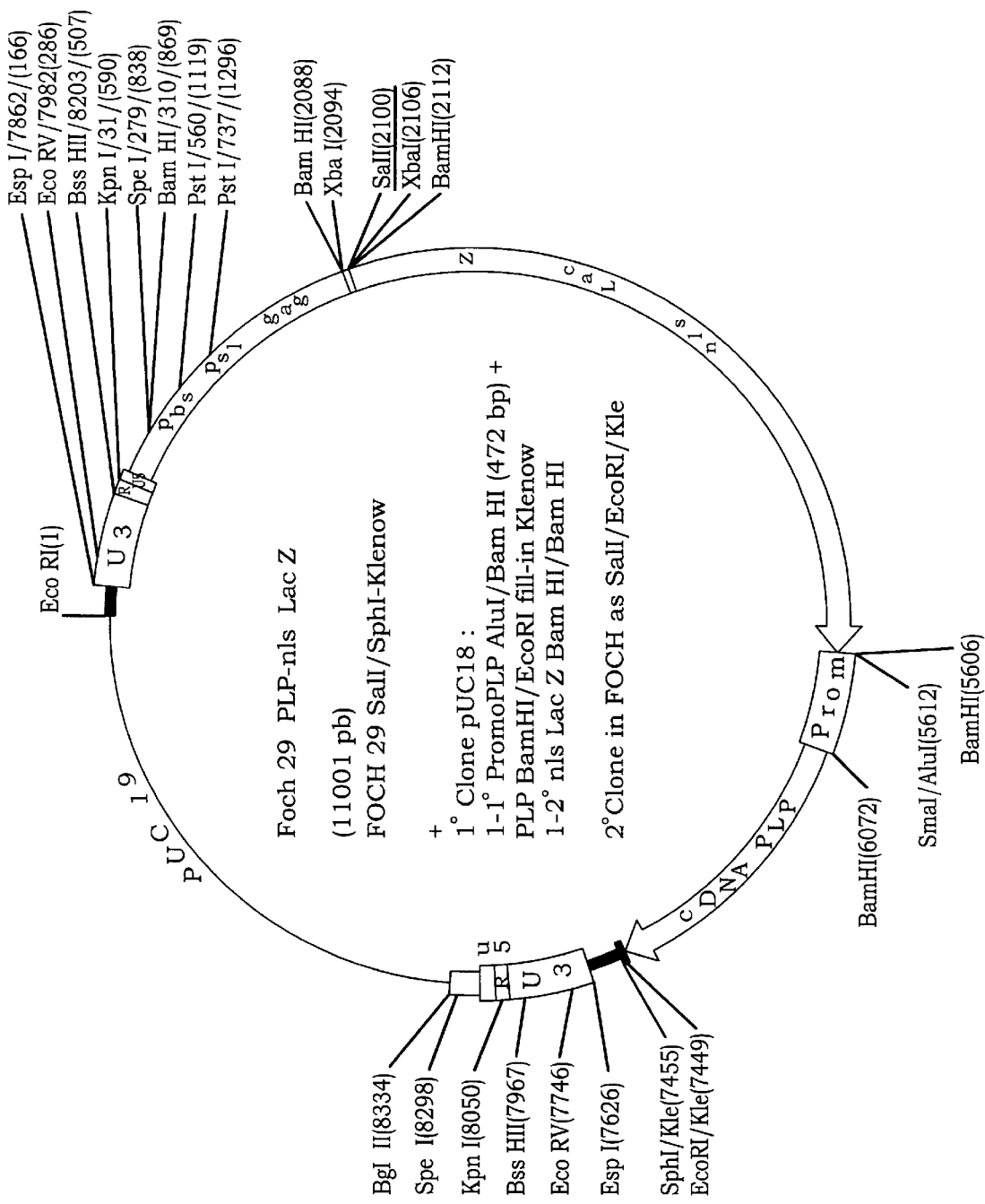

A construction (FIG. 24 was assembled for the time being in order both to express the PLP gene under its highly specific tropic natural promoter and inducible by glucocorticoids and to be able to monitor oligodendrocytes or Schwann cells expressing PLP in vivo after stereotaxic implantation in the brain.

For this purpose the gene coding for beta-galactosidase equipped with a nuclear localization signal (nls-Lacz) was placed under the direct dependence of the LTR The PLP promoter/complementary DNA-PLP sequences are placed downstream in the polylinkers. The BamHI-BamHI fragment of nls-Lacz was cloned in the BamHI site of the polylinkers of pSPT18. The AluI/BamHI and BamHI/EcoRI fragments (treated with Klenow in the presence of dNTPs) including respectively the PLP promoter and the PLP complementary DNA were cloned after ligation to the SmaI site upstream (in the case of AluI) and EcoRI site downstream in pSPT18.

The entirety of the insert is excised by EcoRI downstream, the end of the insert is treated with Klenow (blunt end) then SalI upstream; and adapted to the polylinker of FOCH29 upstream at SalI and downstream at SphI treated with Klenow (blunt end).

Other constructions in the del-U3 version of FOCH29 are planned including in reverse orientation the PLP promoter followed by a sequence comprising the first intron of the gene associated with the complementary DNA The presence of this intron ought to improve the expression and stability of the transcripts and allow a possible alternative splicing PLP-DM20.

6°-cDNA OF each OF the chains of interleukin 12: p35 and p40 in a polycistronic vector, construction described above as example of construction comprising IRES.

Other constructions may be obtained by including for example the following genes:
7°-TIMP: Tissue Inhibitor of Metalloproteinases
8°-TNF: Tumor Necrosis Factor
9°-IFN-gamma: gamma Interferon
10°-IFN-B: beta Interferon
11°-cytokine genes such as for example interleukin

C-CELL TARGETS

The vectors of the invention were used to transfect different stern cells. As examples the following cells are cited:
a-HEMATOPOIETIC STEM CELLS OF HUMAN ORIGIN The retroviral vector FOCH29 was initially constructed for the purpose of investigating a viral strain capable of infecting hematopoietic stem cells more effectively and of leading to a higher significant expression of the genes of interest in these cells than with the vectors currently used. This supposed effect is expected as a result of a particular tropism of the viral regulatory sequences, in particular U3 sequences of the LTRs.

The gene for neomycin resistance (neomycin phosphotransferase derived from the transposon Tn5) was introduced to form the vector FOCH29-Neo previously described and used as gene marker.

For one year the optimal conditions have been studied for the transduction of CD34+ hematopoietic progenitors of human origin, selected according to various methods obtained either from 11) blood of the umbilical cord, 21) bone marrow (allogenic graft), 31) stem cells of the peripheral blood mobilized by a combination of chemotherapy and growth factors.

Two orders of problems were envisaged:
1- Comparison of different procedures of viral infection
1-1 Use of viral supernatant versus coculture (on packaging cells producing the virus continuously) 1-2 Stimulation of the cells by different combinations of growth factors 2- Evaluation of the success of transfer: 2-1 absolutely, whatever the stage of differentiation of the transduced cells, by means of biological and molecular methods 2-2 in cells capable of representing pluripotential cells with the development of long-term cultures, in particular of xenogeneic stroma of mouse origin and sequential analysis of the clonogenicity of the cells.

The results (in detail below) obtained, in particular starting from viral supernatants, confirm the initial hypothesis of a remarkable efficiency OF the retroviral vector on the hematopoietic precursors.

The detail of the experimental protocols as well as the results obtained are described:

EXPERIMENTAL PROTOCOLS

1- COMPARISON OF DIFFERENT PROCEDURES OF VIRAL INFECTION
1-1. Use of viral supernatant versus coculture on packaging cells producing the virus continuously.

In fact, the use of cocultures presents major disadvantages for human uses relating to:
1) the potential contamination of the hematopoietic cells by xenogeneic cells and 2) the potential persistence of a multiplication of these producer cells in spite of their being irradiated (or their treatment by cytotoxic agents) prior to the use in coculture.

3) the significant increase of the risk of the generation of replication-competent virus as a result of the presence of sequences complementing the defective viruses, capable of inducing homologous and non-homologous recombination events with endogenous retroviral sequences or accidental, contaminating viruses of the culture media (Temin et al., 1990).

A comparison in parallel was made of the infection of the same unique cell source (CD34+ progenitors selected either from a unique sac of blood of the umbilical cord; or from a cytapheresis) separated into two equivalent samples from all points of view; one of them was placed in contact with an adherent sublayer of virus producer cells grown to 80% confluence on 1% gelatin in the presence of polybrene at a concentration of 2 mg/ml for 48 hours; the other sample was placed in a culture flask and covered with viral supernatant (undiluted with additional culture medium) freshly harvested from cultures of producer cells at confluence and filtered through a 0.45 μm membrane (removing all of the cells likely to have been taken with the supernatant), in the presence of polybrene at the same concentration. The infection protocol by viral supernatant was based on a repetition of four cycles over 36 hours, i.e. two cycles per day at an interval of eight hours on two successive days. The supernatant was simply added to the culture well without the hematopoietic cells being handled or centrifuged.

The culture medium used for the viral infection irrespective of the mode of infection corresponded to the medium optimized for hematopoietic stem cells, namely Iscove's modified DMEM (GIBCO-BRL) supplemented with 10% fetal calf serum (Boehringer-Mannheim) and 10% horse serum (GIBCO-BRL).

Each parameter was simultaneously tested in at least two wells in duplicate.

After infection, the cells were planted for long-term culture on xenogeneic stroma.

1–2. Stimulation of the cells of different combinations of growth factors.

Minimized quantities of growth factors were used in order to preserve maximally the pluripotentiality of the hematopoietic precursors which might be infected, the objective being to best treat the cells already spontaneously in cycle.

A comparison has been made on the same cell source and under the same condition of infection of:

1°-DIFFERENT COMBINATIONS OF GROWTH FACTORS (Stem Cell Factor: SCF; Leukemia Inhibiting Factor: LIF; Interleukin 3: IL3; Erythropoietin: Epo; Granulocyte-Macrophage stimulating factor: GM-CSF), namely:
SCF+LIF
SCF+LIF+IL3
SCF+LIF+IL3+Epo
SCF+LIF+IL3+GM-CSF 2°-DIFFERENT CONCENTRATIONS OF THESE DIFFERENT FACTORS
SCF: 50 ng/ml; 25 ng/ml; 10 ng/ml; 5 ng/ml
LIF: 10 U/ml; 5 U/ml; 1 U/ml
IL3: 10 U/ml; 1 U/ml; 0.1 U/ml
GM-CSF 10 ng/ml

2-EVALUATION OF THE SUCCESS OF TRANSFER 2-1 All cells taken together immediately after injection, giving rise to an initial percentage of transfected cells on the basis of molecular and biological methods:

CFU-GEMM (assay for the presence of mixed colonies Ganulous-Erythroid-Monocytes-Megakaryocytes) according to two forms:
without selection
with pharmacological selection by means of neomycin used at initially high doses, namely 1 mg/ml.
PCR (polymerase chain reaction) on individual colonies starting from the CFU-GEMM assays on methylcellulose subcultured on non-selected cultures; after subculturing the individual colonies were amplified to about $10^5$ cells per well by stimulation with a cocktail of growth factors containing: SCF 50 ng/ml; GM-CSF 50 ng/ml; IL3 10 U/ml; and Epo 2 U/ml. The cells were they lysed and analysed (of protocol and PCR primers indicated in the part).

2—2 in cells likely to be pluripotential cells

An assay of long-term cultures on xenogeneic stroma of murine origin (line MS5) was used and sequential analysis of the clongogenicity of the cells.

Long-term cultures on xenogeneic stroma, the adherent monolayer of which was produced beforehand on a film of 1% gelatin. These cultures were grown in "slide-flasks" of 9 $cm^2$ surface area (Nunc) for 60 days; each week half of the surface supernatant was removed and replaced by fresh medium containing a minimal cocktail of growth factors (Stem CE11 Factor: SCF 5 ng/ml; Leukemia Inhibiting Factor: LIF 5 U/ml; Interleukin 3: IL3 0.1 U/ml and erythropoietin: Epo 0.1 U/ml).

The long-term cultures were grown in normal medium or in a selective medium with a stroma genetically manipulated by transfection with a PGK-neo plasmid in order to be made resistant to neomycin.

The evaluation of the long-term cultures was based on:
the observation of the presence of islets of hematopoietic cells at the surface on the stroma cells (Cobblestone)
the starting at defined times of sequential CFU-GEMM assays with or without pharmacological selection for the presence of the gene for neomycin resistance. The cells sampled were numbered and seeded in aliquots of 1000 cell per analysis well. The cells were derived either from the surface supernatant generally taken each week or from a supernatant withdrawn so as to detach also the hematopoietic islets adhering to the stroma (in particular on D60 when the long-term cultures were stopped) as follows: all of the supernatant was taken, the culture dish was then covered with 1x PBS without calcium for one to two minutes; this detached the partially adherent cells. This second supernatant was itself removed, pooled with the first and the whole was centrifuged at very low speed (1000 revolutions/minute) on a cushion of fetal calf serum which protected the most fragile cells. One part of the cellular pellet was planted for CFU-GEMM, the other cells being simply reseeded on an zenogeneic stroma for long-term culture.
the molecular characterization of the viral integration was analyzed by sequential PCR assays on individual colonies taken from the CFU-GEMM (see above).
when a sufficient number of cells could be obtained at the outset and when the long-term cultures remained very rich, one part of the cells was taken for FACS analysis.

RESULTS

1-LONG-TERM CULTURES

The cultures were maintained successfully for 60 days without changing the stroma during this interval. At that date, the cultures were stopped and all of the remaining cells were seeded in CFU-GEMM. Colonies in CFU-GEMM assay seeded at 60 days from cells selected on neomycin were obtained. This confirms the efficient transduction of hematopoietic precursors capable of being maintained in long-term culture and the conservation of a genic expression for several months of the gene carried by the construction FOCH29 in the hematopoietic precursors.

2-COMPARISON OF DIFFERENT PROCEDURES OF VIRAL INFECTION 2-1 Use of viral supernatant versus coculture The remarkable efficiency of four repetitive cycles of infection by supernatant during two days, without manipulation of the cells has been observed in comparison with coculture on a packing line for 48 hours.

These data were authenticated by:
1° The maintenance of long-term cultures in the presence of a selection by neomycin on stroma resistant to neomycin; at D60 the cell cultures infected by supernatant still remained productive whereas the wells infected by coculture were unproductive.
2° The CFU-GEMM assays with a number of colonies, in particular mixed colonies, 4 to 5 times more numerous after infection by supernatant.
3° The molecular evaluation of viral integration by PCR on individual colonies subcultured and amplified from the CFU-GEMMs. In the case of the initial assays a transduction of up to 90% was detected after injection by supernatant.

2—2 Stimulation of the cells by different combinations of growth factors.

Of the multiple different combinations cited in the experimental protocol section, the minimal cocktail of growth factors (GFs) selected at minimal concentrations was the following: SCF 10 ng/ml+LIF 10 U/ml.

In fact, the significant long-term cultures after injection in the presence of IL3 at concentrations varying between 1 U/ml and 10 U/ml could not be maintained owing to a significant initial expansion without maintenance of a productive long-term culture.

Furthermore, no effect of the pretreatment by xenogeneic stroma except that a potential contamination by mouse cells was not observed.

These results thus show:
1° the feasibility of a productive retroviral infection without endangering the initiation potentila of long-term cultures, starting from a viral supernatant but not from a coculture.
2° the efficiency of both the viral transduction of the hematopoietic precursors of human origin derived from the CD34+ cells by means of the construction FOCH29; and the expression of the gene of interest throughout the long-term culture starting from this construction in these same cells.

These elements attest to the feasibility of therapeutic uses by means of this retroviral vector in human hematopoietic stem cells; this ought to be confirmed by the results of a protocol of clinical experimentation of graft labelling.

b-EPITHELIAL CELLS
  1°-Cells of the vesicular epithelium
    of rat, dog, monkey
    of human origin
  2°-Cells of the mammary epithelium
    of rat
    of human origin c-TUMOR CELLS
  1°-Cells of vesicular tumor
    of rat
    of human origin
  2°-Cells of mammary tumor
    of human origin d-ACCESSORY CELLS OF THE NERVOUS SYSTEM
  1°-Oligodendrocyte precursors
  2°-Schwann cells These two types of cells of mouse origin were infected with the construction FOCH29-Neo in order to evaluate the neurotropic tropism of the retroviral LTRs; the expression of the gene of interest being governed by the retroviral LTRs.

The oligodendrocytes were derived from primary cultures; in the case of the Schwann cells, the line MSC80 was used. After infection, the MSC80 cells were maintained in continuous culture and subjected to selection by neomycin for four months. The characteristic cellular morphology is maintained throughout this prolonged period of culture.

The preliminary demonstration of the success of the infection of these neurotropic cells and the maintenance of a satisfactory expression of the marker gene carried by the FOCH29 vector led to the continuation of the work in the direction of therapy: the construction of the vector FOCH29-PLP was then achieved. In fact, this gene is defective in patients suffering from the Pelizaeus-Metzbacher disease (Saugier-Veber et al., 1994). The therapeutic advantage of the retroviral transfer of a normal version of the gene into the glial progenitors responsible for the synthesis of the myelin of the central vervous system, or into genetically manipulated Schwann cells is evaluated in mouse models of the human disease (Jimpy mouse, Jimpy/MSD (Pham-Dinh et al., 1992) and Rumpshaker). We are currently monitoring the in vivo fate of genetically manipulated MSC80 cells, after stereotaxic reimplantation in the brain.

The construction FOCH29-PLP used the endogenous promoter of the PLP gene; this latter is also evaluated on a delU3 version of FOCH29, in which the transcription of the PLP gene is governed by its own promoter.

e-FIBROBLASTS
  1°-of murine origin
  2°-of canine origin
  3°-of non-human primate origin
  4°-of human origin f-CELLS OF HEMATOPOIETIC STROMA
  1°-of murine origin, in the line (line MS5) used for the long-term cultures of hematopoietic stem cells with expression over more than a year.
  2°-of canine origin on primary cultures of fetal medullary fibroblasts established in the laboratory.
  3°-of non-human primate origin
  4°-of human origin g-ENDOTHELIAL CELLS
h-MESENCHYMATOUS CELLS
i-MESOTHELIAL CELLS
j-KERATINOCYTES
k-HEPATOCYTES
l-LINES of human origin
  1°-of T LYMPHOCYTES: JURKATT
  2°-of NK CELLS: YT+b 2C+b 2
  3°-of MONOCYTES-MACROPHAGES: U+b 937
  4°-ERYTHRO-MEGAKARYOCYTIC: K+b 562

These four cells lines were infected with a viral supernatant either in a single cycle or in four cycles of infection (two cycles separated by an eight hour interval on two consecutive days). Sixteen hours after the infection the cells are subjected to selection by neomycin at various concentrations: 0.3 mg/ml; 0.5 mg/ml and 1 mg/ml.

A labelling assay with tritiated thymidine was performed one week after the infection (i.e. after five days of selection); this assay proved to be substantially positive for the lines with rapid growth: Jurkatt and K562 whatever the concentration of neomycin used.

After prolonged selection by neomycin during three weeks, the comparative analysis of cellular viability (cells in suspension) between the wells selected at different concentrations and the control wells without selection shows that a considerable percentage of actually transduced cells on which resistance to neomycin was conferred:

T CELL TUMOR LINE JURKATT: 75 to 80%
NK CELLS YT+b 2C+b 2: 30 to 50%
MONOCYTES-MACROPHAGES U+b 937: 40 to 60%
ERYTHRO-MAGAKARYOCYTIC K+b 562: 75 to 80%

IN VIVO MODEL OF RETROVIRAL TRANSFER APPLICATION TO BLADDER CANCER

Since the bladder is a hollow organ accessible by means of a simple endourethral probe, the forms of administration and the efficiency of gene transfer by direct endovesicular instillation in vivo were evacuated point by point. This evaluation involves several lines of parameters:

1°-Efficiency of retroviral transfer of the vesicular urothelium by in vivo endovesicular inoculation of viral supernatants transporting "reporter" constructions.

2°-Harmlessness of mechanical operations and the transduction of the epithelial cells 3°-Absence of systemic diffusion of the viral particles 4°-Preferential infection of the tumor cells compared with the healthy epithelium In fact, the superficial bladder tumors, developed at the expense of the vesicular urothelium in 90% of the cases show a progression marked essentially by a tendency to recurrence after complete excision by endoscopic surgery. A group at high risk of recurrence and progression may be defined and includes the tumors of stage pT1, multifocal tumors of stage pTa, in situ carcinomas or the associated dysplasias, an the multiple tumoral recurrences.

In this group, non-specific chemotherapy and immuno-therapy by the endovesicular route are used as prophylactic treatments of recurrences after endoscopic surgery. However, the endovesicular treatments currently available have proved incapable of eradicating the multiple tumoral recurrences, and even in certain cases the progression of the tumors. Original therapeutic protocols based on the transfer of genes inhibitor of tumoral invasion (TIMP gene, construction FOCH29) previously mentioned or capable of stimulating the endogenous immune response (constructions FOCH29-IL12, FOCH29-IFN-gamma previously cited), or even interfering with the transduction of the enhancer signals of proliferation in the tumor cells must hence be suggested.

PERSISTENCE OF PACKAGED DEFECTIVE VIRAL PARTICLES IN BIOLOGICAL FLUIDS

In this context the infectivity of the virions after incubation at 37° C. in the presence of urines (filtered through 0.45 μm membranes or non-filtered) volume by volume was analyzed at sequential time intervals as follows: 5 min; 10 min; 15 min; 20 min; 30 min; 45 min; 60 min; 75 min; 90 min; 120 min; 150 min; 180 min. It was possible to demonstrate by using the beta-gel marker gene with a nuclear localization signal that the viral titers did not vary during the first three hours; the relevance of an approach by in vivo endovesicular instillation associated with water intake restriction is confirmed.

REFERENCES

Anderson W F, McGarrity, Moen Rc. Report to the NIH Recombinant DNA Advisory Commitee on murine Replication-Competent Retrovirus (RCR) assays (Feb. 17, 1993). Hum Gene Ther, 4: 311–321, 1993

Cornetta K. Morgan R A, Anderson W F. Safety issues related to retroviral-mediated gene transfer in humans Hum. Gene Ther. 2: 5–14, 1991

Danos O, Mulligan RC Proc Natl Acad Sci USA 85: 6460–64, 1988

Danos O Practical Molecular Virology 17–27 In Collins M, the Humana Press, Clifton, N.J., 1991

Dautigny A, Mattei M G, Morello D et al. The structual gene coding for myelin-associated proteolipid protein is mutated in Jimpy mice. Nature 321: 867–875, 1986

Donahue Re, Kessler S W, Bodine Det Al. Helper virus induced T cell lymphoma in non-human primates after retroviral-mediated gene transfer. J. Exp. Med., 176, 1125–1135, 1992

French Anderson W Human gene Therapy Science 256: 808–813, 1992

Gunter K C, Khan A S, Nogushi P D. The safety of retroviral vectors. Hum. Gen. Ther, 4, 643–645, 1993

Hudson L D, Puckett C, Berndt J, Chan J, Genecic S. Mutation of the proteolipid protein gene PLP in a human X chromosome-linked disorder. Proc. Natl. Acad. Sci. USA, 45: 435–442, 189

Kessler D A, Siegel J P, Nogushi P D, Zoon K C, Feiden K L, Woodcock J. Regulation of Somatic-cell therapy and gene therapy by the food and drug receptor protooncogene J. Biol. Chem. 264: 5488–5494, 1989

McLachlin J R. Cornetta K, Eglitis M A, Anderson W F Retroviral-mediated gene transfer Progress in Nucleic Acid Research and Molecular Biology 38: 91–135, 1990

Masuda M, Remington M P, Hoffman P M, Ruscetti S. Molecular characterization of a neuropathogenic and non-erythroleukemogenic variant of Friend murine leukemia virus PVC-211. J. virol, 66: 2798–2806, 1992

Mathieu-Mahul D, Heard J M, Fichelson S, Gisselbrecht S, Sola B, LarsenC Virology 119: 59–67, 1982

Miller A D Human gene therapy comes of age Nature 357: 455–460, 1992

Monsigny M. et al médecine/sciences 9:441–9, 1993

Morello D, Dautigny A, Pham-Dinh D, Jolles P. Myelin proteolipid (PLP and DM20) transcripts are deleted in Jimpy mutant Mice. EMBO J 5: 3489–3493, 1986

Morgan R A, Couture L, Elroy-Stein O, Ragdeb J, Moss B, French Anderson W. Retroviral vectors containing putative internal ribosome entry sites: development of a polycistronic gene transfer systems and applications to human gene therapy. Nucleic Acids Res, 20: 1293–1299, 1992

Mulligan R C The basic science of gene therapy Science 260: 926–931, 1993

Perryman S, Nishio J, Chesebro B Complete nucleotide sequence of Friend murine leukemia virus, strain FB29 Nucl Acid Res 19: 6950, 1991

Remington M P, Hoffman P M, Ruscetti S, Masuda M. Complete nucleotide sequence of a neuropathogenic variant of Frien murine leukemia virus PVC-211. Nucl Acids Res, 20: 3249, 1992

Saugier-Veber P, Munnich A, Bonneau D, Rozet J M, Le Merrer M, Gil R, Boespflug-Tanguy O. X-linked spastic paraplegia and Pelizaeus-Mersbacher disease are allelic disorders at the proteolipid protein locus. Nat. Genet. 6: 257–261, 1994

Sitbo M, Sola B, Evans L, Nishio J, Hayes S F, Nathanson K, Garon C F, Chesebro B Cell 47: 851–859, 1986

Sitbon M, Ellerbrok H, Pozo F, Nishio J, Hayes S F, Evans L H, Chesebro B J Virol 64: 2135–40, 1990

Sitbon M, d'Auriol L, Ellerbrok H, André C, Nishio J, Perryman S, Pozo f, Hayes S F, Wehrly K, Tambourin P, Galibert F, Chesebro B Proc Natl Acad Sci USA 88: 5932–5936, 1991

Strathdee C A, Gavish H, Shannon W R, Buchwald M. Cloning of cDNAs for Fanconi's anaemia by functional complementation. Nature, 356: 763–767, 1992

Temim H M, Safety considerations in somatic gene therapy of human disease with retrovirus vectors. Hum. Gene Ther. 1: 11–123, 1990

Yee J K, Moores J C, Jolly D J, Wolff J A, Respes J G, Friedmann T. Gene expression from transcriptionally disabled retroviral vectors. Proc Natl Acad Sci USA, 84: 5197–5201, 1987

Yu S F, von Ruden T, Kantoff P W, Garber C, Seiberg M, Ruther U, French Anderson W, Wagner E F, Gilboa E. self-inactivating retroviral vectors designed for transfer of whole genes into mammalian cells. Proc. Natl Acad Sci USA, 83: 3194–3198, 1986

Maekawa T et al, J Biol Chem 264: 5488–5494, 1989

What is claimed is:

1. A retroviral vector comprising an isolated nucleotide sequence comprising a 5' long terminal repeat of Friend Murine Leukemia Virus, a primer binding site of Friend Murine Leukemia Virus, a packaging sequence of Friend Murine Leukemia Virus and a 3' Long terminal repeat of a Friend Murine Leukemia Virus, wherein said vector comprises a nucleotide sequence selected from the group consisting of SEQ ID NO: 11, SEQ ID NO:12, and SEQ ID NO:13.

2. The retroviral vector according to claim 1, wherein the Friend Murine Leukemia Virus is strain FB29.

3. The retroviral vector according to claim 1, wherein the retroviral vector lacks a nucleotide sequence encoding functional env and pol gene products of Friend Murine Leukemia Virus.

4. The retroviral vector according to claim 1, wherein the isolated nucleotide sequence has a sequence from nucleotide position 7702 to nucleotide position 1527 of FIG. 1 (SEQ ID NO: 11).

5. The retroviral vector according to claim 1, wherein the isolated nucleotide sequence has a sequence from nucleotide position 7806 to nucleotide position 1527 of FIG. 1 (SEQ ID NO: 12).

6. The retroviral vector according to claim 1, wherein the isolated nucleotide sequence has a sequence from nucleotide position 7702 to nucleotide position 310 of FIG. 1 (SEQ ID NO: 13).

7. The retroviral vector according to claim 1, further comprising a nucleotide sequence that encodes all or a portion of a gag gene product of Friend Murine Leukemia Virus.

8. The retroviral vector according to claim 7, wherein the nucleotide sequence encoding a portion of the gag gene product has a sequence from nucleotide position 619 to nucleotide position 1031 of FIG. 1 (SEQ ID NO:16).

9. The retroviral vector according to claim 7, wherein the nucleotide sequence encoding the portion of the gag gene product has a sequence from nucleotide position 619 to nucleotide position 1527 of the sequence shown in FIG. 1 (SEQ ID NO:15).

10. The retroviral vector according to claim 7, wherein the nucleotide sequence encoding a gag gene product has a sequence from nucleotide position 619 to nucleotide position 2235 of FIG. 5(SEQ ID NO: 14).

11. The retroviral vector of claim 1, wherein said vector is a plasmid.

12. The retroviral vector of claim 11, wherein the plasmid is pFOCH29 deposited with CNCM as No. I-1326.

13. The retroviral vector of claim 1, further comprising at least one nucleotide sequence encoding a polylinker, wherein the polylinker has nucleotide sequence restriction sites not found in the isolated nucleotide sequence, and wherein the polylinker is located between the packaging sequence and the 3' long terminal repeat.

14. The retroviral vector according to claim 1, wherein the vector has a titer of about $10^4$ PFU per ml. or greater.

15. The retroviral vector of claim 14, wherein the vector has a titer of about $10^6$ PFU per ml. or greater.

16. The retroviral vector according to claim 1, further comprising a nucleotide sequence encoding an IntraRibosome entry site (iRES).

17. The retroviral vector according to claim 1, wherein said 5' terminal repeat of Friend Murine Leukemia Virus, said primer binding site of Friend Murine Leukemia Virus and said packaging sequence of Friend Murine Leukemia Virus are encoded by the nucleotide sequence of SEQ ID NO: 11, and said 3' long terminal repeat of Friend Murine Leukemia Virus is encoded by the nucleotide sequence of SEQ ID NO: 13.

18. The retroviral vector according to claim 1, wherein said 5' long terminal repeat of Friend Murine Leukemia Virus, said primer binding site of Friend Murine Leukemia Virus and said packaging sequence of Friend Murine Leukemia Virus are encoded by the nucleotide sequence of SEQ ID NO: 12, and said 3' long terminal repeat of Friend Murine Leukemia Virus is encoded by the nucleotide sequence of SEQ ID NO: 13.

19. The retroviral vector according to claims 17 or 18, further comprising a polylinker sequence between said packaging sequence and said 3' long terminal repeat.

20. The retroviral vector according to claim 19, further comprising at least one exogenous nucleotide sequence encoding a polypeptide operably linked to the isolated nucleotide sequence.

21. A self inactivating retroviral vector comprising: an isolated nucleotide sequence comprising a 5' long terminal repeat from Friend Murine Leukemia Virus, a primer binding site from Friend Murine Leukemia Virus, a packaging sequence from Friend Murine Leukemia Virus and a 3' long terminal repeat of Friend Murine Leukemia Virus wherein the 3' long terminal repeat has a deletion of the nucleotide sequences encoding the viral promoter and enhancer sequences.

22. The retroviral vector according to claim 21, further comprising an expression cassette wherein the expression cassette is operably linked to the isolated nucleotide sequence and wherein the expression cassette comprises at least one exogenous nucleotide sequence operably linked to an exogenous promoter.

23. An Oligonucleotide primer sequence selected from the group consisting of:

a. 5' CTGCTGACGGGAGAAGAAAAAC-3 (SEQ ID NO:3);

b. 5' CCCGCTCAGAAGAACTCGTC-3' (SEQ ID NO:4);

c. 5' GACGAGTTCTTCTGAGCGGG-3(SEQ ID NO:5); and d. 5' GATCTGAACTTCTCTCTATTCTTG-3' (SEQ ID NO:6).

* * * * *